(12) United States Patent
Schultz

(10) Patent No.: US 7,802,574 B2
(45) Date of Patent: Sep. 28, 2010

(54) MEDICAL COMPONENT SYSTEM

(76) Inventor: Joseph P. Schultz, P.O. Box 26879, Phoenix, AZ (US) 85068

( * ) Notice: Subject to any disclaimer, the term of this patent is extended or adjusted under 35 U.S.C. 154(b) by 1525 days.

(21) Appl. No.: 10/123,966

(22) Filed: Apr. 16, 2002

(65) Prior Publication Data

US 2002/0108614 A1 Aug. 15, 2002

Related U.S. Application Data

(63) Continuation-in-part of application No. 09/484,666, filed on Jan. 18, 2000, now abandoned.

(51) Int. Cl.
*A61M 16/00* (2006.01)
*A62B 9/06* (2006.01)
*A61M 1/00* (2006.01)
*A61D 1/12* (2006.01)

(52) U.S. Cl. .................. 128/207.14; 604/317; 604/322; 604/540; 606/106

(58) Field of Classification Search ............ 128/207.14, 128/846, 852, 207.15, 207.16; 604/540, 604/317–323; 606/106
See application file for complete search history.

(56) References Cited

U.S. PATENT DOCUMENTS

| | | | | |
|---|---|---|---|---|
| 3,991,762 A | * | 11/1976 | Radford | ...................... 604/119 |
| 4,643,197 A | * | 2/1987 | Greene et al. | ............... 600/575 |
| 4,872,579 A | * | 10/1989 | Palmer | .................. 128/205.19 |
| 5,368,017 A | * | 11/1994 | Sorenson et al. | ....... 128/200.26 |
| 5,433,195 A | * | 7/1995 | Kee et al. | ............... 128/207.14 |
| 5,562,077 A | * | 10/1996 | Schultz | .................. 128/207.14 |
| 5,653,231 A | * | 8/1997 | Bell | ...................... 128/207.16 |
| 5,775,325 A | * | 7/1998 | Russo | .................. 128/205.12 |
| 6,082,361 A | * | 7/2000 | Morejon | ................ 128/207.15 |
| 6,408,850 B1 | * | 6/2002 | Sudge | .................. 128/207.17 |

* cited by examiner

*Primary Examiner*—Melanie J Hand
(74) *Attorney, Agent, or Firm*—Stoneman Volk Patent Group; Martin L. Stoneman; Michael D. Volk, Jr.

(57) ABSTRACT

Medical component systems are described in which individual hand-held components are enhanced by adjacent restraint and by combinations of function, including: suction devices with a port for regulating suction with single-finger-operable valve for repeatable incremental user control of suction-vacuum variation by aperture shapes like triangles and slots and tactile feedback means like plane changes for amplifying tactile feedback to a user to enhance distinguishing of control increments; clips and tubing restraints for attachment between devices; endotracheal tubes with feedback features so a user knows where the distal end is; wound kits and splash shields for use in combination with various irrigation sources; combination cough shields with medical components; endotracheal tube adapters with less dead space and improved flanges and monitoring ports; and improved long syringes and medical lights.

39 Claims, 30 Drawing Sheets

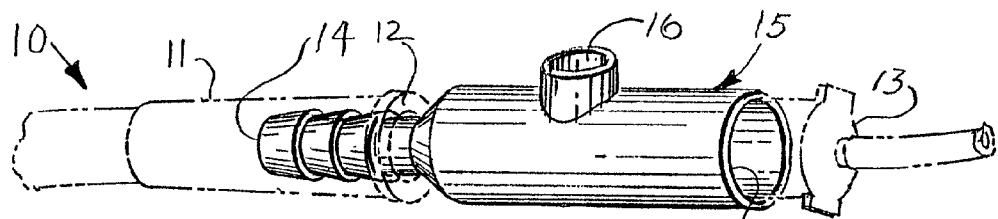
FIG. 2A PRIOR ART
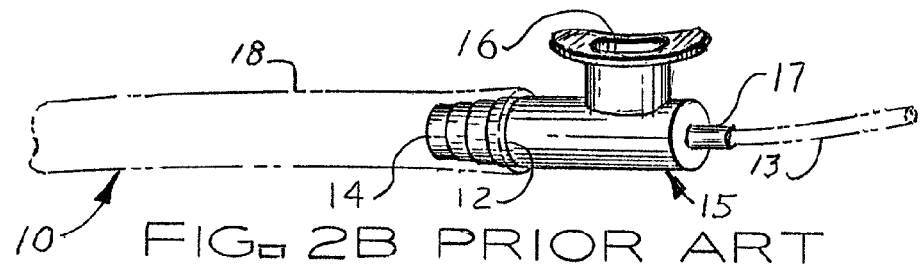
FIG. 2B PRIOR ART
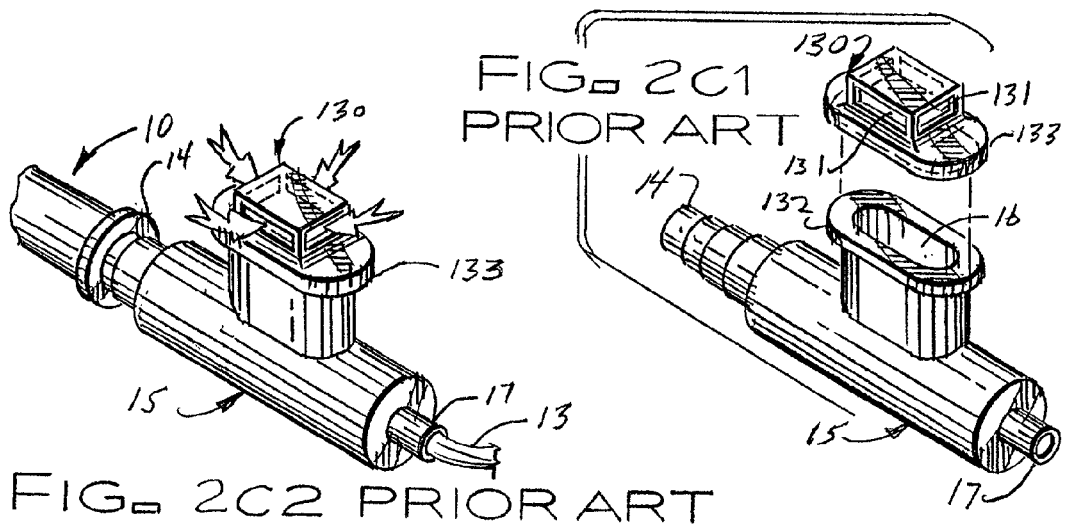
FIG. 2C1 PRIOR ART
FIG. 2C2 PRIOR ART
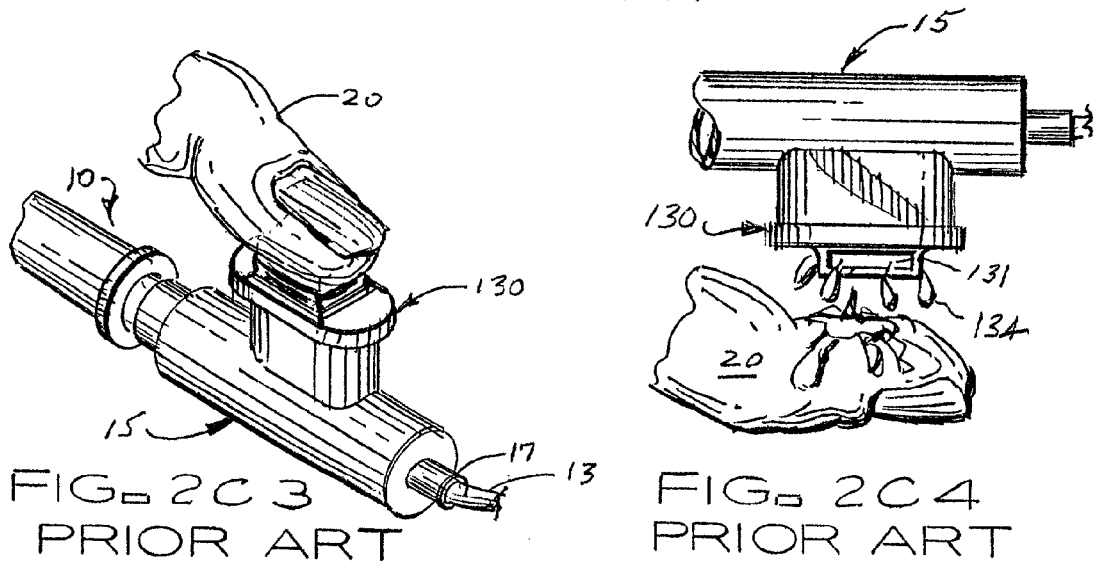
FIG. 2C3 PRIOR ART
FIG. 2C4 PRIOR ART

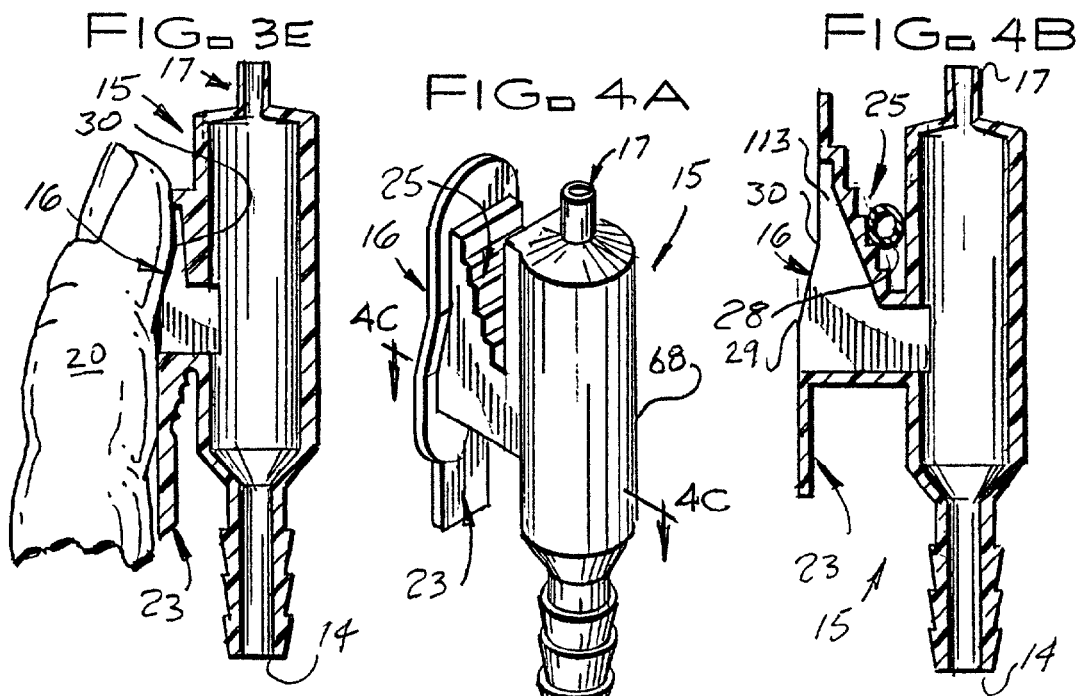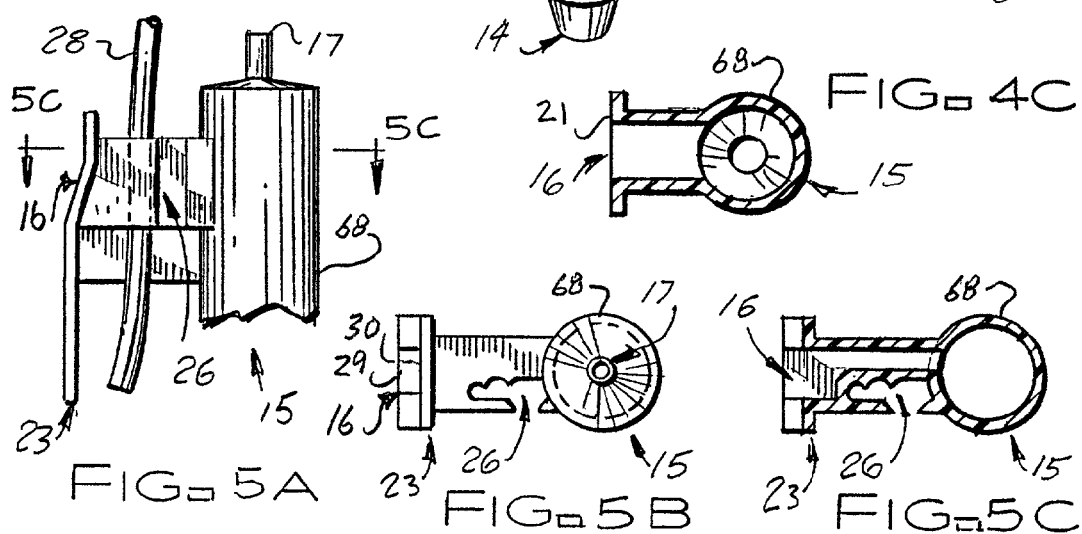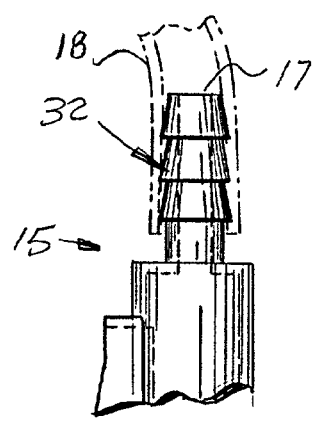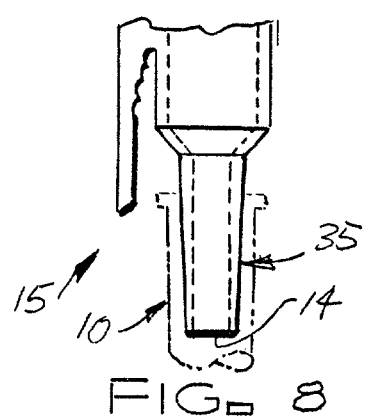

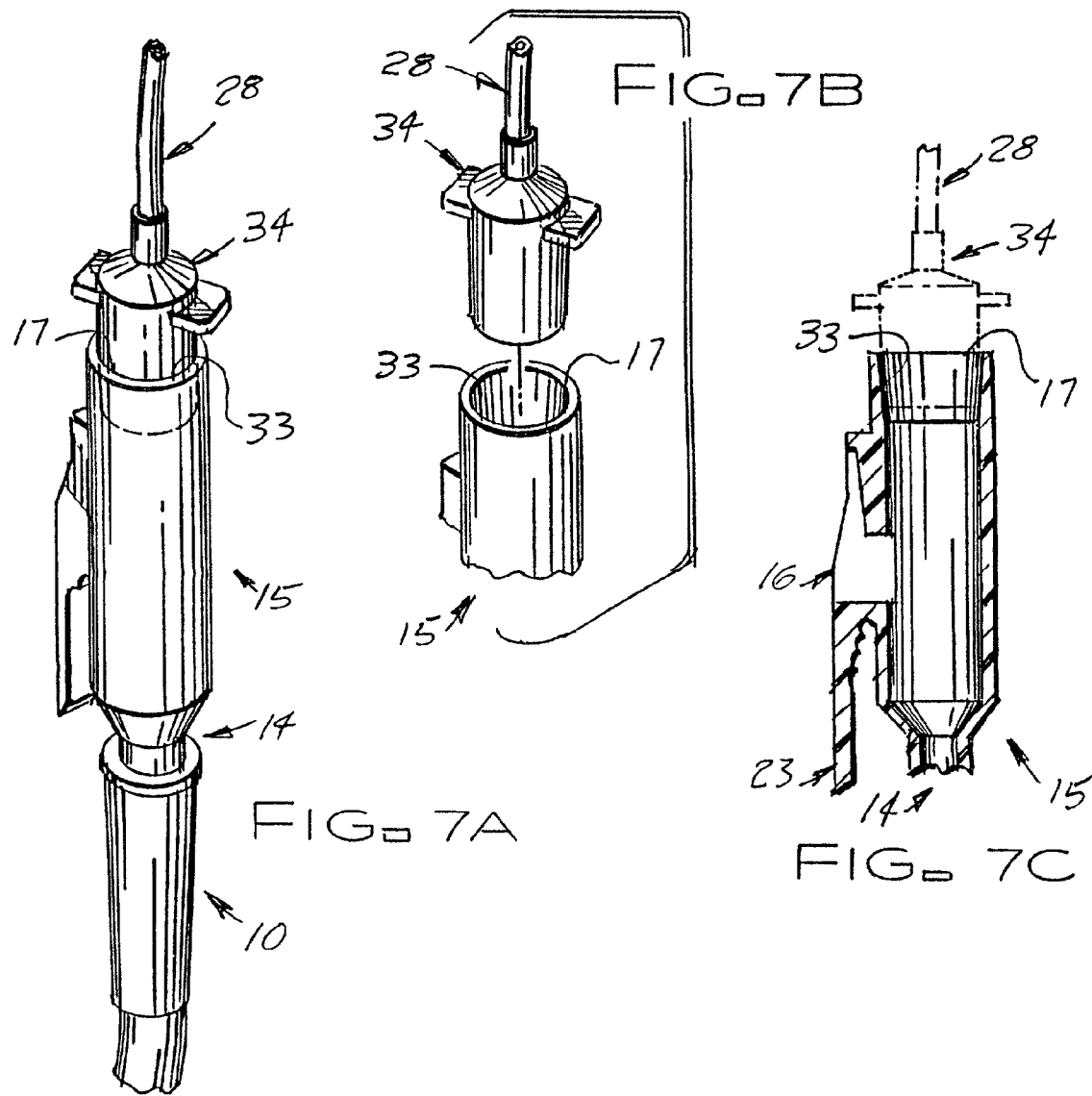

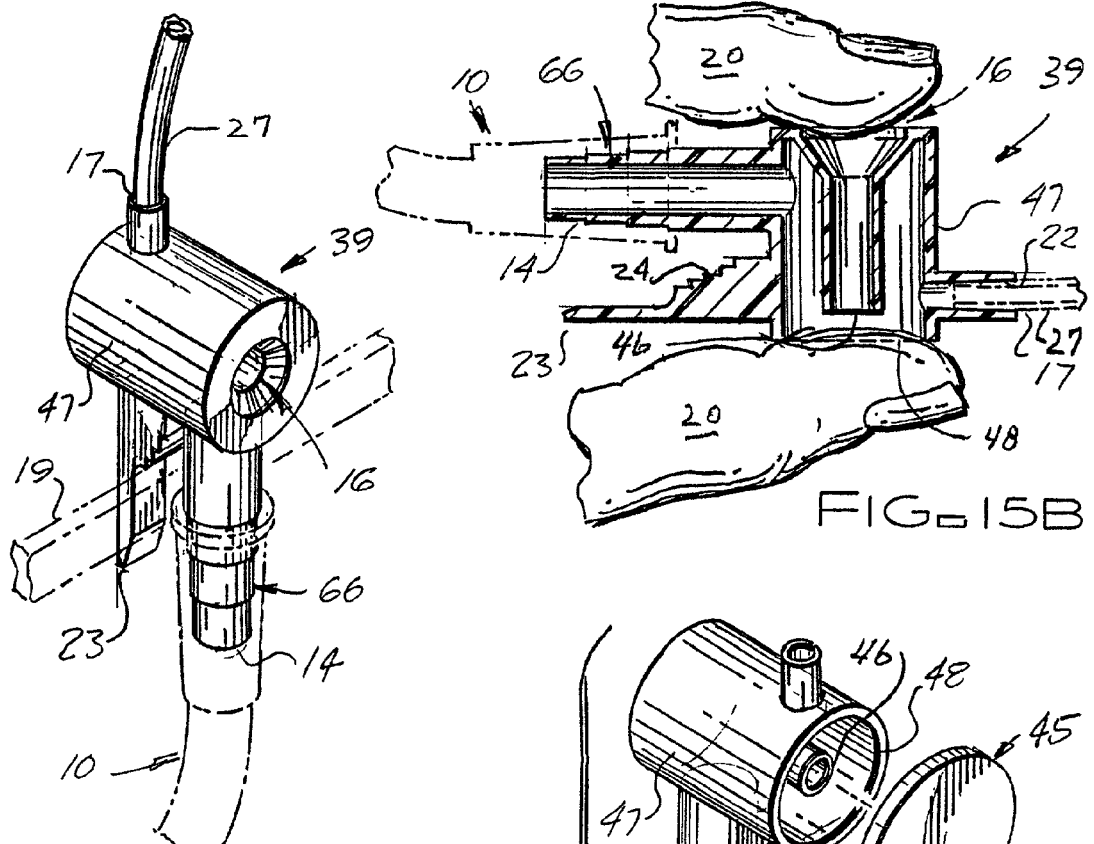
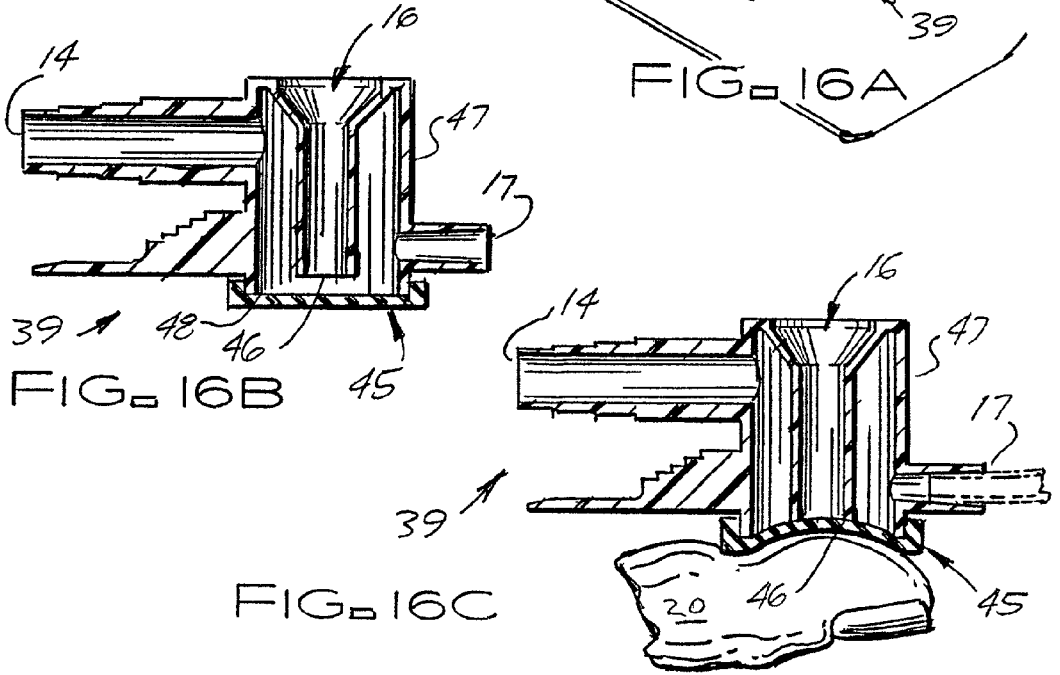

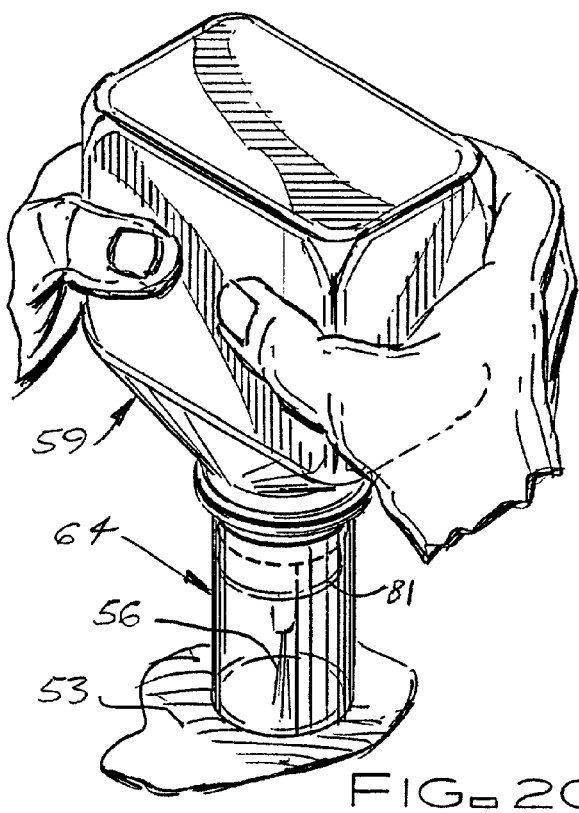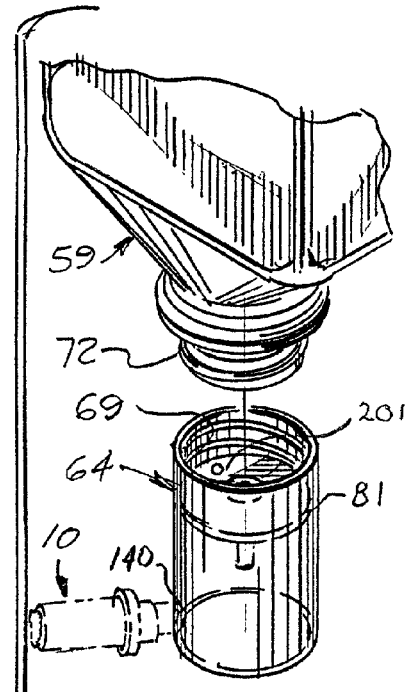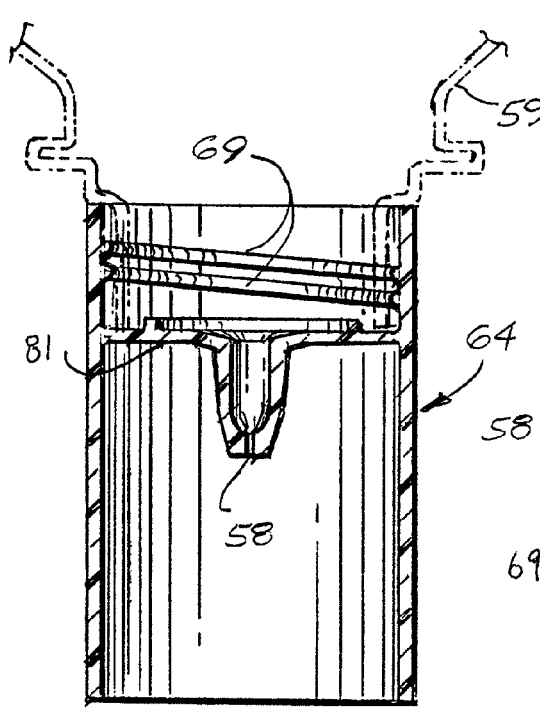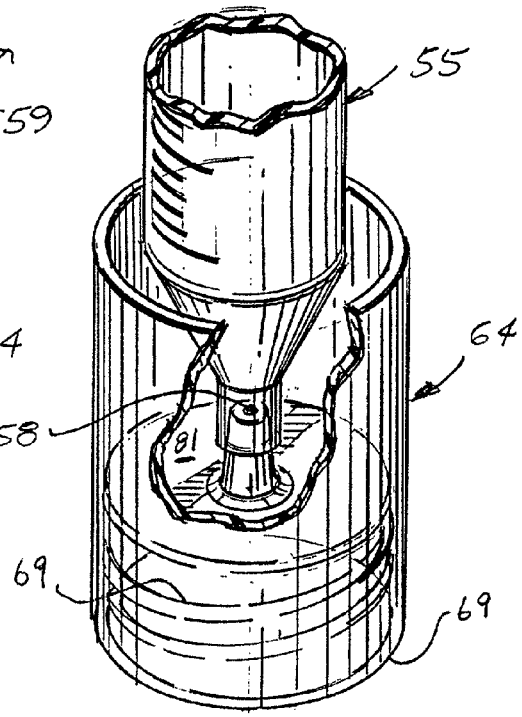
FIG. 20A
FIG. 20B
FIG. 20C
FIG. 20D

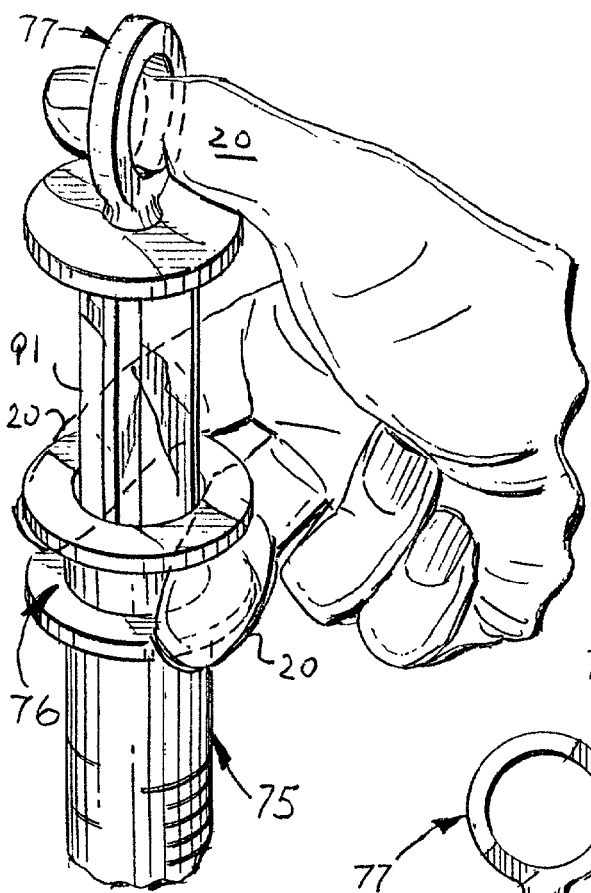
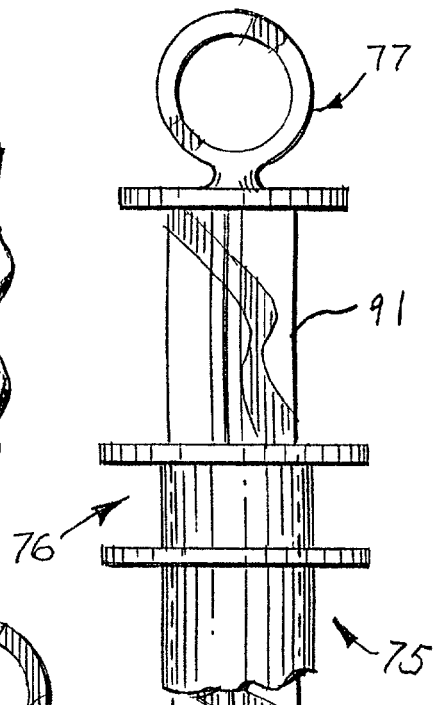
FIG. 21B
PRIOR ART
FIG. 21A
PRIOR ART
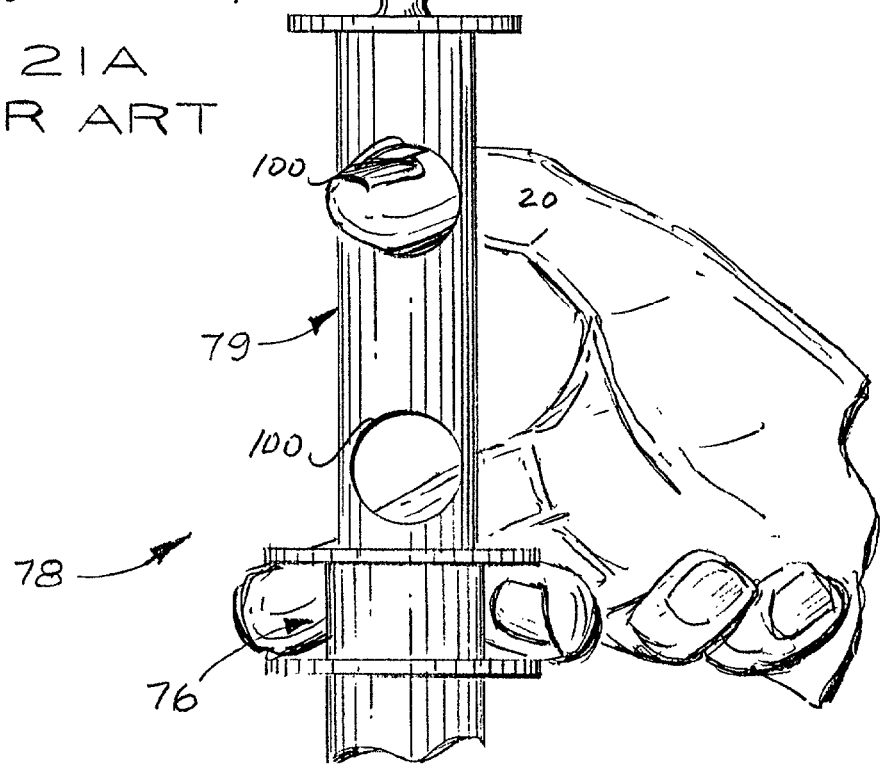
FIG. 22

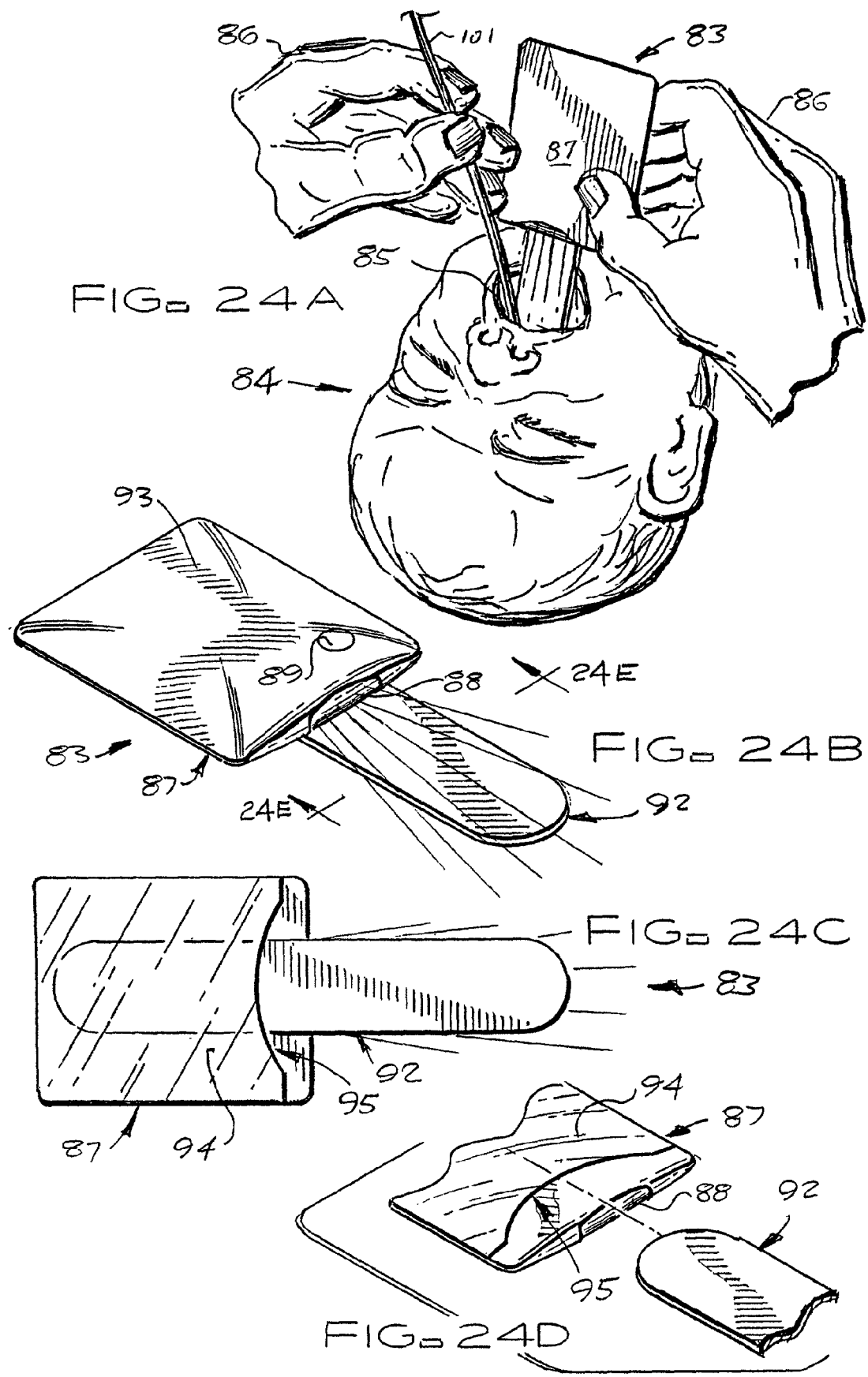

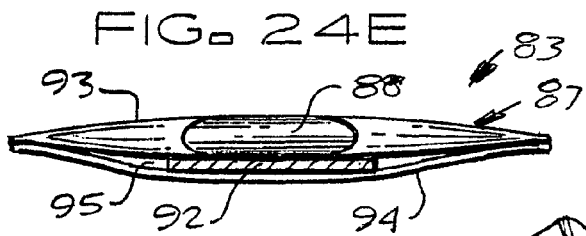
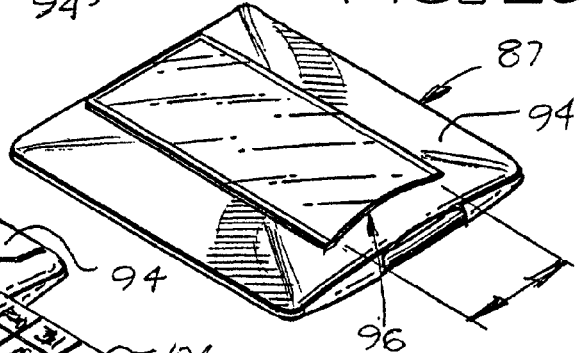
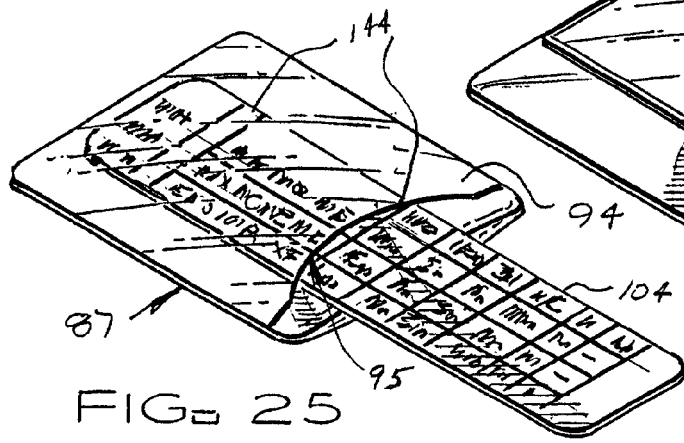
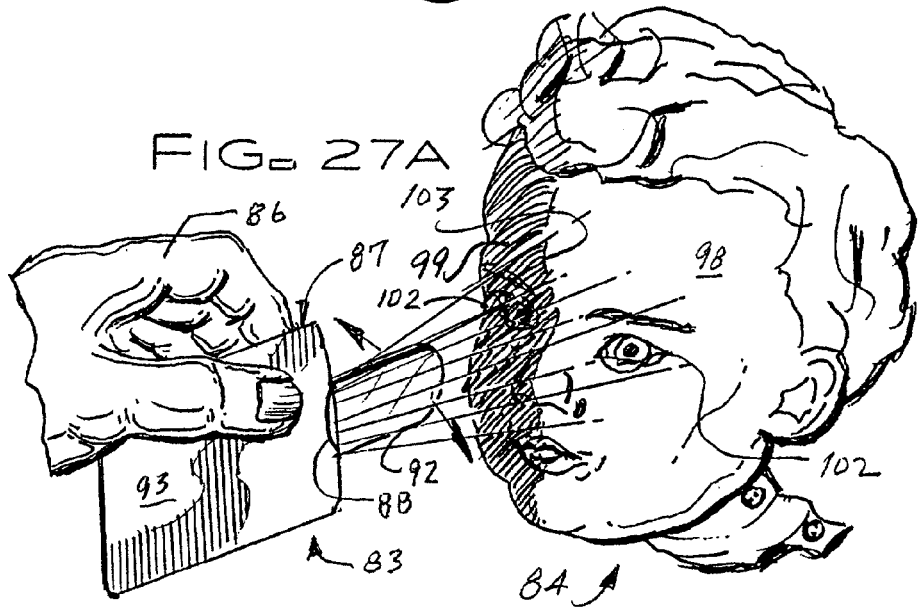
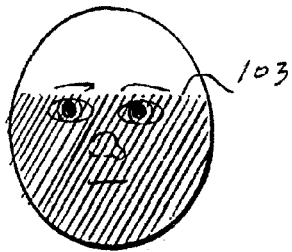
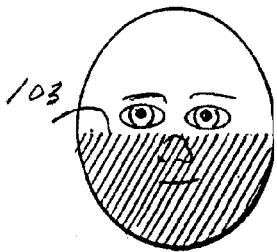

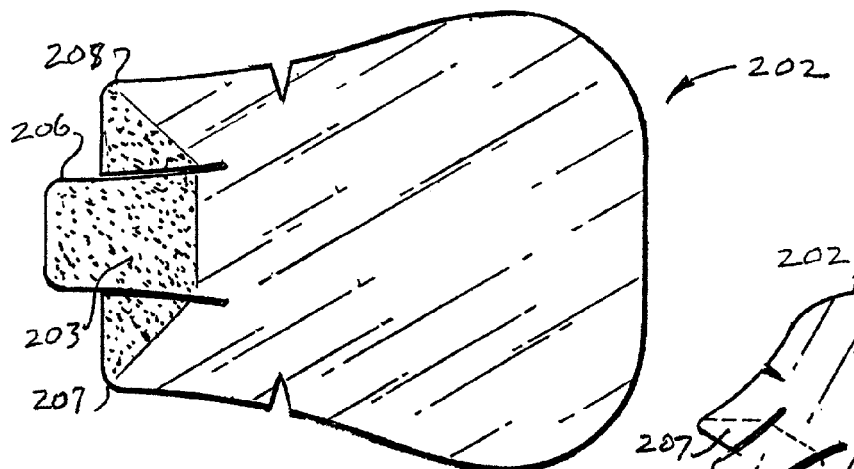
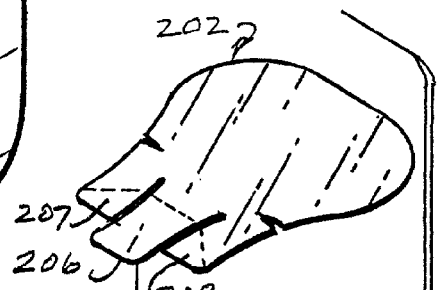
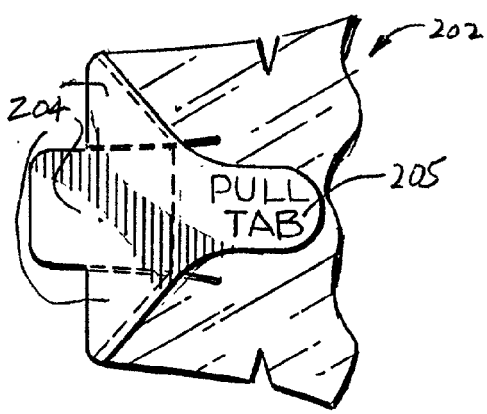
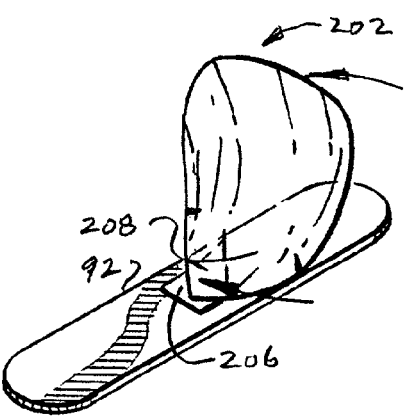
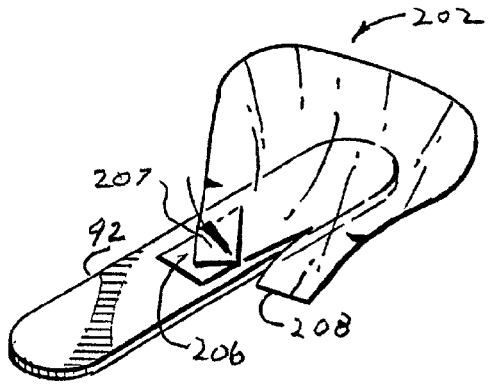
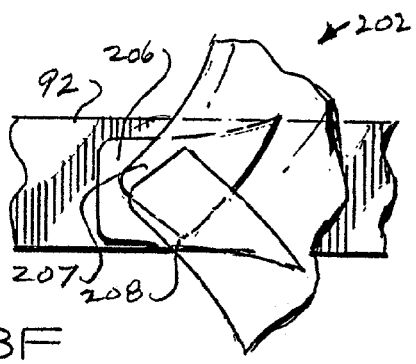

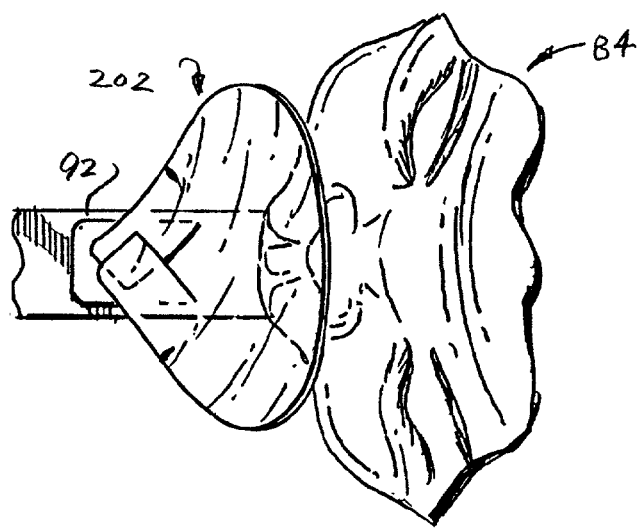
FIG. 28G
FIG. 28H
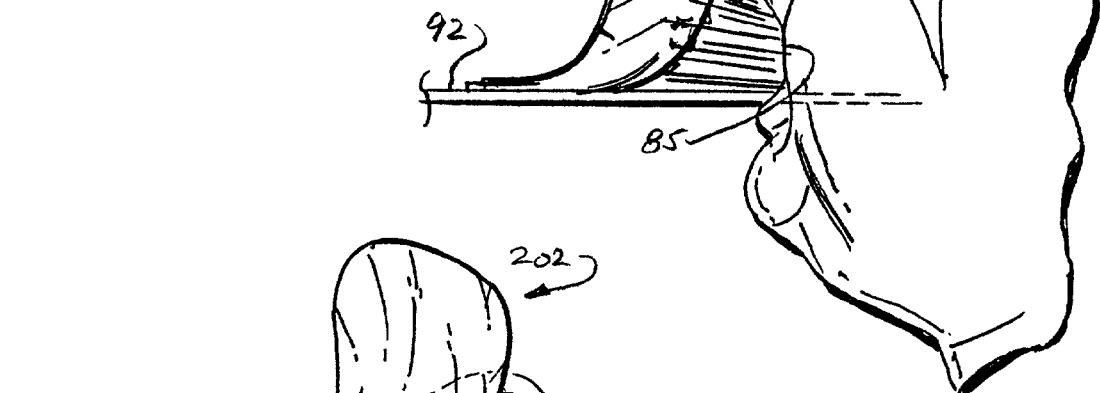
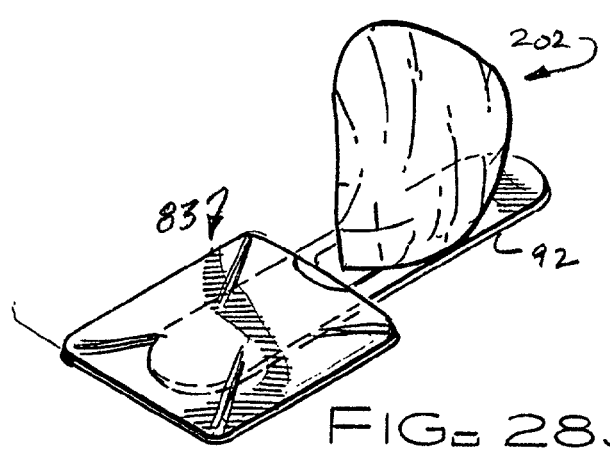
FIG. 28J

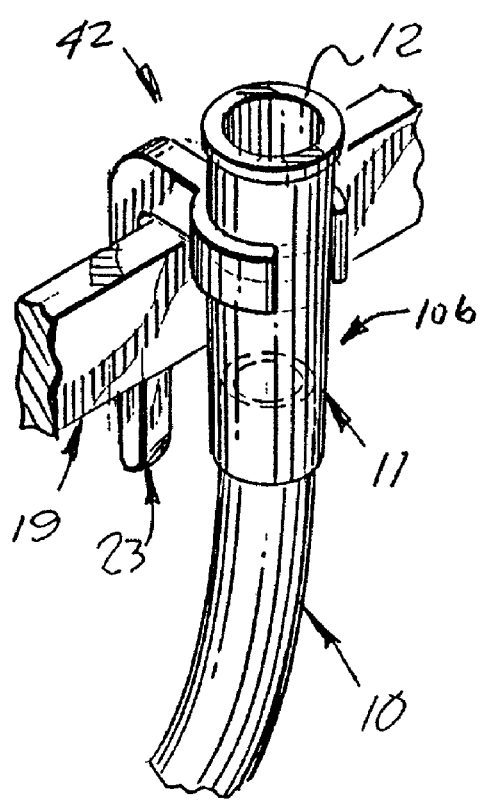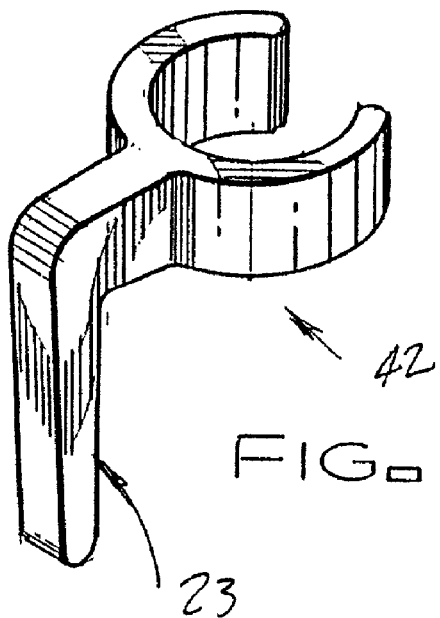

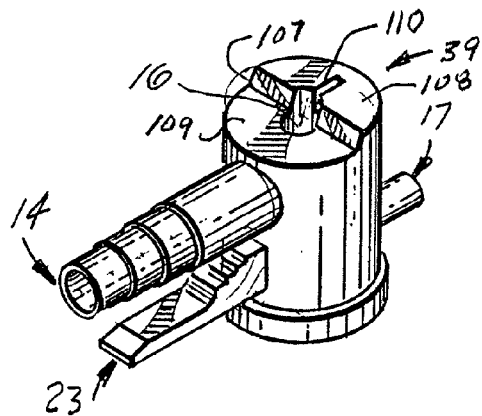
FIG. 30A
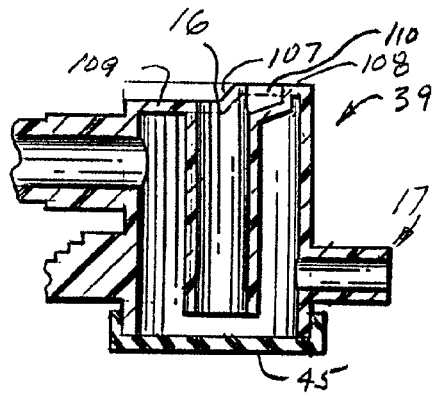
FIG. 30B
FIG. 31A
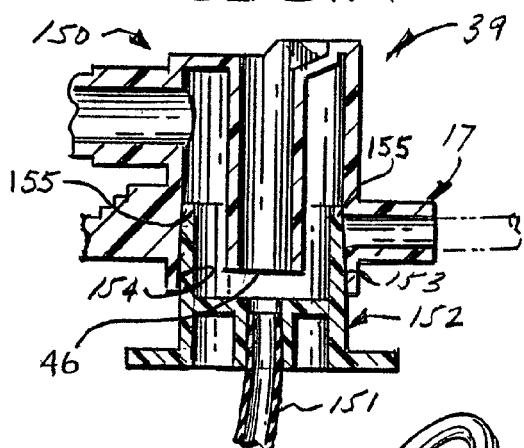
FIG. 31B
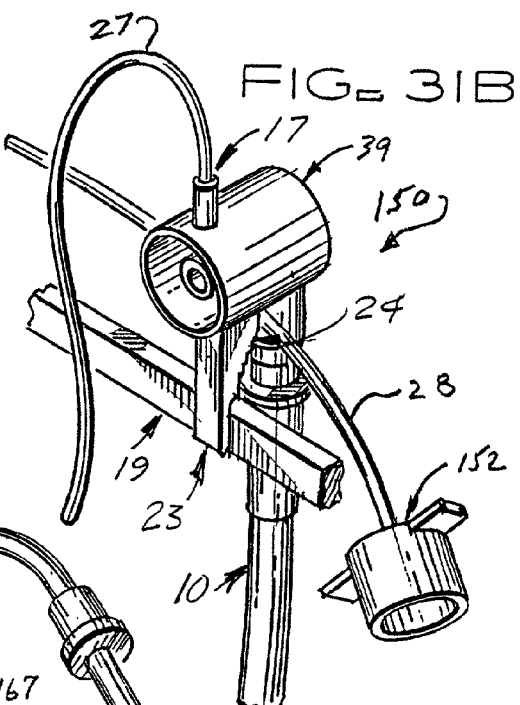
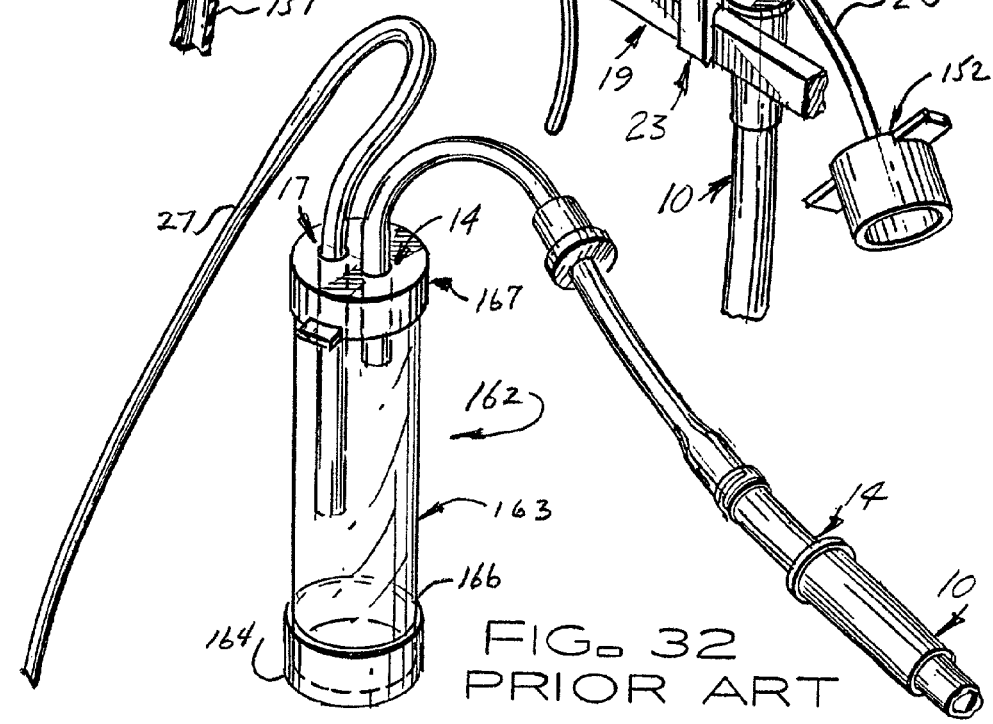
FIG. 32
PRIOR ART

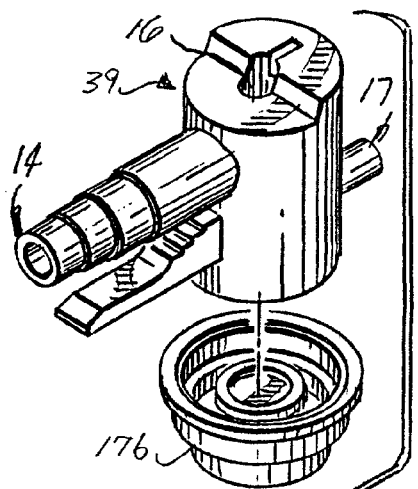
FIG. 33A
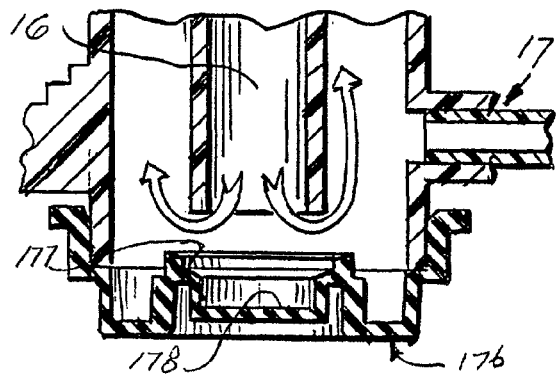
FIG. 33B
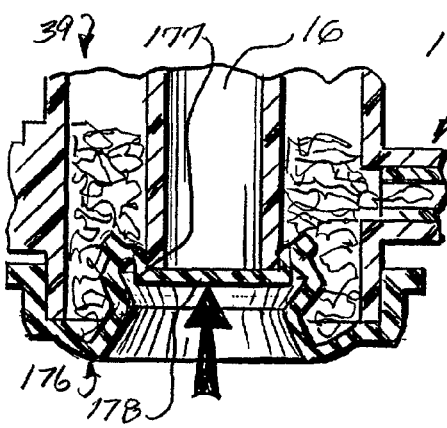
FIG. 33D
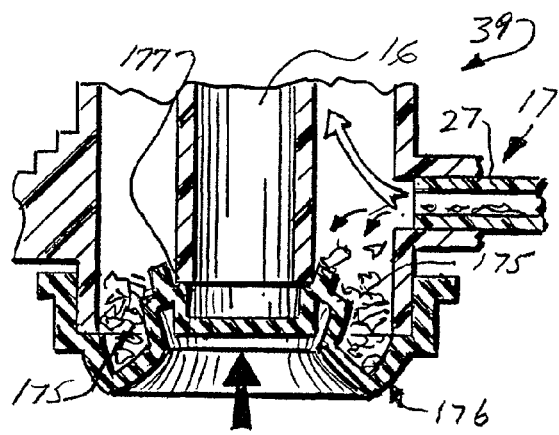
FIG. 33C
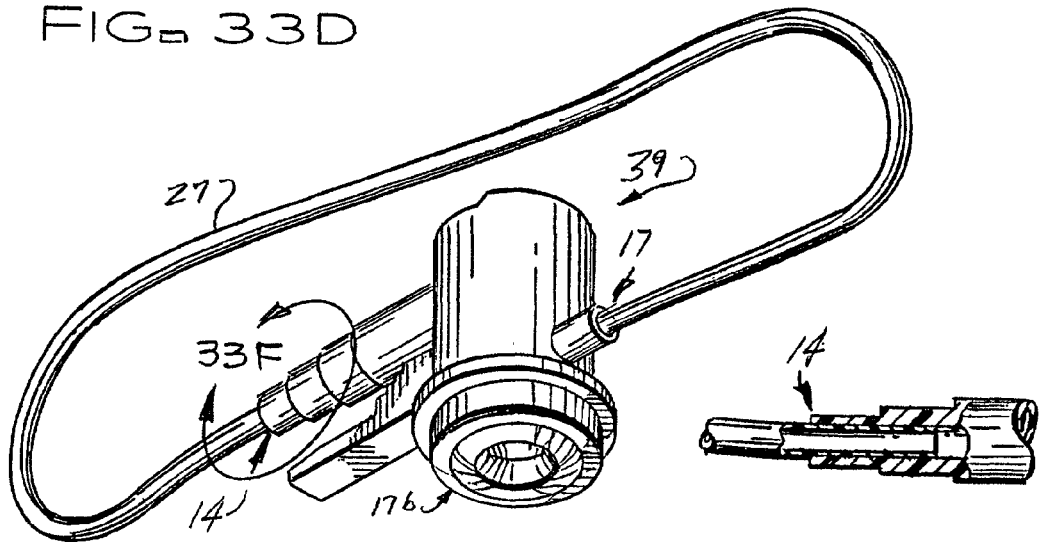
FIG. 33E
FIG. 33F

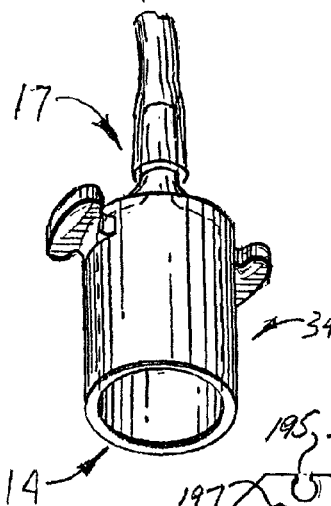
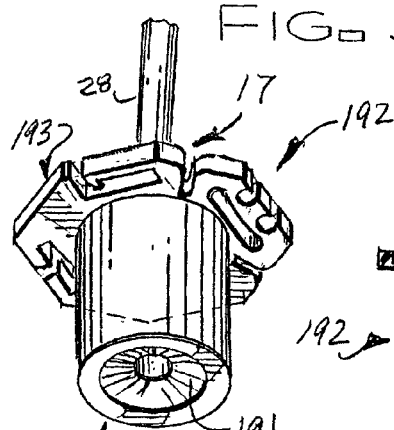
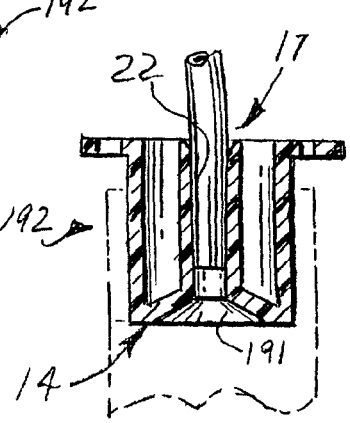
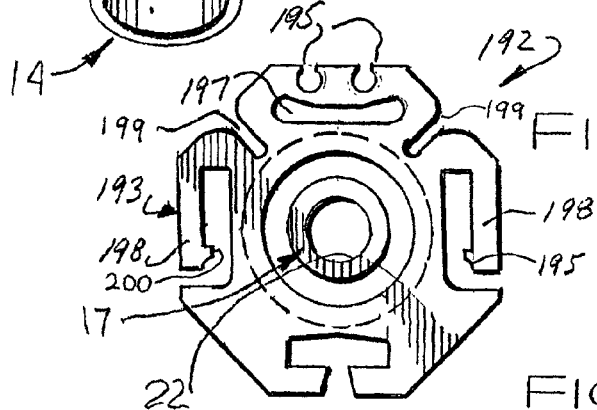
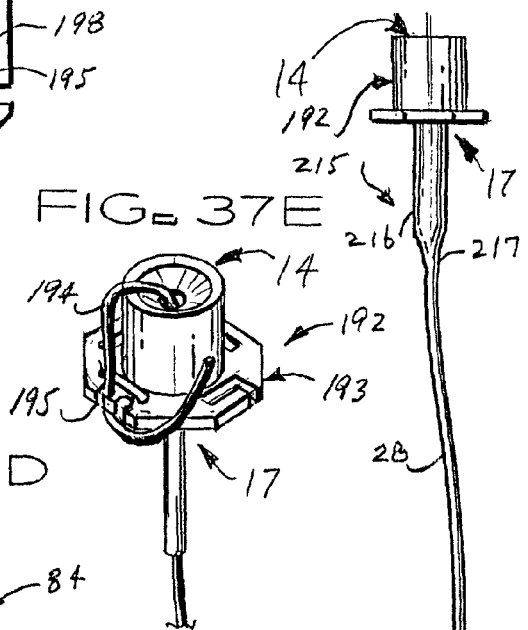
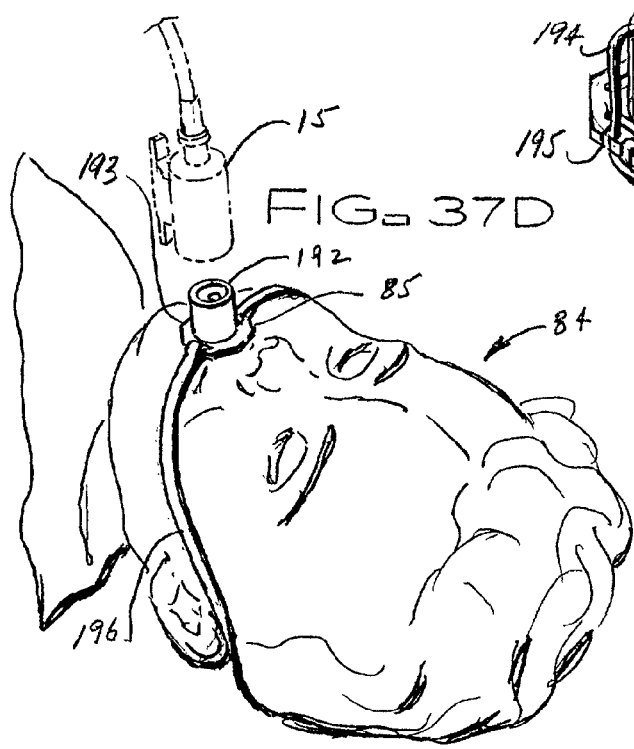
FIG. 36 PRIOR ART
FIG. 37A
FIG. 37B
FIG. 37C
FIG. 37D
FIG. 37E
FIG. 38

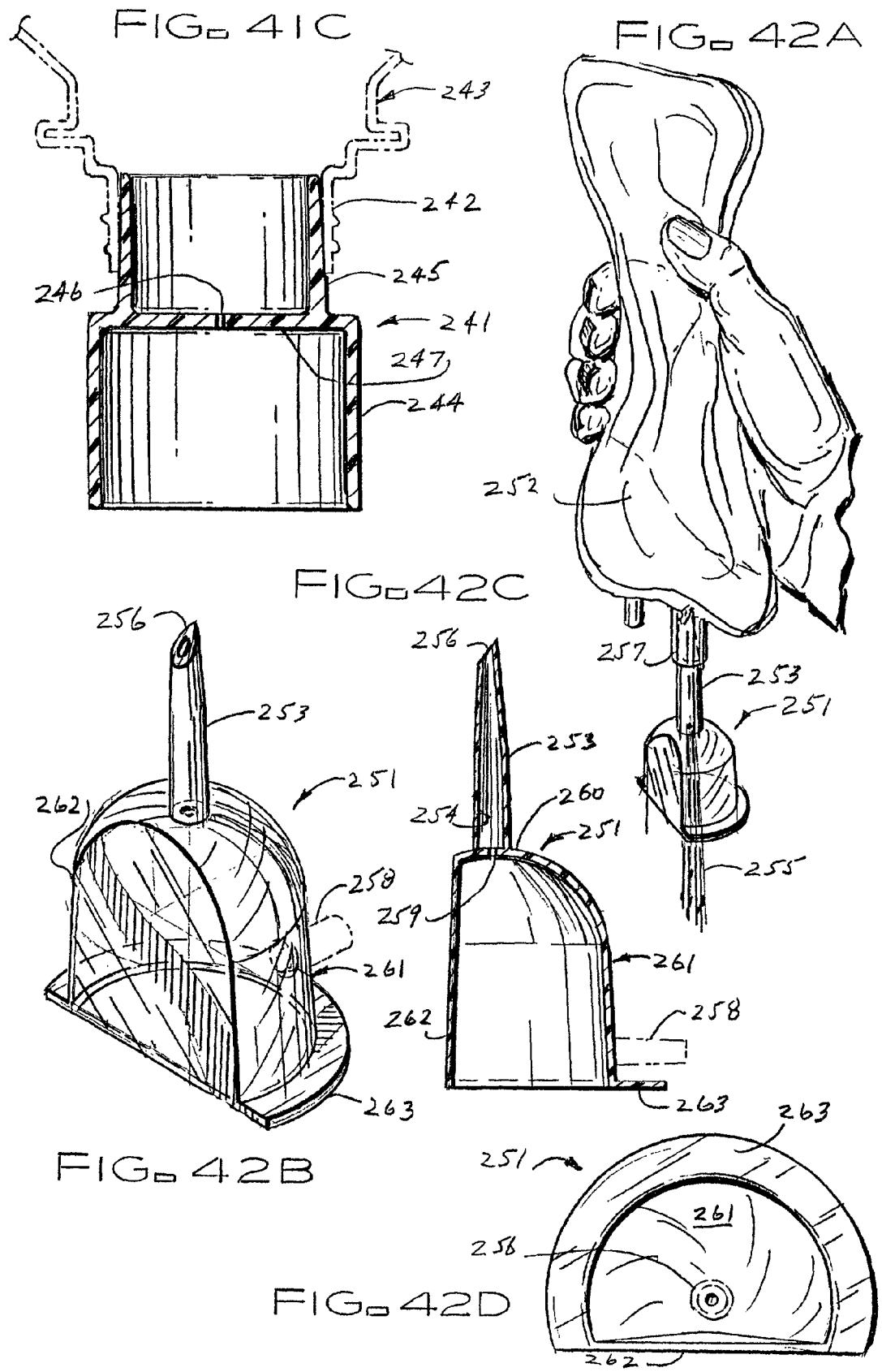

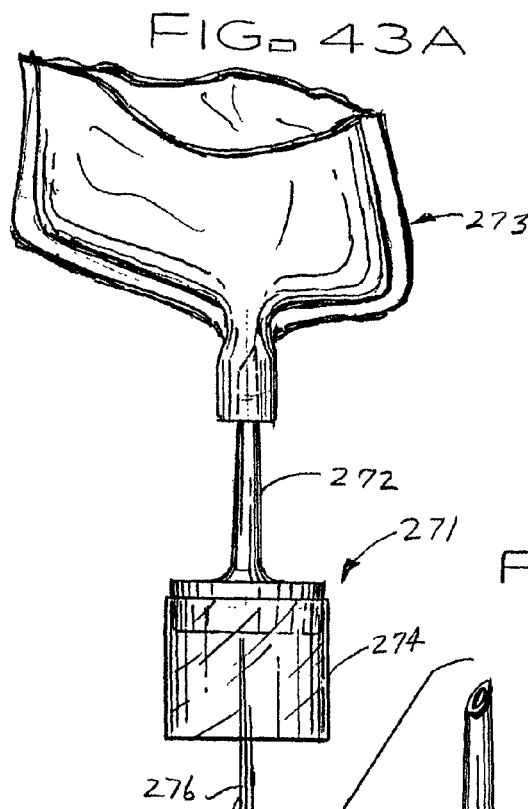
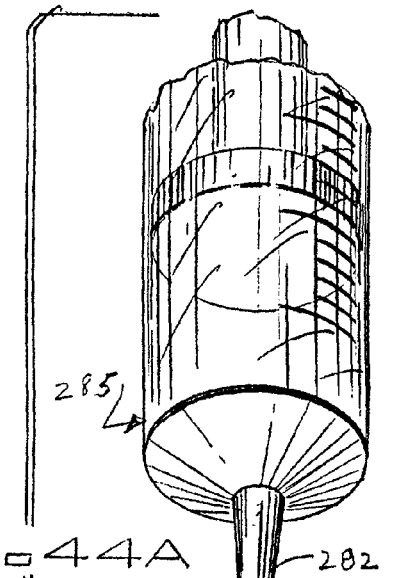
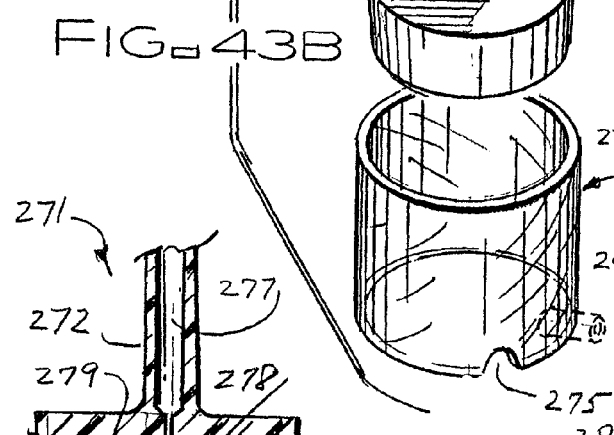
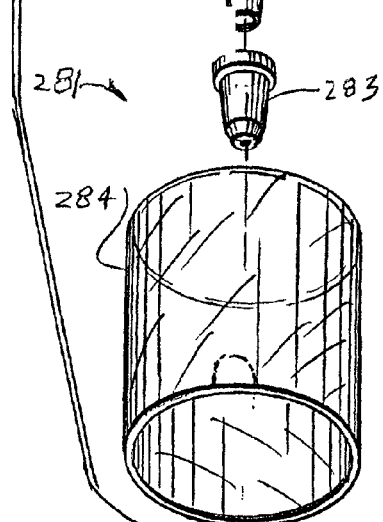
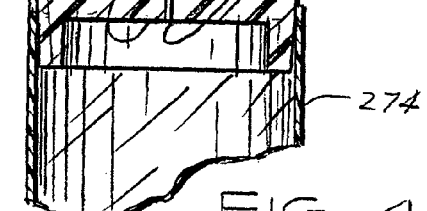

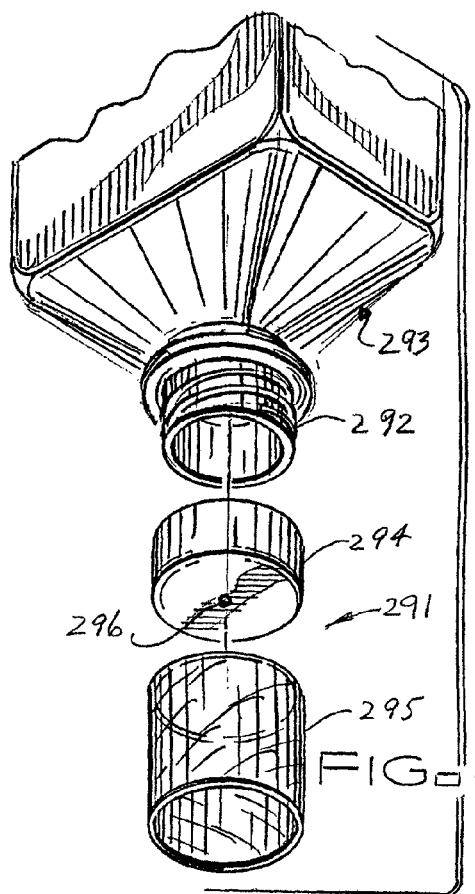
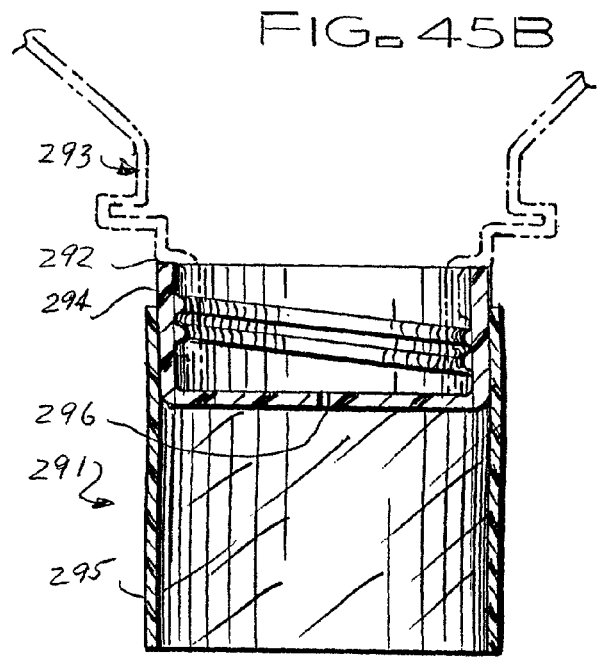
FIG. 45A
FIG. 45B
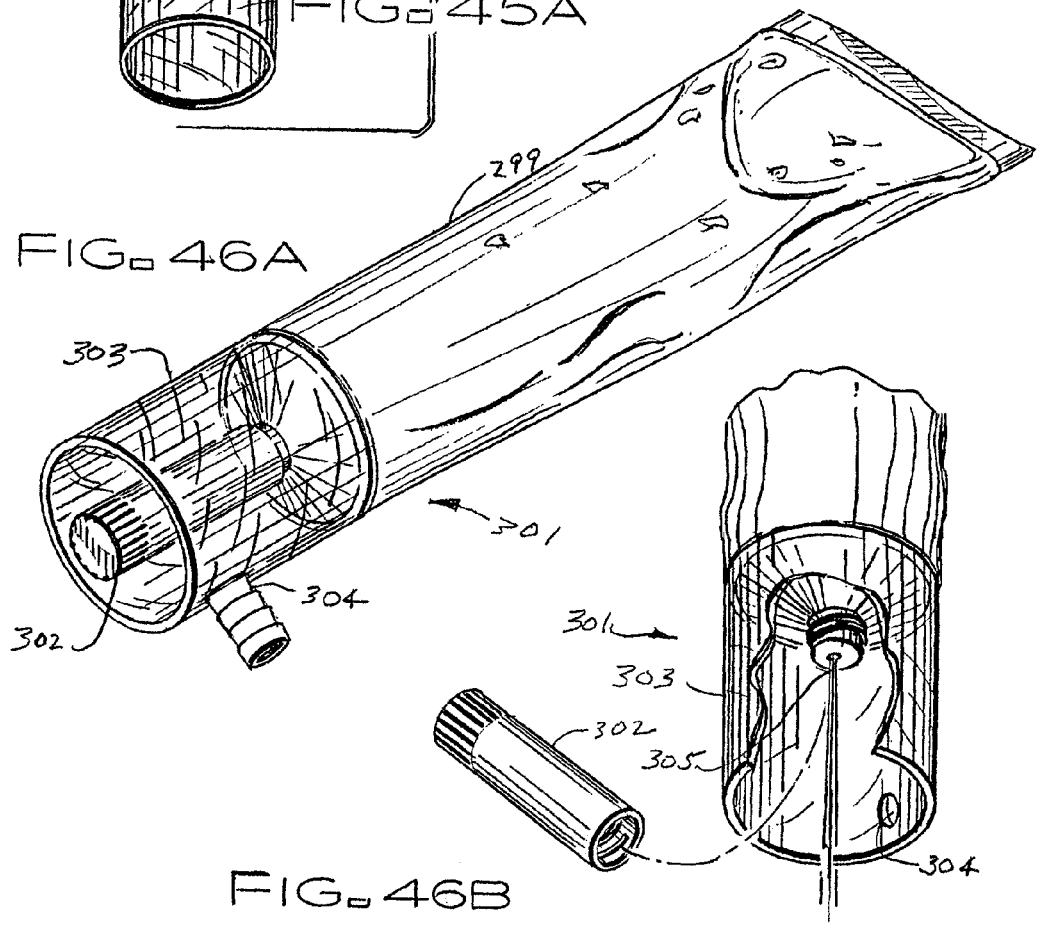
FIG. 46A
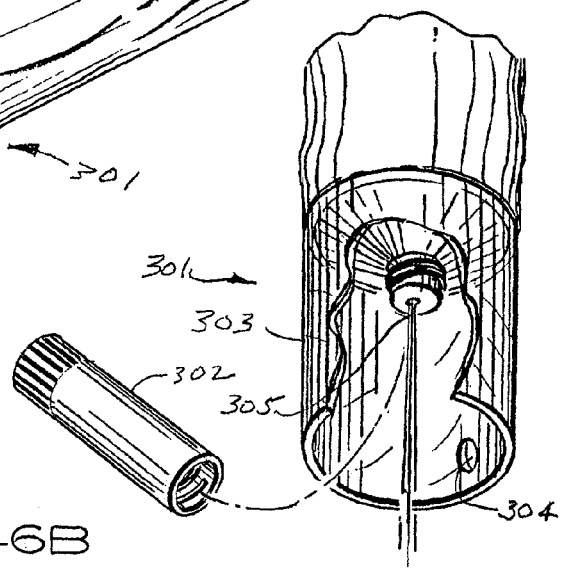
FIG. 46B

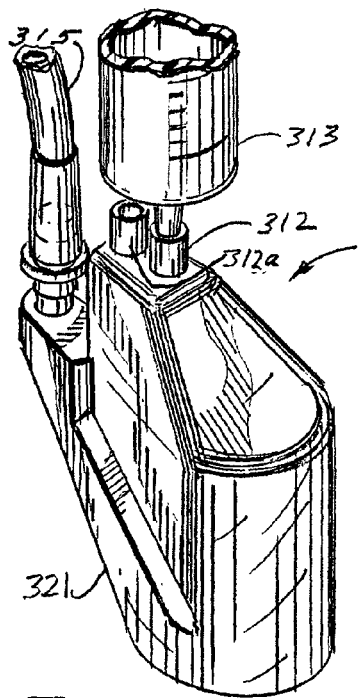
FIG. 47A
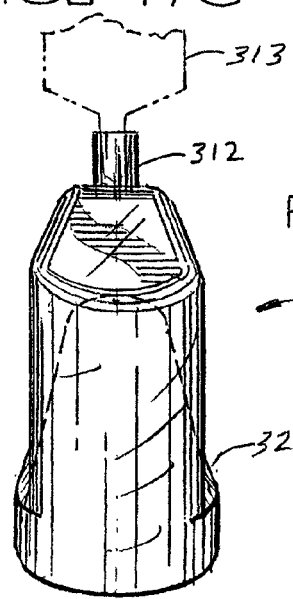
FIG. 47C
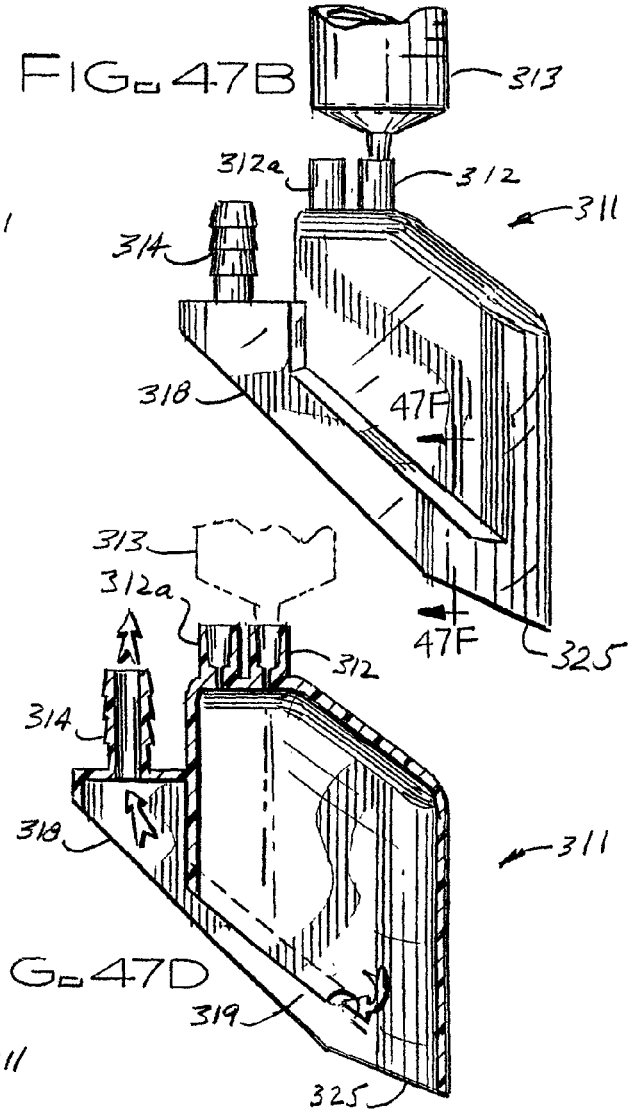
FIG. 47B
FIG. 47D
FIG. 47F
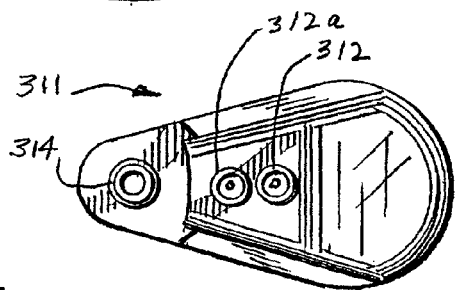
FIG. 47E
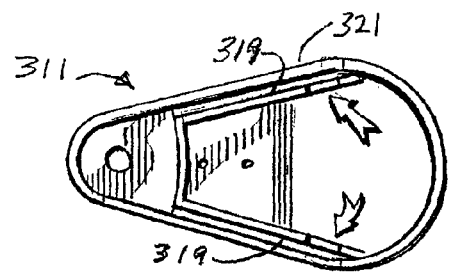
FIG. 47G

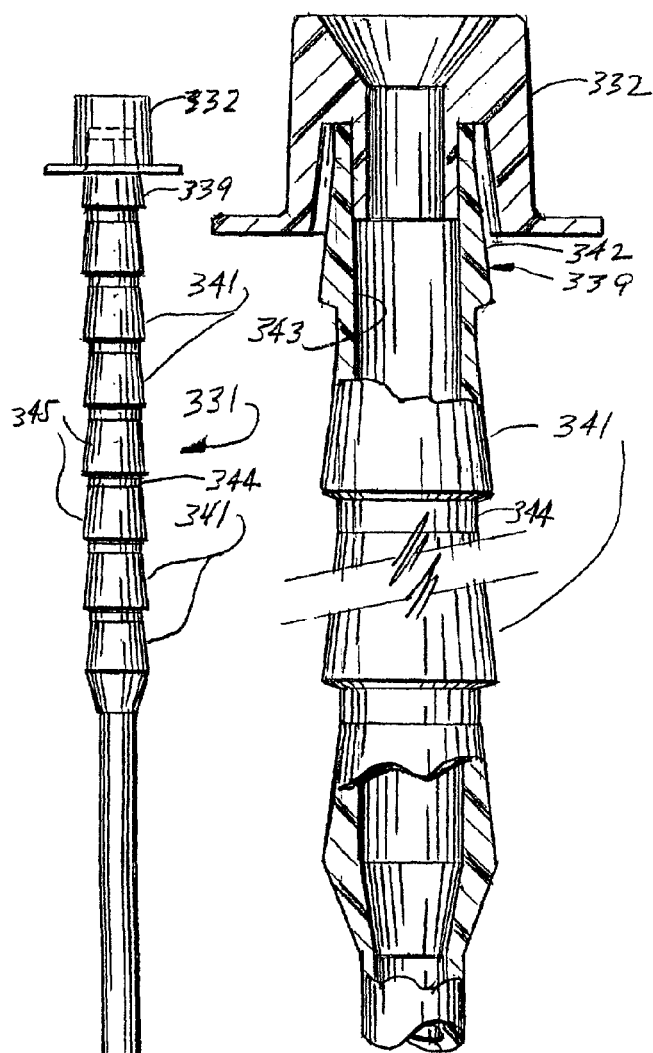
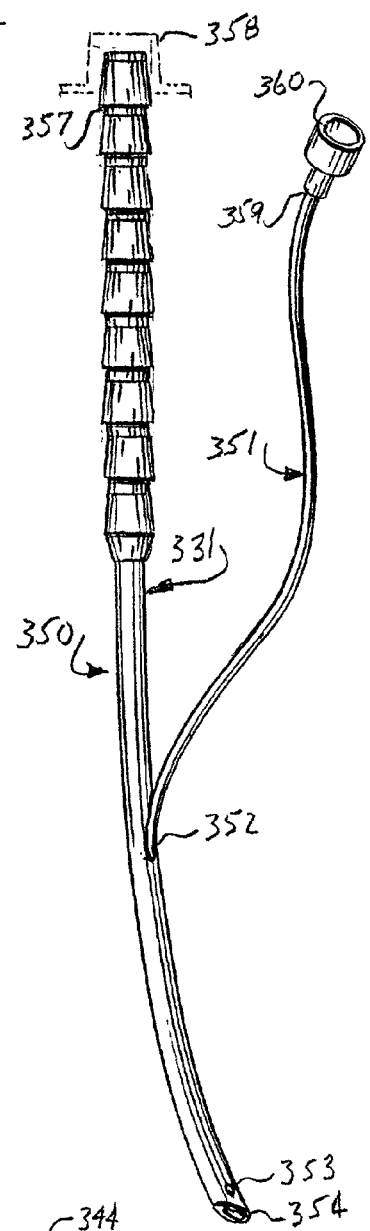
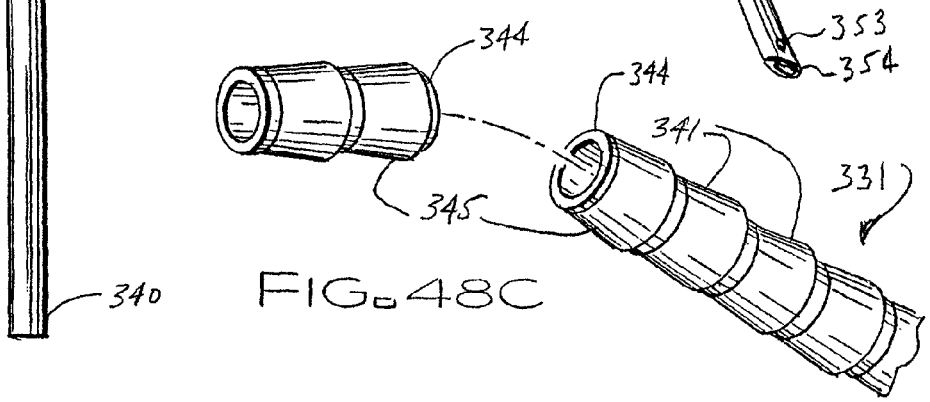
FIG. 48A
FIG. 48B
FIG. 48C
FIG. 49

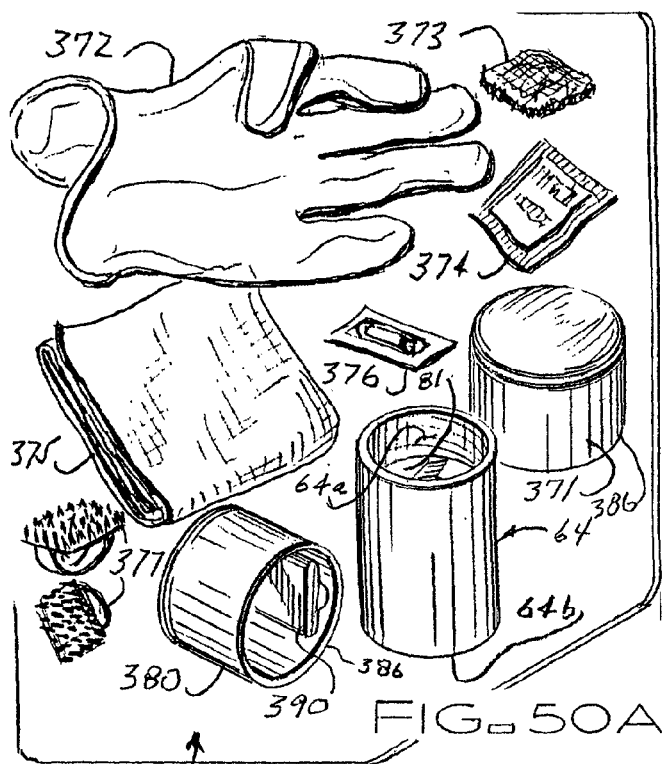
FIG. 50A
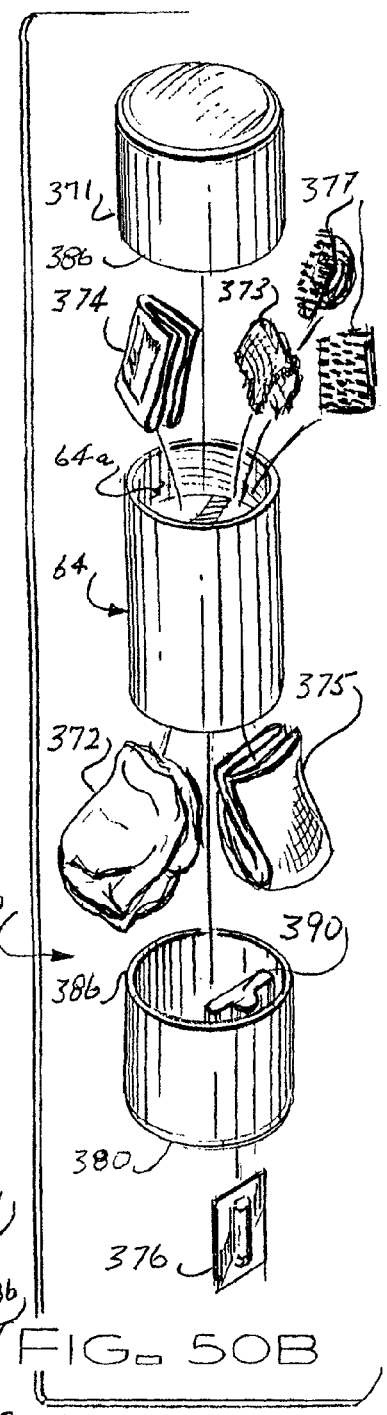
FIG. 50B
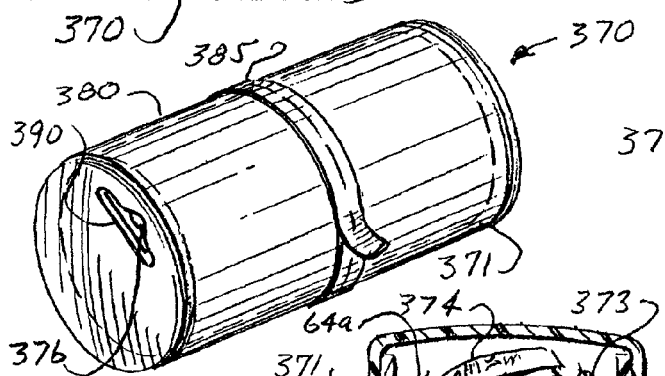
FIG. 50C
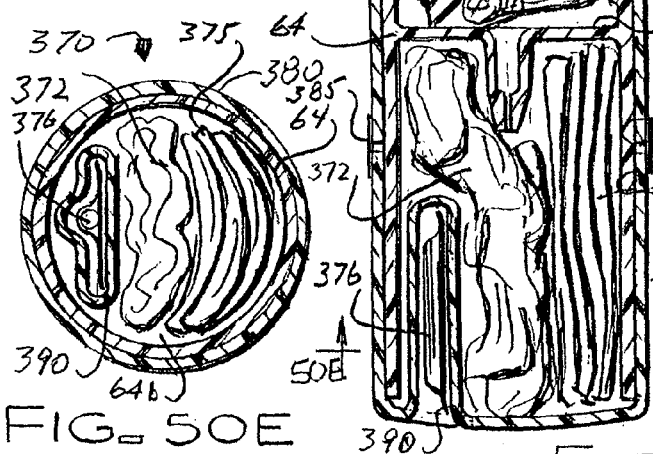
FIG. 50E
FIG. 50D

MEDICAL COMPONENT SYSTEM

CROSS-REFERENCE TO RELATED APPLICATIONS

The present application is a continuation-in-part of related application Ser. No. 09/484,666, filed Jan. 18, 2000 now abandoned, entitled "MEDICAL COMPONENT SYSTEM", which is incorporated herein by this reference, and which is not admitted to be prior art with respect to the present invention by the mention in this cross-reference section.

BACKGROUND OF THE INVENTION

This invention relates to providing a medical component system assisting more efficient and safer performance of medical procedures. More particularly, this invention concerns a multicomponent medical system comprising apparatus and methods for improved resuscitation, suction, aspiration, irrigation, lavage, monitoring, intubation, sampling, visualization and improved organization of medical devices. Typically, in the field of medicine, it is frequently necessary to use a combination of devices together to perform a single procedure or a series of related procedures. It is possible that these separate devices or components may have other similar functions for other related procedures or may have independent functions unrelated to a first procedure. These components may also be optional within the first procedure or interchangeable with other similar components. With such medical components and co-use problems, especially where suction devices are in use, there are also existing problems in areas like: sterileness; location and retrievability; intubation and resuscitation (especially with meconium problems with newborns); regulation and efficiency of suction devices (including meconium aspirators) and endotracheal adapters/tubes; specimen collection; splash shielding; syringes; monitoring; visualization and illumination; irrigation; etc.

With respect to sterileness, for example, suction and vacuum devices are commonly used to remove substances from a body surface or cavity. Because of the nature of use, these devices are often required to be sterile or as hygienically clean as possible. Many millions of dollars are spent each year in the United States to make sure that inexpensive plastic products are sterilized according to strict standards and remain sterile during transport and storage. This is generally to assure that infection is not spread from a medical device to a patient who is at higher risk of susceptibility, such as having an open wound or during a surgical procedure where internal portions of the body are unusually exposed to the external environment. Once a device is removed from its storage container, it often must remain sterile, or at least a portion such as a tip of the device must remain sterile. With great effort and expense, users of the device must maintain this sterility or hygienic standard. For example, clinicians often wear sterile gloves not only to protect themselves from infection but to maintain the sterility of the equipment they are using and placing into more sensitive regions.

For example, a vacuum tube or hose often connects from a nonsterile region (such as a wall regulator) to a sterile region (such as a surgical field). This tubing is often six to twelve feet in length and 3/8" to 1/2" in diameter; and a proximal end is often connected to a vacuum source or to a wall regulator and the distal end is placed in a field of use. Because the floor is not a hygienic surface, these devices are often placed on tables or trays above the ground, for safety and easy access. Because the weight of the remaining tubing is often substantial, particularly in relation to its end portion, the distal end is often pulled by the force of gravity or the elastic force of the tubing off a flat surface, interfering with its sterileness.

A similar problem is encountered in the organization of medical devices, not only in relation to the purpose of sterility but for the improved preparedness of a medical device. By having devices in easily recognizable and therefore retrievable locations, the efficiency of a medical procedure can be enhanced. Because of the weight of the vacuum tubing used in the above example, the devices often slide or move from desirable locations to undesirable ones in an often unpredictable way. Even if the device remains in a sterile field it may be in a place that is unanticipated or difficult to access. Often the procedure has no sterility requirements but requires speed and efficiency such as in a portion of the resuscitation of a critically ill patient. In such a case, where many things are occurring in a short time span and the consequences of success or failure are truly life or death matters, it is of utmost importance to maintain as much order as possible for efficiency and success. Often one uses a single device and then must put it down to tend to another task. Then it may be desirable to reuse the same first device. If the first device must remain sterile, then putting it down may contaminate the device and/or the device it is connected to.

Numerous devices or techniques are used to maintain medical devices, and specifically vacuum devices such as a vacuum hose or a suction catheter, in a sterile or desirable location. One technique is to avoid putting down the suction tube and continuously hold it until its use is completed. This technique obviously limits the dexterity remaining of the user's hands, which must constantly hold a device while possibly attending to other tasks. Another technique is to put down the device; and if the device is contaminated or lost, for example, to use a new one. This adds to the amount of equipment used, to the time to locate and prepare the new equipment, and to the total costs of using such excess equipment. Sometimes, a distal end of a tubing is placed in a pocket, such as one formed with the sterile patient draping in an operating room, with the frictional force of a tube hanging over the pocket keeping the device in place. Unfortunately, there are not sterile pockets located in all locations where they would be desirable. In addition, when the distal end is needed, or a device attached to the distal end is needed, the device must be retrieved from the depth of the pocket, and if one is to pull on the exposed tubing, then the device on the distal end of the tubing within the pocket may be pulled off and disconnected from the tubing by the frictional forces of the restraining pocket. Such "fishing out" of the distal end of a vacuum tubing is time-consuming and cumbersome enough without having to additionally retrieve and orient and attach a disconnected medical device within the pocket.

With respect to prior attempts to solve such retrievability and sterileness problems, clamps have been designed that affix to the side of a fixture and provide an open ring or clamp for a hose to fit into. For example, dentists have open rings attached to their assemblies into which a hose can slip. The disadvantages of these gripping devices is that they are in fixed locations. Similar to the pockets described above, they are limited by their location and availability. Their location may be in an awkward location, i.e., that is difficult to access. For example, if a surgeon needs to reach across an open body cavity to reach for an attachment, that is a location difficult to access. Such gripping devices are separate from the medical devices and do not travel with the medical device and the location of stabilizing the medical device is limited by the location of the fixed-location gripping device. As fixed devices, they are more likely to be nondisposable or frequently used or reused. If sterility is required, these fixed devices may be difficult to maintain in an hygienic condition.

In the prior art, for example, devices such as pens and beepers have restraining devices such as clips that allow these devices to be attached to pockets or belts. But these gripping devices may not be of material that is easily sterilizable and, since they were not intended to attach to medical devices, they lack the correct dimensions, for example, to be applied to suction tubing. These clips, even if they could be applied to suction tubing, do not have specialized internal retaining surfaces having the capability of accommodating a variety of tubing sizes of certain medical standards, such as an 8 Fr, and such variety of dimension-accepting capability is important in the medical field. A single vacuum hose, for example, is designed to have the potential to connect to a variety of suction catheters with flexible tubing of a variety of dimension. A 'clip' that is appropriate for an 8 Fr diameter tubing, could be very tight for a 14 Fr tubing. It may not accept the larger tubing and would therefore not perform its desired gripping function, or it may grip it in too tightly, causing too great a compression on the tubing; and that may damage its shape and cause a dangerous kinking of the tubing or a constriction or an irregularity making it dangerous to use. For example, if the tube has a sharp kink with a sharp narrowed outer diameter, that might cause a dangerous scratching when inserted into the nasal passages.

Another technique to restrain a suction tube device, for example, might be to put a weighty object on the distal end of the vacuum tubing or on a device attached distally to this vacuum tubing. The problems with such a technique include the possibility that the tubing and or the device may become hidden underneath the weighty object; or the weight of the weighty object may kink or deform a suction tube; or, if the weight is placed over a distally attached device, this device may remain fixed, but the gravitational or elastic forces of the tubing may pull away from this stationary device and cause a disconnection. Additionally, the suction tube may undesirably fall onto the floor, or this disconnection may cause other potentially dangerous situations, as in the example of a resuscitation requiring tools and devices and where procedures must be done as swiftly as possible.

Yet another similar problem may occur when the flexible tubing described above is unrestrained. Under such conditions, the free end may be under limited control due to the elastic and gravitational forces of the tubing that cause it to move when unrestrained. This might cause detrimental effects, even trauma, as by leaving a catheter next to a patient's head. For example, if the catheter were left unrestrained next to an unconscious patient during a resuscitation before the patients eyes were taped closed, it might move and rub over a patient's cornea causing an injurious and painful consequence on an already debilitated patient. So better devices and techniques for device and tubing restraint are needed.

Turning now to prior art problems with intubation and resuscitation, the medical procedure of intubating a patient is frequently necessary to resuscitate a patient who is in distress. This procedure involves many devices which must work together in an efficient manner to save time and to allow the users to concentrate on the condition of their patient and not on the condition of their medical devices. Resuscitation of a newborn with meconium is one subset of those persons that are intubated for a resuscitation procedure. The resuscitation of a newborn child with meconium will be described, as it is a good example of the needs for improvements in these areas.

Meconium is fecal matter that an infant expels in utero. It is one of the thickest, most tenacious and viscous matters of the human body. During the first few seconds of life, a child with meconium in its trachea may need to be intubated by a clinician to remove the meconium to prevent a physical obstruction of this matter in the trachea. This is done to prevent asphyxiation and to prevent the deposition of this matter in the lower respiratory tract of the newborn, which might result in a syndrome similar to a chemical pneumonitis called meconium aspiration syndrome. Such a situation is one of the few instances in which an endotracheal tube is inserted into the trachea of a patient for the purpose of aspiration rather than ventilation, the usual objective of endotracheal intubation. The procedure of aspirating meconium must be done quickly as the longer the procedure takes, the more likely that the newborn patient might develop bradycardia and secondary acidosis leading to a downward-spiraling course in which the patient is more and more difficult to reverse. It is noted that once the umbilical cord is cut the newborn is deprived of its oxygen supply and cannot receive oxygen until the lungs are inflated. This action is usually desirably delayed by lack of stimulation of the newborn until after the many steps of intubation and aspiration are accomplished by the resuscitation team. It is therefore of the utmost importance that all steps are taken to reduce the time for the procedure and to increase the likelihood of a swift and successful procedure while also minimizing the risks to the patient that such an important procedure can cause. Improved preparation and improved organization of the devices prior to, during and after the procedure are all means by which the risks to the patient can be controlled—risks that are independent of the technical skills of the clinician. After the resuscitation phase, if the resuscitation is successful, the newborn patient must be stabilized and certain routine, although necessary, steps must be taken. For example, a critical patient may need to be reintubated for the purpose of ventilation, or ventilated with a resuscitation bag and mask; and other clinical assessments of the patient may be taken at that time, such as assessment of muscle tone or pupillary function. Most of these procedural elements are not unique to newborn patients, and can be generalized to use in adult patients. Although due to many differences in size and physiology, these procedures in newborns and pediatrics require special dimensions or techniques that may be unique.

With respect to regulation and efficiency of suction devices (including meconium aspirators) and endotracheal adapters/tubes, there are many problems not solved and often not even addressed by the prior art. It is common in the field of medicine to use suction devices to remove gases, liquids, semi-solids and solid material from a cavity or surface of a body. These devices often have a valve that allows regulating the suction force applied at the opening at the patient end of the device. Most suction sources, such as wall units or portable ambulance units of vacuum are now regulated to be at a constant force using a machine source and a vacuum regulator. The regulator determines the level of suction at the source of suction. Usually it is desired to have an ability to regulate this constant source, since, for example, it is difficult and undesirable to suction while advancing within a body cavity. One usually suctions while withdrawing. In order to control the vacuum at the distal patient end of the device, suction control valves have been developed to regulate this flow at a point closer to the patient than the source regulating unit. Suction devices require much dexterity to operate in the field of medicine and therefore they are generally hand-held units that attach to flexible vacuum hosing. Sometimes the hand-held suction devices are of disposable plastic, but they may also be of metal. In the United States, this material is preferably an FDA class VI material and other countries will have their own similar material specifications for biocompatibility of plastics and other materials. Frequently the distal suction regulatory valve for such unit is on the wand of the hand-held suction device. Such device in its simple form is a single tube interrupted by a suction regulation means. In intubation, it is necessary to suction a patient's oropharynx to clear the area above the vocal cords, so that the vocal cords can be visualized; thus one can properly intubate a patient using the vocal cords as a visible landmark.

With respect to meconium aspirators, these devices are not always used, as only 10% of newborns have meconium and of these, not all are intubated. So meconium aspirators are not always in use. Sometimes, depending on the design of the device used, they are interchanged with a suction catheter coming off of the same hose. When not in use, these devices can often get lost under the warming blanket of a baby or be pulled off a warming table, by the weight or elastic force of a vacuum hose, onto the floor. If this occurs, the procedure would be delayed and equipment may need to be replaced. Since any procedure in which a meconium aspirator is used involves a patient that is being resuscitated, any delay can be extremely detrimental to the success of the procedure and possibly to the patient. Prior art does not describe any restraining means for preventing this spatial displacement of meconium aspirators. In addition, because meconium aspirators are not used in 90% of deliveries, they are often not stocked adequately by hospital personnel. The prior art does not describe a flexible suction catheter restraint on a meconium aspirator for a simple tubular meconium aspirator with an end inlet and end outlet.

It is often desirable in designing medical devices to keep the design as simple as possible for a variety of reasons. This principle would apply to any flexible suction catheter restraints, including those on meconium aspirators. For example, because oddly placed appendages are additional projecting points, they can be points that can be potentially traumatic to a newborn if accidentally scratching a body surface. In addition, such appendages can be sharp enough to burst through a sterile package and compromise the sterility of the package.

The prior art describes a one-handed method of using a meconium aspirator with an end inlet and end outlet and a side control port, but this prior described method of using a meconium aspirator requires the operator to put the hand in an awkward position since the device is vertically attached to the endotracheal tube. The vertical positioning of the hand is awkward. Also, the side port is not in a predictable position. Since the elastic forces of the vacuum tubing that the meconium aspirator is attached to may cause the device to rotate as the generally vertical connection is made, the side port may be in any position around the generally vertical connecting axis. Even after such awkward generally vertical connection is made, one then must locate the side port. The prior art does not describe a meconium aspirator with a less cumbersome attachment for the operator.

With respect to connecting a meconium aspirator to an endotracheal tube, the prior art describes tube connecting telescopically and frictionally with a male tapered endotracheal tube adapter. While this type of connection has an advantage of providing an easily made connection, it has disadvantages as well. For example, the point where a desirable seal is formed in the connection is unpredictable and can vary greatly with different dimensions of width, height, and angle of the outer wall of the endotracheal tube connectors provided by different manufacturers. While these endotracheal tube connectors generally conform to certain standards, even within this standard range there is the chance for a remarkable amount of variability. There is no teaching of an endotracheal tube connector port, including specifically one to be used for aspiration of the endotracheal tube, or including one to be used for meconium aspiration, that includes a system providing a repeatable point of forming a seal line with the telescopically and frictionally connected endotracheal tube connector. With a tapered design such as that described in the prior art, for a telescopic interfitting, one would not know where along the depth of the sidewall one would make a seal. Since the endotracheal tube connectors are of a small height and the depth of the inlet for the suction must be above a seal line to prevent the leakage of suction forces, this inlet must not be too high so that it is not easily occluded be a finger over the larger suction controlling inlet. It is an object and feature of the present invention to have a fixed diameter at a fixed depth rather than a tapered inner diameter forming a seal line so that one would know that, even using a variety of manufacturers' endotracheal tube connectors of various standard dimensions, one could still make a seal at a specific point on the device and therefore insure that the seal is attainable and is not compromised by a leak from the suction catheter inlet port. There is no teaching in the prior art of an endotracheal tube connector inserting into an endotracheal tube connector port, including specifically one to be used for aspiration of the endotracheal tube, or including one to be used for meconium aspiration, that has an opening in which the control feature occurs by the endotracheal tube connector forming a seal at a point proximal to a distally positioned side inlet for a suction catheter, including a seal formed by a diameter of a fixed dimension.

With respect to the areas of specimen collection and use of gloves, when using a gloved finger over a control port, the elastic glove might get sucked into an inlet port under high vacuum pressure. This is undesirable as it might be difficult to remove and therefore difficult to deactuate a suction unit, which could have dangerous results for a patient. In addition, a glove that extends into a suction inlet control port could occlude another inlet and prevent the inflow of substances. So it would be very useful to have a system for preventing such things.

In addition, as previously described, it is desirable to not only prevent malfunctioning of equipment, but also to prevent user contamination and user initiated cross-contamination. While gloves, such as commonly used latex or vinyl disposable sterile and non-sterile gloves protect a user from direct contamination, they can also be a source of cross-contamination if the gloves get infectious material on them and the user is not meticulous about the surfaces or patients that she later touches. It is therefore preferable to have devices, such as a suction catheter with a finger valve that limits the contamination of the controlling gloved finger, to prevent the dangers of indirect cross-contamination.

In addition, in meconium aspiration procedures, it is often desirable to regulate flow through the system even after the endotracheal tube has been connected. It would be desirable to have a device that could accommodate an endotracheal tube for the purpose of meconium aspiration and have a suction catheter inlet for routine suctioning and have the ability to be regulated easily with a minimal amount of manipulation and preferably involving a single finger.

Also, because meconium aspiration is a procedure which has a limited number of uses, it would be desirable to have a meconium aspiration device that could be useful for other procedures so that the product would have wider market and therefore might allow manufacturing and marketing costs to be reduced. The prior art does not describe a device configured like a meconium aspirator with the following objects and features of the present invention, firstly, for example, that it can also be used with a cap as a suction device with an actuator that reduces splashback on the controlling finger over the control valve. Nor is there described such a suction device with an enclosed specimen trap for sampling of respiratory secretions that might include, as an object and feature thereof, an inner appendage to increase the internal surface area to improve the function of the trap. Nor does prior art describe a device configured like a meconium aspirator that can also be used over a wound for efficient irrigation of the wound, and that might include the other useful features described herein for novel splash shields. Nor does the prior art describe a device for use in meconium aspiration that overcomes the limitations described above and preferably accommodates a user-determined option of using an endotracheal tube with a stylet either for intubation, either separately or in combination with the meconium aspirator device.

With respect to the regulation efficiency of suction valves, there are open and closed suction regulatory systems. In general, an open system will allow atmospheric room air into the system and a closed system will not. In its simplest form, a suction regulatory valve is a hole in the tubing than can be occluded. Occluding the regulatory hole causes a larger force to be applied to another inlet of the system. Different problems have been encountered in the development of open regulatory systems. With a control valve on the side of the device, occluding the device with a finger may cause suctioned debris to splash on the side of the controlling finger. One method of preventing this is to raise the level of the controlling aperture above the level body of the suction device. Such prior open hand-operated open suction control valves vary the pressure by opening and closing the occlusion of the controlling aperture. In general, if the device is unoccluded, air flows in and very minimal suction force is applied at the patient end. In general, if the device is partially or fully occluded, then the device is "on" and suction force is applied partially or fully to the distal end.

Unfortunately, though these designs claim to vary suction, their variable control is limited. These limitations are worsened even more now that personnel universally use gloves when operating these devices which in general reduce sensation and feedback. The useful variation in the prior art is only in the fully on and the fully off function. At the present state of the art, it is very difficult for a user to distinguish by sensing means any intermediate points of occlusion. In the intermediate levels of suction, the designs do not provide any way to repeatably and reliably regulate intermediate levels of suction. Of course one could adjust the regulating unit at the vacuum source, but that unit may be located far away from the user and would be inconvenient to change, since a procedure might have to be interrupted, etc. and such a delay in the midst a resuscitation could have severe consequences.

Actuators of different types have been developed to attach to suction wands to attempt to provide some intermediate control. Some operate by sliding over a hole or twisting with a screw-type actuator to occlude a hole. These devices, however, are more difficult to manufacture than a single piece. They are generally more expensive to produce and require moving parts that may break or malfunction, and they require a manipulation of the operator's hand to position properly on the actuator and adjust the suction to a desired level. And that level must then be confirmed by the operator—often and visually, such as looking at a dial or slide gradient. Similarly, if one would want to change the position, one must again position the hand and fingers into an active position over regulating surfaces and manipulate the fingers to effect the desired change. While these devices may be more effective than older systems in generating variable forces in incremental or repeatable ways, they have the problems described above. In addition, the step of "deactuating" a suction device may require instantaneous attention which might be slowed by the process of changing the position of the actuator. In addition, actuators might mistakenly be left in an "on" position which might cause traumatic results if the suction wand were applied to a fragile body surface in a careless fashion. In fact, even when carefully controlled, applying a suction using such actuators, particularly a full suction, can cause problems.

This problem of applying a closed vacuum system to a fragile surface has been addressed by few. One problem of significant concern is what happens when the suction device comes against a body surface and the body surface is sucked into the suction device aperture. If there is no regulatory suction control valve or if this control valve is fully activated, then the device becomes a closed vacuum system. As body tissue is generally more fragile than medical equipment, the weakest portion of the system, the body surface, is sucked into the suction device. Removing the device may cause tearing of the body surface, which may fragment critical body parts or blood vessels with resulting organ injury or hemorrhage. It is a standard practice for suction catheters produced now to have "eyes" at their tips. These apertures are generally located with the side wall of the device at the suction catheter or suction tube tip at the patient end. The Poole tip large number of such holes is to prevent this traumatic suctioning from occurring. Others have addressed this problem at the level of the tip, but these devices are not conducive for suctioning in all body areas, nor are they used frequently. Even under optimal conditions, these suction tip devices, including flexible suction catheter tip "eyes", may become occluded. For example when suctioning a narrow space such as the nasal passages of a newborn, a suction catheter tip may have the side openings against the wall of the nasal cavity, and therefore become ineffective. If the tip opening were to get occluded while a fully 'on' suction force were applied, then there would be no safety relief mechanism. While this full force of suction can be dangerous, sometimes it is, however, desired. An analogous situation outside the medical field is that of using a household vacuum cleaner. Sometimes you need a full vacuum force to remove a piece of debris clinging to a rug. However usually you do not want a full complete vacuum force applied because this would suck the rug into the vacuum hose tip and make it difficult to slide and maneuver. It might even pull the rug from its position on the floor and might damage the rug fibers.

There has been described in the art a hand held suction valve with an aperture elevated above the level of the suction body. This device offers the value of having relief mechanism located somewhere other than the device tip and in the body of the hand wand that doesn't require any moving parts. Unfortunately, this device still only provides the on/off repeatable regulation of the prior art and does not teach a variable repeatable incremental regulation. In addition there is no teaching in the prior art to accommodate the need for higher levels of full suction. The vacuum relief mechanism would always be on. Even if one were to modify the device by possibly occluding all ports for the device, it could not be done simply by a single finger or without the use of an actuator. The relief valve can not be instantaneously closed by a single finger that is also controlling the main portion of the regulatory valve on the top of the device. Similarly, the relief groove is at an awkward angle in relation to the main regulatory port and could not be controlled be a single finger by itself and would require an awkward hand manipulation, or an actuator or control by an additional finger.

Another difficulty with the prior art is the lack of a simple hand held medical suction device with a simple fine regulatory mechanism that is instantaneously available without the use of moving parts. Different actuators such as slides, clamps and dials with screw-type actuators have been developed; but for more variable suction control, they have similar disadvantages. Again, while the prior art inventors may describe a device with some variation, they do not show how this regulation can be done in a repeatable incremental way nor with fine control over the final portion of occlusion. If one wanted to do variable suctioning that is intermediate between the on and off positions, it can only be done haphazardly without a fine tuning mechanism, or only by one with extraordinary skill, leaving patients under the care of those with less experience in potential danger. The standard nursing principle of using "the lowest suction possible to achieve the desired result" is not achievable or easily achievable with the current art.

In my prior U.S. Pat. No. 5,562,077, I describe a structure for fitting an endotracheal tube adapter within a suction device and attempting to cover the suction inlet port with the adapter; however, such a system does not make an efficient and identifiable seal line proximally of the inlet port, a requirement for efficient use. So even here, improvement is needed. Additionally, I showed in that patent how to temporarily restrain such an adapter on the suction device body; however, in medical situations, as stated above, many types and sizes of devices should be restrained in handy and efficient positions. Here too, improvement is needed.

Nevertheless, to review, suction devices such as open held suction catheters, particularly hand-held surgical respiratory suction catheter devices including those with flexible tubing, including those with either a T or Y configuration: may not have any means for preventing splashing contamination of a controlling finger; may not have means for variably controlling suction pressure in a position intermediate from fully on or fully off that can be repeatably and incrementally controlled; or may require an intermediary actuator that require assembly from separate parts, are costly, cumbersome, complex, non-instantaneous and have the potential to malfunction and may be left in an undesirable actuated position; may not have a relief mechanism, or if having a relief mechanism, it does not accommodate a complete regulatory occlusion of all non-patient end regulatory ports by a single finger, including the relief mechanism, such as a relief port that is on the suction wand itself; may be unnecessarily prone to trauma; may require an awkward hand manipulation; may not have a relief portion; or may not provide a variable and repeatable incremental suction.

Now, with respect to design of endotracheal tube adapters, endotracheal tubes with endotracheal tube adapters are devices that are intended to be inserted through the oropharynx of a patient to accomplish ventilation and occasionally aspiration of a patient's lungs. The tube portion inserts into the patient's trachea. The adapter portion is outside the patient and connects to respiratory tubing or other connecting devices which usually will be promoting the ventilation of the patient. There is the occurrence of meconium aspiration in which aspiration occurs through the endotracheal tube. Typically, the endotracheal tube adapter has a top diameter which is of a standard diameter with walls tapering within a standard dimension for inserting into a female portion of another connector such as respiratory tubing. The adapter lower portion has a tapered male connector fitting into the proximal portion of an endotracheal tube.

A stylet optionally goes through the entirety of the central portion of an endotracheal adapter and inserts into the endotracheal tube giving it more rigidity and form. This assists in control and placement of the tube during intubation, i.e., the process of inserting the tube into the patient. The stylets are generally longer than the endotracheal tubes. The stylets are also flexible and the extra proximal length of the stylet is usually curved over the upper portion of the endotracheal tube. It is often necessary to secure the stylet further. This can be accomplished by securing the stylet around flanges extending from the lower portion of the outer wall of the endotracheal tube adapter if they are so designed. Such flanges serve other functions. The flanges help with visualization of the endotracheal tube when its outer surface is covered by the female end of a respiratory connector. And the flanges can act as a friction enhancing object for generating a rotational force on the device or causing an upward or downward force relative to the connector depending on whether connection or disassembly is desired.

Typically, in the prior art, the devices which have flanges which are designed to also secure a stylet have two flanges. This presents a problem since it is difficult to generate and control a twisting motion on an endotracheal adapter from above when the device is connected to other respiratory devices, since the other respiratory devices obstruct this manipulation from above. Therefore a twisting motion cannot be easily accomplished, as would be done with a jar lid, and must be accomplished generally from the side. The only possible twisting that can be done is with one flange being pushed outward while the other flange, at 180 degrees to the first, is drawn inwardly. This is a difficult manual manipulation. With respect to flanges and stylets, the flanges serves a protrusion around which the stylets are wound. The elasticity of the material of the stylets frequently causes these stylets to pop off the roughly designed flanges. The stylet might then twist within the endotracheal tube cause the distal end to be reoriented in an undesirable and potentially dangerous configuration. The released and unrestrained stylet might also be at an undesirable depth. If the stylet is too deep, it could easily cause a devastating perforation of trachea or similar harm to a patient as it would protrude beyond the protective tip of the endotracheal tube. If the stylet is too short, it would leave the distal tip of the endotracheal tube without the desired stiffness, defeating the purpose of inserting the stylet. This problem is particularly important in the use of endotracheal tubes for newborns and pediatrics where the dimensions are more critical, where stylets are more likely be necessary to be used, especially by less experienced personnel and where trauma is more likely to occur due to the smaller dimensions and often more fragile body structures. It would therefore be desirable to have a flange of an endotracheal tube that would provide a more specialized retention means for securing a stylet to prevent the limitations of prior art.

Also, because the combination of an endotracheal tube and endotracheal tube adapter is generally accomplished by a telescoping frictional means of a larger diameter device interfitting with a smaller diameter device, this connection is often unstable. The 'wobbling' of the wider device on the narrower device can cause the release of this connection and can cause a break in a vital respiratory circuit depriving a dependent patient on sustaining ventilation.

Typically, also, in the prior art, there have been problems with dead space and reduced diameters in endotracheal tubes, especially in working with newborns. In pediatric medicine and particularly in neonatology, the dimensions of the endotracheal tubes fitting into the trachea are more narrow than for adults since the tracheas are much more narrow. The industry maintains a standard outer diameter of the endotracheal tube adapter, but a reduced diameter of the conduit attaching to an endotracheal tube. It is desirable for the inner diameter of the endotracheal tubing to be maximized with the restraints of the outer diameter given that the resistance through the tube is inversely proportional to the length of the tube radius to the $4^{th}$ power. Therefore small changes in the inner diameter significantly affect the resistance in such systems. Even a minimal reduction in the diameter will cause a significant effect on the resistance. This is particularly unfortunate for premature newborns that have tiny airway diameters that are significantly affected by the slightest reduction in airway diameter. Therefore the wall thickness of the tubing is already significantly reducing the effective inner diameter. These premature babies have the lowest amount of respiratory muscle strength. Thus it would be useful to provide a means for increasing the inner dimensions of the tube or to prevent constrictions of the tube of the type causing a lower internal diameter which adversely increases resistance. Achieving these objectives will decrease both the artificial and the patient-generated forces necessary for the life sustaining exchange of gases.

The internal diameter is further limited by the insertion of the endotracheal tube adapter within the endotracheal tube itself. The connecting portion of the adapter has a wall thickness which must insert into the endotracheal tube therefore causing a constriction of this male connector within the endotracheal tube. Some tubes come with the proximal portion of the endotracheal tube having a widened entry diameter. Yet the rigid adapter remains the same. In fact, the widened opening of the tube, with an adapter fitting snugly in, leads to difficulty inserting the connector into the tube when cut at a more distal location. The narrower endotracheal tubing must now accommodate a connector which is designed to fit into a larger opening. The tube must be expanded by the insertion of the connector.

Given that it is more difficult to put a relatively large male connector into an endotracheal tube requiring expansion of the tube, a larger force is required to accomplish this. This force is generally downward toward the patient that is intubated and supine. This downward force can cause dislodgement of the endotracheal tube from a desired, stable position and possibly down the bronchus of a single lung rather above the level of the corini, the bifurcation of the trachea. In fact an uncontrolled compensatory force upward against the downward insertion force may result in accidental extubation of the patient. In addition, the movement of the endotracheal tube downward could cause trauma, such as a rupture of a bronchus. Also, the delay caused by making a difficult connection can be detrimental to a patient who will have ventilation interrupted while this connection is attempted. This is particularly undesirable since a patient that is intubated in a resuscitation is by definition unstable and therefore, time delays are significant. In fact sometimes this connection is unattainable and a patient must have the endotracheal tube removed since without a connecting endotracheal tube adapter the tube is nonfunctional and dangerous. So in this scenario where a connection cannot be made between an endotracheal tube and an endotracheal tube adapter, the endotracheal tube must be removed so that ventilation can occur with a bag valve mask system. Thus it would be desirable to provide a means for decreasing the force necessary to attach a shortened endotracheal tube to an endotracheal tube adapter to prevent dislodgement of the endotracheal tube from a desirable position, and to provide a more stable means of attachment of the endotracheal tube and endotracheal adapter without increasing dead space.

The length and volume of the endotracheal tube and respiratory equipment determines the amount of physiologic dead space volume that the infant must overcome for the newborn to exchange gases with the outside environment. In the human, this dead space volume is enclosed within length of the trachea and larynx, with an exchange of gases normally occurring in the oropharynx, where gases with generated carbon dioxide are exchanged for ambient atmosphere including oxygen. Thus it would be of benefit to provide a means to reduce the amount of physiologic dead space by reducing the distance necessary between the respiratory circuitry of mechanical ventilation and the patient and by reducing the volume of gas contained within this length. Even minute changes in length and volume can have dramatic and clinically significant impact on the physical parameters of ventilation, and the ultimate outcome of these patients.

With respect to the problem of dripping in respiratory circuits, present endotracheal tube adapters typically have an upper cupped portion with a lower funneled portion forming the inner conduit for a male connector to an endotracheal tube. The funneled portion of the extension assists in the insertion of devices such as a stylet or a suction catheter through the full length of the adapter and into the endotracheal tube. As one can see from the configuration of this design, if there were any respiratory condensate dripping from above the endotracheal tube adapter, this condensate will be collected in the cupped upper portion and then funneled into the patient. If this condensation had been collecting for a significant period of time, it would be more prone to be contaminated with microorganisms and therefore their entrance into the patient could promote a pneumonia. Likewise, any secretion such a sputum that is expectorated through the endotracheal tube is likely to reenter due to the funneled nature of current endotracheal tubes, therefore thwarting the body's natural efforts to remove these products, which cause mechanical obstruction and promote deleterious infections. While it is common practice for nurses and therapists to routinely clear these secretions with intermittent suction to prevent a large accumulation of such products in the endotracheal tube or the lower respiratory tract, these procedures can only be intermittent and do not prevent the draining or reentrant actions described above. In between these suctioning procedures, the draining and reentrant actions increase the potential for deleterious effects including mechanical, hypoxia, infection, etc. Thus it would be of benefit to provide a means to prevent the draining or entrance of liquids from above the endotracheal tube adapter from entering the patient and to prevent the reentry of expelled liquids from reentering the patient.

It is also noted that the prior art does not describe efficient ways to provide feedback to the physician about the length of endotracheal tubing within the patient and beyond the view of the physician, such as visual feedback near the physician and tactile feedback near the physician. Nor does the prior art describe such feedback which is atraumatic to a patient, which is compatible with a reduced dead space connector system, which improves the efficiency of insertion or reinsertion of an endotracheal tube adaptor into an endotracheal tube, which improves the efficiency of shortening of an endotracheal tube to reduce dead space or that is compatible with the limitations of use in the small mouths and respiratory structures of premature newborns.

Another issue in the intubation process is the issue of monitoring. For example, the amount of pressure generated within the system is sometimes monitored during intubation. This is generally done by inserting a connecting component between the top of the endotracheal tube adapter and the ventilation device such as a resuscitation bag. Because this connecting piece is a separate item, it often is not used because it requires that a system be broken during ventilation. In addition, it's another piece of equipment that must be sterilized in between patient use or there is a risk of iatrogenically introducing infection. This can be cumbersome and costly. Also, in a field prehospital emergency or during transport, it may be difficult to carry numerous items; but this may be a time where tension may be highest background noise high and clinical experience the lowest. It would therefore be desirable to have a means for monitoring the respiratory system without the need to have an intermediate connector between the endotracheal tube adapter and the immediate passageway or sampling device to a detection device to increase clinical assessment.

With respect to visualization during procedures (e.g., intubations), in clinically assessing a patient or in performing a procedure, it is often necessary to illuminate the eyes or the mouth. There are many specialized devices to perform these functions. On a routine basis, this is accomplished with a standard pen light. These devices have the drawback of having a large diameter causing the body of the penlight to often obstruct the view, such as when one is looking in the small mouth of a baby. Another problem encountered in visualizing the mouth is that the tongue often obstructs the view. Commonly a spatula or tongue depressor is used in conjunction with an illuminator. Typically, one hand holds the tongue depressor and one holds the illuminator such as a penlight. In addition to visualization of the mouth, it is often necessary to perform sampling, such as when a swab is rubbed on the tonsils to obtain a culture. If one hand is used to accurately control the swab, then one must either sacrifice using a hand held illuminator or using a tongue depressor with the remaining hand. Another problem encountered in assessing patients with the available tools such as a penlight, is that when looking at a patient's eyes the circular field generated may these lights has varying intensities with the greatest intensity in the center. There is no sharp demarcation of lit and unlit regions; and it is therefore difficult to accurately assess the temporal point when illumination of a pupil elicits or fails to illicit a clinical response. It would be of benefit to provide a hand-held illuminator of the mouth that allows a user to have an unobstructed illuminated view of the posterior pharynx and, further, to provide a hand-held illuminator of the mouth that allows a user to use two hands to have an unobstructed illuminated view of the mouth and swab the tonsils. In addition, with respect to illuminators used for intubation, these items are often costly due to their limited use and the specific materials and designs used in their construction. It would therefore be desirable to have a illumination device that would have a design and construction of that would have multiple uses and be made of cheaper, preferably disposable materials. Having an inexpensive, hand-held portable illuminator that can be used in routine eye and throat examinations and can also be used if necessary in a resuscitation would be desirable. As an object and feature, preferably this device might also have indicia for resuscitation information such as medications, and preferably the device could be stored inconspicuously and handily in a shirt or coat pocket and could therefore be more readily available in any event of an emergency, rather than having to search for a more expensive, more specially designed laryngoscope with limited storage locations and availability.

With respect to irrigation problems, when a patient has a wound, it is desirable to irrigate the wound with a solution such as normal saline. Presumably the dilution effect of the irrigation will wash out bacteria and debris and prevent wound contamination, infection and scarring. The more fluid, the greater the degree of success in prevention. A higher pressure of irrigation could also help remove bacteria and debris and push out unwanted debris. Unfortunately, when using large volumes or high amounts of pressures, there is a high likelihood of contaminated fluid spreading to unwanted surfaces, including splashing onto a health care provider or drenching the patient. This is undesirable as the risk of spreading of disease is heightened and there are undesirable effects of getting a patient wet (for example, a trauma patient with multiple wounds might be hypothermic from a large amount of irrigation fluid evaporating on his body, or a child with a facial laceration might become hypothermic from the excess fluid wetting its clothing during the winter). The excess fluid will also soil laundry and require increased housekeeping services, using existing methods of irrigation. This is also an inconvenience for otherwise healthy patients. They may have to remove their clothing to prevent them from getting soaked. This may be uncomfortable for the patient in a busy emergency room; and the time necessary for the patient to disrobe would delay a doctor's or nurse's ability to treat such patient or other waiting patients more expeditiously. These disadvantages will decrease the incentive for an operator, such as a physician, to appropriately use optimal large volumes of irrigation fluid; and therefore the risk of wound complications will increase.

Some wound irrigation shields of the prior art have a circular base that prevents splashback of fluid onto the operator. However, this shield's round flat surface is non-conforming to most body surfaces that sustain lacerations, since the more commonly lacerated surfaces are on an edge or ridge or prominence rather than a flat surface (e.g., portions of arms or fingers, etc.). So use of such shields typically leaves open gaps where fluid can spray out and contaminate the nearby regions. Since the flat base surface of such devices can only be used in one plane when the base is placed with stability against the skin for support, a user is encouraged to use only the perpendicular positioned spraying orientation that the device provides, rather than angling the device in non-perpendicular orientations. Angling the spray would allow visualization from directly above—where the operator is most likely going to be looking from and where his viewpoint is more likely to be. Another problem with a generally perpendicular angle of an irrigation jet is that this configuration would tend to push wound bacteria or debris straight down and deeper into the wound. As an object and feature of my invention, angling the irrigation jet would give a horizontal vector to the forces on the bacteria and debris within the wound and this would tend to push the debris out of the wound rather than just farther into it. It would push the debris out of a wound by sometimes aiming the flow underneath the target and thus pushing it up by the upswelling of the irrigation fluid rather than jamming it farther in.

Nor does the prior art (in using such "perpendicular" splash shields) teach efficient methods of removal of large amounts of irrigating fluid. Typically, at present, workers must mop up the blood-tinged irrigation fluids with sheets and towels, with associated increased hospital wastes and costs and increased biohazard risks to hospital personnel, including risk of slipping on a wet floor, for example. A prior art device describing a wound irrigation shield with an irrigation removal system has a suction coaxially placed with the irrigation unit. That presents problems; such placement will distort the irrigation stream. In fact if the forces of the stream are small and the vacuum of the removal system is great, there may not be enough force for the stream to reach the wound. In addition, in the prior such systems, the removal outlet is high above the surface of the patient and therefore would be ineffective in suctioning fluid on a patient's body surface since it would have to have a strong vacuum to pull the irrigation fluid off the body up into the air and into the vacuum outlet. Thus it would be beneficial to provide a more efficient system and means for wound irrigation and irrigating-fluid removal.

Further objects and features of my invention are not taught in the prior art. There is no teaching of a wound splash shield device with an irrigation fluid jet that can be activated by suctioning or siphoning that provides an automatic irrigation stream that can deliver high volumes of irrigation; nor is there any teaching of a wound splash shield device with an irrigation fluid jet that can be activated by suctioning or siphoning that requires fluid to traverse a wound before reaching an outlet that provides an automatic irrigation stream that can deliver high volumes of irrigation fluid to cleanse the wound with minimal effort and also providing an effective removal means of this irrigation fluid. Nor is there teaching of this fluid, once activated, having a continual non-automatic stream powered by a continued suctioning or siphoning effect; nor is there teaching of such a device also having a flexible catheter attached to an inlet for suctioning or siphoning or such a device also being capable of accommodating a more active irrigation fluid delivery device such as a syringe to the same port or another port to enable one device to be capable of a variety of irrigation delivery techniques.

As most wounds are linear (or a combination of linear openings in the skin), the rounded lateral surfaces are generally wasted space that as shown above can actually be detrimental to optimal performance. There is no teaching in prior art of wound splash shields, as in a feature of my inventions, with a more elongated opening or base, which would be better suited for most wound surfaces to economize space and prevent the outpouring or spraying of debris and contaminated fluid. Nor is there teaching in prior art of wound splash shields with a contoured opening or base that would be better suited for most wound surfaces on body prominences to perform a better effective seal to improve the activation or operation of a suction- or siphon-controlled splash shield.

In addition, when an operator empties a syringe using the described prior art splash shield, the operator must actively detach the shield from the syringe. This active step is one more that will discourage a user that for example is in a busy emergency room, from using the optimal large volume of irrigation fluid.

Nor does the prior art give, as in a feature of my invention, a method of controllably causing a stable angled flow down a linear space. There is no teaching of a construction permitting and enhancing that an angled flow of a device can be rocked back and forth for providing an effective angular irrigation stream. Another disadvantage of a perpendicularly angled stream is that the force when in use of the plunger is pressing down directly on the skin. In general there are no lateral forces in a consistent direction that would ease the movement of the device from one region of a wound to another, particularly in a linear wound. Another drawback of the prior art is that there is no teaching of a vent or relief feature (as in my instant invention), for more safe and efficient suction of excess irrigation fluid; and there is no teaching of such a device with a suction powered removal system with a vent or relief feature that would prevent a full suction from occurring when the device's base formed a firm seal against a body surface. Such a suction force without a relief feature could pull the skin up into the device and cause damage and deformity to what might already be injured tissue.

Further, with respect to the design of improved wound irrigation shields, there are a number of standard type containers of sterile fluid (such as saline) in medicine. One of these is an "IV bag" which may contain sterile normal saline solution. The IV bags are compressible and therefore one could propel fluid through the outlet and onto a wound. One prior-art method of doing this shows a connector with an inlet end that inserts into an IV bag and an outlet end that has a "syringe tip". Such a device has already been available in the form of a connector that has a sterile needle end with variable dimensions and an outlet end with a "syringe tip". These devices suffer the lack (provided as a feature of my present invention) of a barrier to restrain splashed fluid. Such barrier are more and more generally used in medicine due to the risk of blood-borne disease such as HIV. And using connectors between such devices has numerous limitations. Assembling the devices together by the available friction fits requires time. Multiple separate devices might need to be unloaded out of sterile containers, resulting in increased time for the procedure, increased waste of packaging, increased cost of packaging and increased risk of the parts or the users breaking sterile protocols. In addition, vigilance during the procedure is required to assure that the devices do not disconnect. If such a disconnect occurred during a procedure unexpectedly, this would lead to a dangerous situation where a clinician might be exposed to a patient's bodily fluids and or where fluid might drench a patient or hospital room. This problem of disconnecting may be particularly a problem with the use of a compressible IV bag, as the act of manual compression requires a significant amount of force and might leave a user's hands shaky and unstable causing the assembled unit to be moved around quite a bit, possibly separating the unit apart.

Another limitation of the prior art is that the devices that do have splash shields have only one aperture for injection and therefore allow for only one size of jet stream. It is common to have many user preferences in wound irrigation. Some might prefer a quicker, lower-pressure higher-volume large-aperture injection and others might prefer a slower, higher-pressure lower-volume narrower-aperture injection. Prior art devices only allow for one type of injection stream through a single aperture. Or such devices can accept different IV catheter hub and tubing assemblies with different diameters to vary the pressure and flow; but this method requires additional assembly and the use of additional costly sterile packaging with disadvantages such as those described above. Others in the prior art use a single injection inlet with a complex mechanically powered water injection unit with a variable motor unit. This unit is costly and cumbersome and unlikely to be disposable. Its bulk makes it cumbersome for maneuvering on different parts of a patient's body. There are now no manually operated wound irrigation shields and injectors that have an inlet mechanism that allows for simple variation of injection flow (as in my present invention) to easily accommodate for user preferences. Such a device would gain broader acceptance and use; and it would reduce the stocking of multiple models or parts and would eliminate the need for assembly of connectors. Nor do any of these (as in my present invention for eliminating the problems set forth in this paragraph) have such a mechanism using IV spikes as connector inlets. Nor do any of these have a mechanism using an IV spike as a connector and having grooves or protrusions for stabilizing the interface between the squeeze bag or tube such as an IV bag and the shielding device. Nor do they have any means for improving the gripping means, or providing a flat surface for pivoting the injection stream. Nor do any of these have such a mechanism using a single part with an irrigation shield. Nor do any of these mechanisms have connectors that fit inside the already standardized fluid container outlets. Current wound irrigation shields fit over the fluid container outlets of the device and the increased diameter increases the visual obstruction caused by the connection. Even minor increases in diameter can be of significance for wound irrigation shields that are small relative to the size of the fluid container which may already be causing a visual obstruction.

With respect to providing more efficient syringes, it is noted that syringes are commonly used in medicine to deliver medication or medicants or fluids for medical therapies or medical procedures. They consist of a cylindrical body with a tip and plunger that expands or contracts an inner reservoir. Commonly there are markings on the side to indicate volumes associated with the size of the reservoir and the syringe has a tip that assists in the delivery of contents and assists in making connections. As these are manually operated, the devices are to a great extent limited by the dimensions of the hand. Syringes are often placed in containers and bottles with round openings. These openings likewise restrict the function and therefore the size of the barrel of the syringe being inserted. As most medical containers have screw on caps or lids for achieving a good seal or for safety, the bottles must be opened with a twisting of the hand and they are again limited in size by the limitations of the gripping size of a hand. The syringe barrels must therefore be smaller than these cap dimensions to fit within a container opening with such a cap. While one could get around this problem by pouring the containers into an open basin or bath, this is not always practical. It adds more equipment. The transfer or open storage might risk contamination of a sterile content and the contents might be sensitive to the openness if they are more prone to light sensitivity or oxidation for example. Therefore, container storage with a cap or lid, particularly a round one, does have significant advantages. Unfortunately, in a situation where the container (such as a bottle) has a narrow opening that may be limited by the volume of the bottle, one must also use a more narrow syringe. As the diameter of the barrel of a syringe narrows, the total volume that may be contained within its reservoir per unit length is decreased.

Having a compressible reservoir delivery system, including a syringe, with a relatively low volume to unit length ratio has certain advantages in some circumstances. This is a common design for use when fine control over the delivery of a substance may be required, as in a chemistry or pharmaceutical lab for example. Another example in working with human medicine is working with premature newborns in an intensive care unit. Their small size requires much smaller volumes. Delivery systems with fine control of delivery are necessary as other options have drawbacks. For example, if one wanted fine control over delivery of 5 cc. of a medication, one could dilute this medicine so there would be a larger volume and hence a longer length in the delivery system of a desired medication being delivered and therefore finer control.

Unfortunately, this additional volume may contribute to fluid overload and potentially congestive heart failure in some fluid restricted premature newborns. The prior art often has small narrow 1 cc. syringes less than a single handspan in length. If one required fine control over the instillation of 5 cc. over a short or extended time period into the IV system of a premature newborn for example, one would have to remove the fine 1 cc. syringe five times. This would have a risk of contamination of this system with bacteria or air bubbles, for example, being at least five times greater. The prior art does not describe a single hand held and operated compressible reservoir with a plunger such as a syringe with a narrow barrel for fine control over the fine delivery of the reservoir contents that can have a length that can easily be operated with control over the syringe for instillation or removal instantaneously and using a larger length and therefore a larger volume, especially a length greater than a single hand span.

Another disadvantage of prior art comes in the area of wound irrigation. It is desirable to use a large volume of fluid and fluid under pressure to irrigate a wound to remove bacteria and debris and reduce wound complications. Current art of syringes requires that one use a syringe with a limited volume multiple times to draw up irrigation fluid and then expel it. If a larger volume syringe is desired to reduce the time consuming and cumbersome steps of drawing up fluid and expelling it, the syringe diameter is limited by the size of a irrigation container opening. As previously described, resealable irrigation containers, such as bottles are preferable to open basins or baths. It is also desirable to have a single hand operated syringe for reasons also described above, including the fact that a second hand may be stabilizing other equipment such as a splash shield. Prior art limits the dimension of a single hand operated syringe used in an irrigation procedure with a resealable irrigation fluid container to be of a dimension with a barrel width narrower than the irrigation fluid container and a length less than a single hand span. Current art does not teach having a larger volume syringe for this purpose, or more specifically having a longer single hand operated syringe with a simple plunger delivery of the reservoir contents.

Another disadvantage of the prior art in the delivery of contents is the delivery of contents that require a higher pressure to deliver. Examples are fluids such as normal saline that is pushed through a small aperture under high pressure for improved irrigation results or such as high viscosity fluids, including a slurry of activated charcoal to be delivered through a tube to a patient with an overdose. As syringes are hand operated, when a hand, including a fully extended thumb and gripping fingers are extended and intended to contract to operate the syringe, it is in a less stable position than in a less than extended or contracted position. It is therefore desirable to have a syringe that reduces the instability of a hand operated syringe delivering contents under high pressure when the plunger is an extended, including fully extended position. Unfortunately, the prior art does not address this need adequately, and syringes that require high pressure often require two hands for operation to maintain stability or possibly require the device to be placed against the body for example. One attempt at addressing this concern is to have improved gripping means on the barrel of the syringe and at the end of the syringe plunger. Unfortunately, when the syringe is in a fully extended position, the system is still relatively unstable, especially when high pressure is necessary to hand operate the device. Additionally, if the syringe were of a length greater than one hand length, the syringe could not be operated by one hand and would therefore require more manipulations to operate.

Additionally with regard to gloves, they are sometimes worn to prevent the contact not only with infectious agents, but also to prevent contact with toxic or dangerous compounds. This is true not only in medicine, but in non-medical settings as well. One such "toxic" compound is a tissue adhesive by the trade name Dermabond™. This is the biocompatible or equivalent of the product, cyanoacrylate, commonly known as "SuperGlue". This substance can be dangerous or toxic to humans in certain situations such as when it causes the unwanted adherence of two skin surfaces. Unfortunately when bringing together two items with these substances, one often inadvertently bonds two other surfaces, such as the surface of the skin. Specifically, in the procedure of adhering two approximated wound edges with Dermabond, the medical personnel often get the Dermabond on the fingers undesirably when applying to wound, as the wound must be approximated with the fingers and the glue is often non-viscous. Bonding of the fingers causes delays in trying to remove it or causes an unsightly and undesirable film on the finger surfaces for example. To prevent this, personnel often wear gloves. Gloves are also necessary as medical personnel must observe universal precautions with even minor wounds. Unfortunately, the commonly used latex gloves often bond to themselves preventing manipulation. They also bond to the skin of the patient. Not only is this inconvenient to detach the medical personnel from the patient, but the distraction force required to remove the glove from the skin surface can cause a dehiscence of the recently approximated wound.

One solution has been the development of wound forceps by Bionix Corp. These bring the skin surfaces together without direct contact of the user or their gloves with skin surface. Unfortunately, these devices are bulky relative to most wounds, they restrict the user to only certain dimensions of wound approximation achieved by the forceps dimensions, they are specifically designed for flat surfaces and do not work well on the rounded, sharper contours and body prominences that are more wound prone and more commonly lacerated. They are not designed for wound closure by distraction of skin surfaces, such as the linear ends of a wound, which often provides better approximation than medially directed pressure.

OBJECTS OF THE INVENTION

A primary object of the present invention is to fulfill the above-mentioned needs by the provision of a medical component system assisting more efficient and safer performance of medical procedures. Further primary objects of this invention are to provide a multicomponent medical system comprising apparatus and methods for improved resuscitation, suction, aspiration, irrigation, lavage, monitoring, intubation, sampling, visualization and improved organization of medical devices. A further primary object of the present invention is to provide such a medical component system which is efficient, inexpensive, and handy. Other objects of this invention will become apparent with reference to the following invention descriptions.

SUMMARY OF THE INVENTION

According to a preferred embodiment of the present invention, this invention provides a medical system for use with separate user-hand-held-type medical components usable by a user in related medical procedures, comprising: at least one first such separate user-hand-held-type medical component located in a first position; restraint means on such first separate medical component for temporarily restraining, without substantial interference with normal use of such first separate medical component, at least one second such separate user-hand-held-type medical component in a second position adjacent such first position for ready availability for potential use by the user, wherein such restraint means is structured and arranged for restraining multiple kinds of user-hand-held-types of equipment. And it provides variations and additions to such system.

Also, in accordance with a preferred embodiment of this invention, it provides a medical system for regulating suction, comprising: a user-hand-held-type medical component structured and arranged for use in a suction system and comprising at least one external aperture means for regulating suction; wherein such aperture means comprises single-finger-operable valve means for repeatable incremental user control of suction-vacuum variation in such suction system, and tactile feedback means for amplifying tactile feedback to a user to enhance distinguishing of control increments. And it provides additions and variations to such system.

Further, according to a preferred embodiment thereof, this invention provides a medical system for use with user-hand-held-type medical components usable by a user in related medical procedures, comprising a first said user-hand-held-type medical component comprising: first outlet means for attaching a vacuum source; a body means for transporting air from inside said body means to said first outlet means; first inlet means for attaching a suction catheter to said body means; second inlet means for providing assistance in regulating air flow into said first inlet means; and third inlet means for attaching a second user-hand-held-type medical component selected from the group consisting of an endotracheal tube adapter, a specimen trap, a cap means for temporary sealing of said third inlet means. And it also provides such a system wherein: said body means comprises a round cylinder portion having a central axis; and said third inlet means is structured and arranged for attaching the second user-hand-held medical component with said round cylinder portion in line with said central axis. And it also provides such a system wherein: said body means is, internally, substantially cylindrical in shape; and said body means comprises a circumferential internal seal means for making a seal with an endotracheal tube adapter when said adapter may be attached in said third inlet means; wherein said seal means is located proximally from said first inlet means. And it provides variations thereof.

Even further, this invention provides, according to a preferred embodiment thereof an endotracheal tube adapter comprising, in combination: an adapter body constructed and arranged, at the proximal end of such body, for insertion into a distal female connector of a medical device in such manner as to connect a proximal air port of such adapter to a distal air port of such medical device; on such adapter body, an outwardly-extending flange comprising a substantially fall external perimeter constructed and arranged for equal user-grippability from any direction. And it provides variations thereof.

Moreover, this invention provides, according to a preferred embodiment thereof, an endotracheal tube comprising: at a proximal portion of such endotracheal tube, an enlarged-diameter means for providing tactile feedback to a user about the distance of the intubation insertion point from the user. And it further provides variations thereof.

Even additionally, there is provided by this invention in accordance with a preferred embodiment thereof, a splash shield system for irrigation of a patient's wound and suction removal of excess irrigation fluid, comprising: a body means for fluid containment, wherein such body means has a maximum height dimension at a non-peripheral portion and a minimum height dimension at peripheral portions, and wherein a splash portion of the space within such body means, adjacent an irrigation target area, is essentially directly below such non-peripheral portion and along a vertical axis through such maximum height dimension; and an input means, for input of irrigation fluid into such splash portion of such body means, located at a height position intermediate of such maximum height dimension and such minimum height dimension. Also, it provides variations thereof.

Yet moreover, this invention provides, according to a preferred embodiment thereof, a splash shield system comprising: a transparent body means for assisting protecting a user from contact with irrigation fluid directed at a patient's wound; an irrigation-source connection means for connecting such body means, at a first end of such body means, to a source of irrigation fluid; wherein such body means comprises essentially a hollow round cylinder having essentially a hollow round-cylindrical inner hollow; and wherein such hollow round cylinder, at a second end of such body means, is open to such hollow and is constructed and arranged for contact with a patient's skin in such manner as to protect the user from contact with the irrigation fluid. It also provides variations thereof.

Even yet further, this invention provides a splash shield system comprising: a transparent body means, having a substantially-open bottom end, for assisting protecting a user from contact with irrigation fluid directed at a patient's wound; an irrigation-source connection means, unitary with such body means, for connecting such body means, at an upper portion of such body means, to a source of irrigation fluid; wherein such irrigation-source connection means comprises an IV-spike connector. And it provides variations thereof.

Even additionally, this invention provides a syringe system comprising: syringe barrel means for holding a reservoir of fluid; syringe-tip dispensing means at a dispensing end of such syringe barrel means for dispensing a stream of the fluid; and syringe plunger means for forcing the fluid in such barrel means to be dispensed through such syringe-tip dispensing means as such syringe plunger means is moved in such syringe barrel means toward such dispensing end; wherein such syringe plunger means comprises a handle means, operable by a single hand of the user having a single-hand span, for gripping and moving of such syringe plunger means in such syringe barrel means toward such dispensing end; and wherein such handle means comprises spaced multiple gripping-point means for gripping operation by the single hand; and wherein such syringe barrel means is substantially longer than the single-hand span; and wherein such syringe system is structured and arranged for the dispensing of user-chosen variable fluid volumes depending upon which ones of such spaced multiple gripping means are successively gripped by the single hand and the number of times such syringe plunger means is moved toward such dispensing end, by the single hand, within such syringe barrel means. And it provides variations thereof.

Also, this invention provides a cough shield system comprising: a cough shield means for supplying a cough shield to a component of medical equipment; such cough shield means comprising a thin, transparent, portion of a plastic material; such cough shield means comprising at least one attachment means for attaching at least one selected location of such portion to another selected location of such portion; and such cough shield means comprising at least one connection means for connecting at least one selected location of such portion to such component; wherein such cough shield means is constructed and arranged in such manner that use of such attachment means and such connection means will result in the supplying of a cough shield to such component. And it provides variations.

And it also provides a medical component comprising: first outlet means for attaching a vacuum source; a body means for transporting air from inside such body means to such first outlet means; first inlet means for attaching a suction catheter to such body means; and second inlet means for providing assistance in regulating air flow into such first inlet means; wherein such body means comprises a round cylinder portion having a central axis and such first and second inlet means are disposed along such central axis. And variations are also provided.

Further, according to a preferred embodiment thereof, this invention provides a kit comprising: at least one sealed package of fast-acting glue; and at least one glue-resistant glove; wherein said at least one glue-resistant glove is structured and arranged to resist sticking to such fast-acting glue.

BRIEF DESCRIPTION OF THE DRAWINGS

FIG. 2A is a perspective view illustrating a prior art vacuum device connected at its proximal end by a coupler to a vacuum source line and connected at its distal end to a medical device like an endotracheal tube and adapter and having a vacuum control port.

FIG. 2B is a perspective view illustrating a prior art vacuum device connected at its proximal end directly to a vacuum source line and connected at its distal end to a medical device like a catheter and having a vacuum control port.

FIG. 2C1 is a perspective view illustrating another prior art vacuum device connected at its proximal end directly to a vacuum source line and connected at its distal end to a medical device like a catheter and having a vacuum control port and including a detached soft cap for closing the port without supposedly without finger contamination.

FIG. 2C2 is a perspective view of the prior art device of FIG. 2C1 showing air flow with the soft cap attached.

FIG. 2C3 is a perspective view of the prior art device of FIG. 2C1 showing a finger pressing the soft cap to close the vacuum control port.

FIG. 2C4 is a partial side view of the prior art device of FIG. 2C1 showing how, with the vacuum control port on a bottom side, the user's finger may be contaminated.

FIG. 3E is a side sectional view of the medical suction device of FIG. 3A and further showing use of a finger for fully closing a flow control port according to the present invention.

FIG. 4A is a rear perspective view illustrating an alternate preferred embodiment of a medical suction device according to the present invention.

FIG. 4B is a side sectional view of the medical suction device of FIG. 4A.

FIG. 4C is a sectional view through the section 4C-4C of FIG. 4A.

FIG. 5A is a partial side elevation view illustrating another alternate preferred embodiment of a medical suction device according to the present invention.

FIG. 5B is a top plan view of the embodiment of FIG. 5A.

FIG. 5C is a sectional view through the section 5C-5C of FIG. 5A.

FIG. 6 is a partial side elevation view illustrating an alternate preferred construction for the inlet end of preferred medical suction devices.

FIG. 7A is a perspective view of a medical suction device according to the present invention showing another preferred construction for the inlet end and connected to an endotracheal tube adapter.

FIG. 7B is a partial perspective exploded view of the upper portion of FIG. 7A showing the endotracheal tube adapter out of connection.

FIG. 7C is a side sectional view of the medical suction device of FIG. 7A.

FIG. 8 is a partial side elevation view illustrating an alternate preferred construction for the outlet end of preferred medical suction devices.

FIG. 15A is a rear perspective view of a preferred embodiment of a meconium aspirator medical device of the present invention.

FIG. 15B is a sectional view through the center of the device of FIG. 15A illustrating the operation of the valve ports.

FIG. 16A is an exploded front perspective view of the meconium aspirator medical device of FIG. 15A illustrating the use of a flexible membrane cap to cover one of the ports, as illustrated.

FIG. 16B is a sectional view similar to the view of FIG. 15B, but illustrating the use of a flexible membrane cap to cover one of the ports, shown with cap attached.

FIG. 16C is a sectional view similar to FIG. 16B, illustrating, with the top port unblocked, finger manipulation of blockage by applying pressure to the cap to deform it to block the other port at its bottom.

FIG. 20A is a perspective view of a preferred embodiment of a splash shield system according to the present invention, and showing use with an irrigation squeeze bottle.

FIG. 20B is an exploded perspective view of the embodiment of FIG. 20A, and further showing (in dotted lines) the structure of another preferred alternate embodiment using vacuum evacuation of irrigation fluid through a port situated near the plane of irrigation.

FIG. 20C is a sectional view of the embodiment of FIG. 20A, illustrating details of preferred structure.

FIG. 20D is a perspective view illustrating the use of the splash shield of FIG. 20A, inverted for use with a syringe.

FIG. 21A is a perspective view of the upper portion of a syringe of the prior art.

FIG. 21B is a side elevation view of the prior-art syringe of FIG. 21A.

FIG. 22 is a side elevation view of a preferred embodiment of the syringe of the present invention, illustrating a multiple-hole plunger.

FIG. 24A is a perspective view illustrating the use of a preferred embodiment of the combined light and tongue depressor of the present invention, illustrating its use in the intubation of an infant.

FIG. 24B is a top perspective view of the embodiment of FIG. 24A.

FIG. 24C is a bottom view of the embodiment of FIG. 24A.

FIG. 24D is a partial exploded perspective view of the bottom of the embodiment of FIG. 24A.

FIG. 24E is an end elevation view of the embodiment of FIG. 24A showing the pocket opening.

FIG. 25 is a perspective view of an alternate preferred embodiment of the light system of the present invention.

FIG. 26 is a perspective view of yet another alternate embodiment of the light system of the present invention.

FIG. 27A illustrates the use of a light system according to the present invention used for a pediatric eye examination.

FIGS. 27B and 27C illustrate the advantages in use of the light system of FIG. 27A.

FIG. 28A is a top plan view of a preferred embodiment of the cough shield medical device of the present invention.

FIG. 28B is a partial top plan view further illustrating the embodiment of FIG. 28A and showing an adhesive protector.

FIG. 28C is a perspective view of the embodiment of FIG. 28A in position above a tongue depressor to install a shield middle flap.

FIGS. 28D, 28E, and 28F are perspective views further illustrating the preferred installation steps to install the illustrated preferred cough shield.

FIG. 28G is a top plan view of the illustrated preferred cough shield in pediatric use.

FIG. 28H is a side elevation view of the illustrated preferred cough shield in pediatric use.

FIG. 28J is a perspective view of the illustrated preferred cough shield ready for use in combination with the preferred light system of this invention.

FIG. 29A is a perspective view of a preferred embodiment of the clip-on restraint of the present invention illustrating its attachment to a tube or other medical device.

FIG. 29B is an expanded perspective view of the embodiment of FIG. 29A.

FIG. 30A is a perspective view of an alternate preferred embodiment of a meconium aspirator medical device of the present invention.

FIG. 30B is a sectional view further illustrating the detail of the embodiment of FIG. 30A.

FIG. 31A is a sectional view of yet another alternate (and highly preferred) embodiment of the meconium aspirator of the present invention, further illustrating its combined use with a preferred embodiment of an endotracheal tube adapter.

FIG. 31B is a perspective view of the combined system of FIG. 31A illustrated in a restrained position and ready for use.

FIG. 32 is a perspective view of a prior art mucous or meconium specimen trap.

FIG. 33A is a perspective view of even yet another preferred embodiment of a meconium aspirator of the present invention structured for specimen collection and including an illustrated cap.

FIG. 33B is a sectional view illustrating the bottom portion of the embodiment of FIG. 33A with open-valve relief and no meconium or specimen suction.

FIG. 33C is a sectional view similar to that of FIG. 33B but with closed-valve full-flow suction of meconium.

FIG. 33D is a sectional view similar to that of FIG. 33B but illustrating the aspirator after use with the flow-control port sealed for containment of collected specimen.

FIG. 33E is a perspective view of the described collection system of FIGS. 33A-D, illustrating the inlet tube connected to the outlet port so as to fully seal collected specimen for sending to the lab.

FIG. 33F is a partial view, partially in section of the outlet port area of the aspirator device of FIG. 33E showing the detail of the structure for insertion of the inlet tubing.

FIG. 36 is a perspective view of a prior art endotracheal tube adapter.

FIG. 37A is a perspective view of a preferred embodiment of an endotracheal tube adapter according to the present invention.

FIG. 37B is a sectional view of the embodiment of FIG. 37A further illustrating detail.

FIG. 37C is a top plan view of the adapter of FIG. 37A illustrating in expanded view the flange portion.

FIG. 37D is a perspective view illustrating the use of the preferred endotracheal tube adapter of FIG. 37A, showing the adapter in place on a child patient.

FIG. 37E is a perspective view illustrating the retaining of the intubation stylet on the flange of the adapter.

FIG. 38 is a side elevation view of an adapter with a preferred endotracheal tube construction according to the present invention, showing a tactilely-apparent diameter reduction for information feedback to the intubator.

FIG. 41C is a sectional view through the center of the embodiment of FIG. 41A showing structural details and showing its fit in the illustrated bottle (which is in dotted lines).

FIG. 42A is a perspective view of yet another preferred embodiment of a splash shield according to the present invention shown attached to an IV-type squeeze bag by way of the IV spike connector of this embodiment.

FIG. 42B is an enlarged (over FIG. 42A) perspective view of the embodiment of FIG. 42A.

FIG. 42C is sectional side view of the embodiment of FIG. 42A illustrating the structural details thereof.

FIG. 42D is a bottom view of the embodiment of FIG. 42A.

FIG. 43A is front view illustrating yet another preferred embodiment of a splash shield according to the present invention, showing a spike connector attached to a squeeze bag and also fitted into a cylindrical splash shield element.

FIG. 43B is a perspective view of the embodiment of FIG. 43A, showing the spike connector separated from the cylindrical splash shield element.

FIG. 43C is a partial sectional view showing the connection details with the spike connector attached to the cylindrical splash shield element.

FIG. 44A is an exploded perspective view of yet another preferred embodiment of the splash shield of the present invention, showing a syringe-type end, a syringe adapter to control the irrigation stream, and a tubular splash shield element.

FIG. 44B is a sectional view of the embodiment of FIG. 44A illustrating the details with the parts connected.

FIG. 45A is an exploded perspective view of yet another preferred embodiment of the splash shield of the present invention, showing the end of an irrigation bottle, a bottle adapter to control the irrigation stream, and a tubular splash shield element.

FIG. 45B is a sectional view of the embodiment of FIG. 45A illustrating the details with the splash shield connected to the bottle (shown in dotted lines).

FIG. 46A is a perspective view of a preferred embodiment of a combined splash shield and irrigation squeeze tube according to the present invention.

FIG. 46B is a partial perspective view of the embodiment of FIG. 46A, partially cut away to show its use with cap removed.

FIG. 47A is a perspective view of yet another preferred embodiment of a splash shield according to the present invention shown with an inlet attached to an irrigation syringe and an outlet attached to a vacuum line.

FIG. 47B is a side view of the embodiment of FIG. 47A, shown attached to the irrigation syringe.

FIG. 47C is a front view of the embodiment of FIG. 47A, with the irrigation syringe in dotted lines.

FIG. 47D is a side sectional view of the embodiment of FIG. 47A showing the structural details and fluid flow directions FIG. 47E is a top view of the embodiment of FIG. 47A.

FIG. 47F is a partial sectional view through the section 47F-47F of FIG. 47B.

FIG. 47G is a bottom view of the embodiment of FIG. 47A.

FIG. 48A is a front view of an alternate preferred embodiment of an endotracheal tube according to the present invention, shown attached to an endotracheal tube adapter.

FIG. 48B is a partial enlarged front view, partially in section, of the embodiment of FIG. 48A showing the details of structure and of the connection to endotracheal tube adapter.

FIG. 48C is a partial perspective view of an upper section of the endotracheal tube of FIG. 48A, showing separation after cutting.

FIG. 49 is a perspective view of yet another preferred embodiment of an endotracheal tube according to the present invention, showing a dual lumen.

FIG. 50A is a perspective view of the preferred elements of an unassembled wound treatment kit according to a preferred embodiment of the present invention.

FIG. 50B is an exploded perspective view of a preferred embodiment of the wound treatment kit of this invention.

FIG. 50C is a perspective view of the exterior of the assembled wound treatment kit of the present invention.

FIG. 50D is a sectional view of the illustrated wound treatment kit, assembled and filled, through its center and the center of the external pocket in the lower cap.

FIG. 50E is a sectional view taken through the section 50E-50E of FIG. 50D.

Figure 51A:
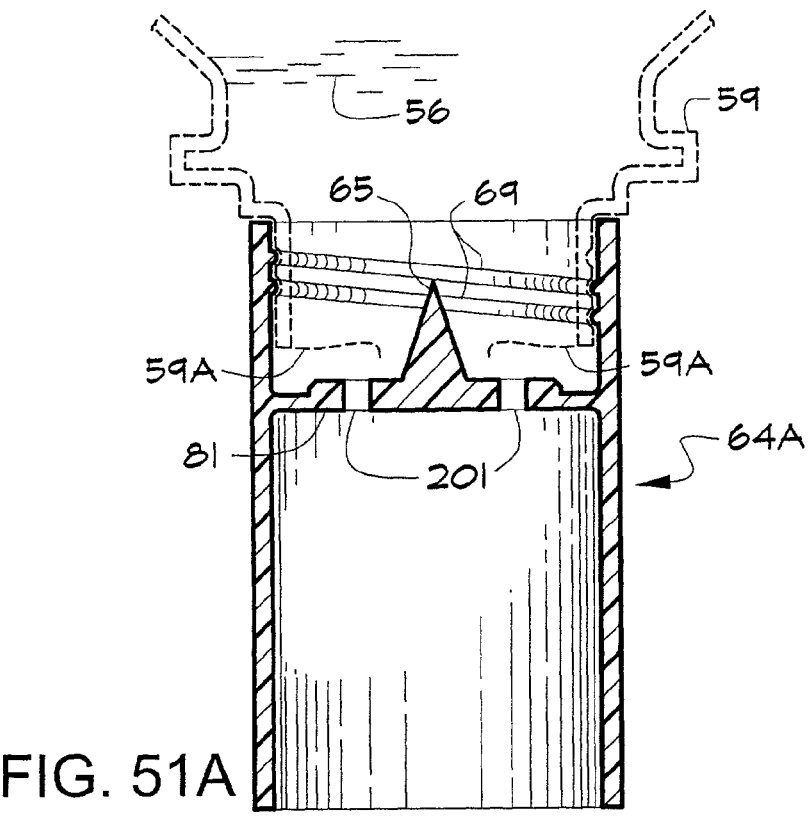

FIG. 51A is a sectional view of an alternate preferred embodiment of the present invention similar to the embodiment and view of FIG. 20C but including a membrane-puncturing element.

Figure 51B:
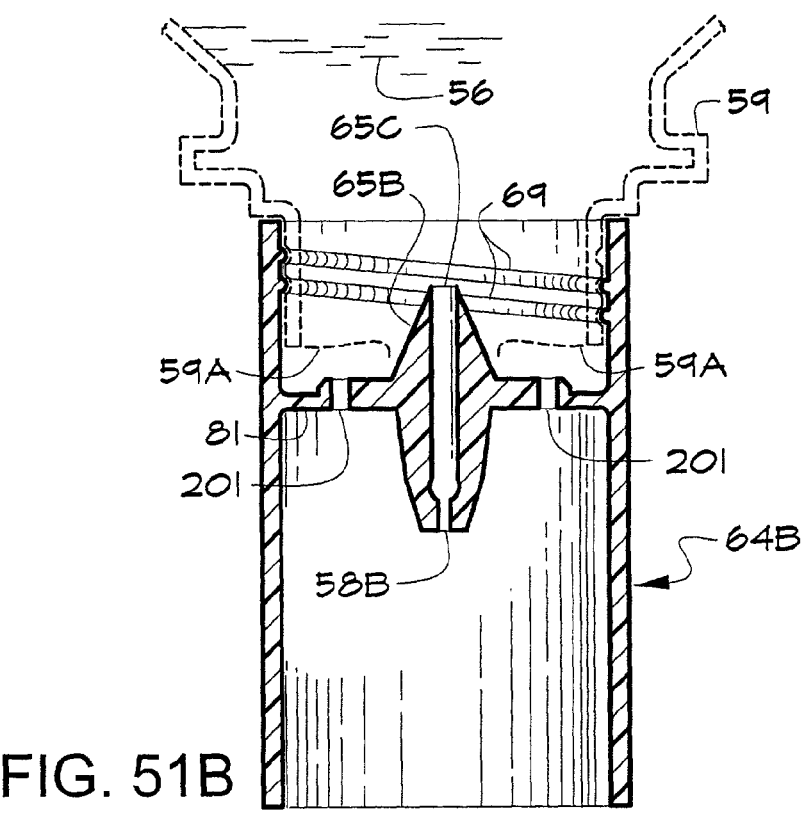

FIG. 51B is a sectional view of an alternate preferred embodiment of the present invention similar to the embodi-ment and view of FIG. 51A but including a hole through the membrane-puncturing element.

Figure 52A:
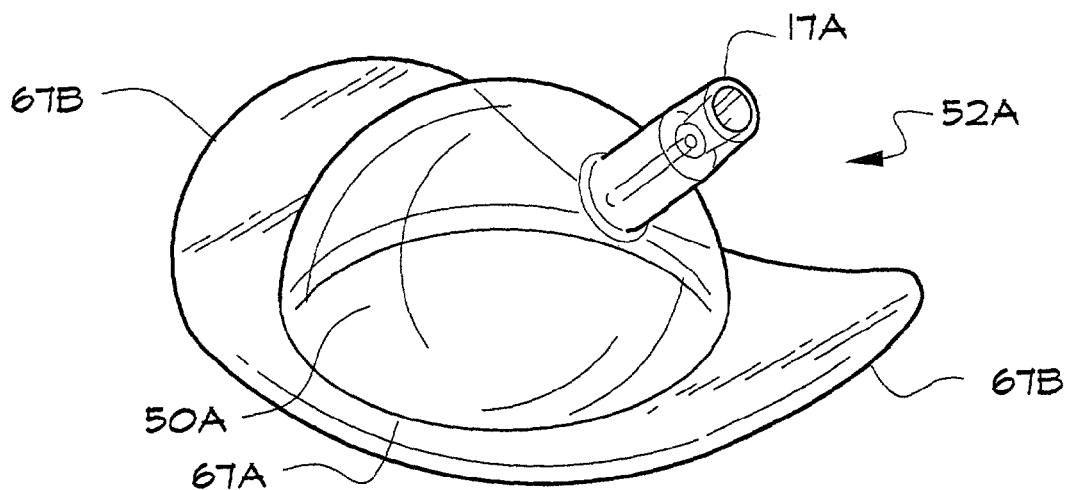

FIG. 52A is a perspective view of am alternate preferred splash shield embodiment according to the present invention.

Figure 52B:
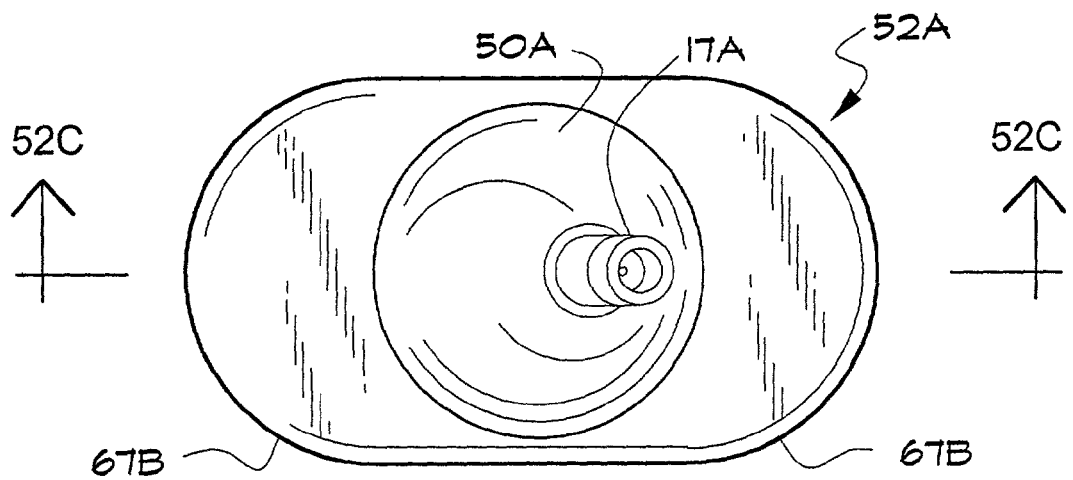

FIG. 52B is a top view of the embodiment of FIG. 52A.

Figure 52C:
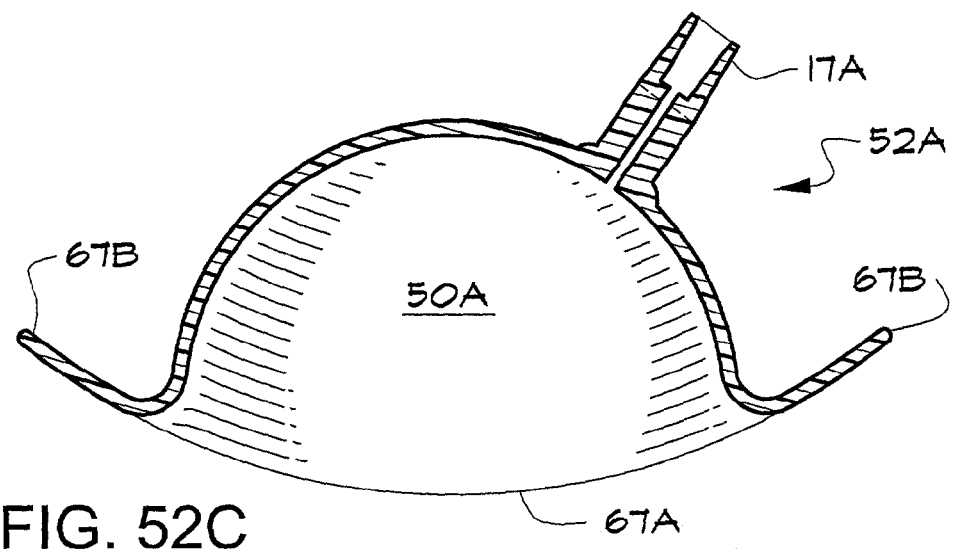

FIG. 52C is a sectional view through the section 52C-52C of FIG. 52B.

DETAILED DESCRIPTION OF A PREFERRED EMBODIMENT AND THE BEST MODE OF PRACTICE

Figure 1A:
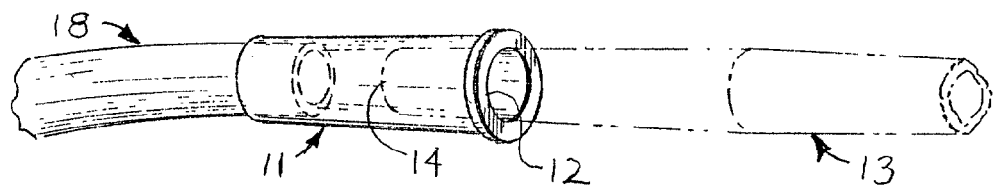
FIG. 1A is a perspective view illustrating a prior art vacuum line where a coupling member is used between a vacuum source line and a vacuum device.

FIG. 1A is a perspective view illustrating a prior art vacuum line 10 where a coupling member 11 is used between a vacuum source line 18 and a hand-held vacuum device 13. The distal inlet end 12 of the coupling member 11 holds the proximal end 14 of the vacuum device 13, e.g., a catheter.

Figure 1B:
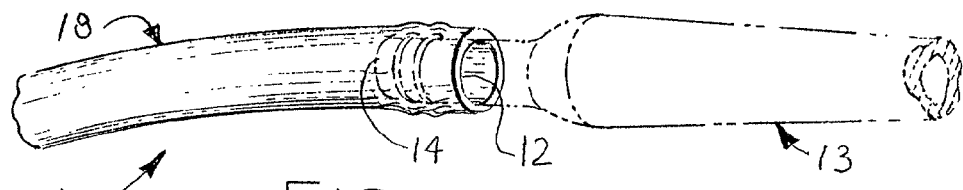
FIG. 1B is a perspective view illustrating a prior art vacuum line where a vacuum source line is directly connected to a vacuum device.

FIG. 1B is a perspective view illustrating a prior art vacuum line 10 where a vacuum source line 18 is directly connected to a vacuum device 13. The distal inlet end 12 of the vacuum source line 18 holds the proximal end 14 of the vacuum device 13.

FIG. 2A is a perspective view illustrating a prior art vacuum device 15 connected at its proximal end 14 by a coupling member 11 to a vacuum line 10 (connected within the distal inlet end 12 of the coupling member 11) and connected at its distal end 17 to a medical device 13, such as a meconium aspirator or an endotracheal tube and adapter. Vacuum device 15 has a vacuum control port 16.

FIG. 2B is a perspective view illustrating a prior art vacuum device 15 connected at its proximal end 14 directly to a vacuum source line 18 and connected at its distal end 17 to a medical device 13 such as a catheter. Vacuum device 15 has a vacuum control port 16.

FIG. 2C1 is a perspective view illustrating another prior art vacuum device 15 connected at its proximal end 14 directly to a vacuum source line 10 and connected at its distal end 17 to a medical device 13 like a catheter and having a vacuum control port 16 and including a detached soft cap 130 for closing the port 16 without supposedly without finger contamination. As shown soft cap 130 comprises a finger-compressible pillar portion having holes 131 for permitting air flow.

FIG. 2C2 is a perspective view of the prior art device 15 of FIG. 2C1 showing air flow with the soft cap 130 attached. As shown, port 16 has an upper male ledge 132 which fits within a lower female ledge 133 of soft cap 130 to attach the soft cap 130 as shown. The arrows indicate the normal flow of air through the four peripheral holes 131.

FIG. 2C3 is a perspective view of the prior art device 15 of FIG. 2C1 showing a finger 20 pressing the soft cap 130 to close the vacuum control port 16 by compressing the upper portion of soft cap 130, which thereby effectively closes port 16. A primary idea of this prior art was to protect finger 20 from contamination. However, as illustrated by FIG. 2C4, a partial side view of the prior art device 15 of FIG. 2C1, it is shown how, with the vacuum control port 130 on a bottom side, the user's finger 20 may be exposed to debris 134 dripping from soft cap 130 and the user may thereby be contaminated.

Figures 3A, 3B, 3C, 3D:
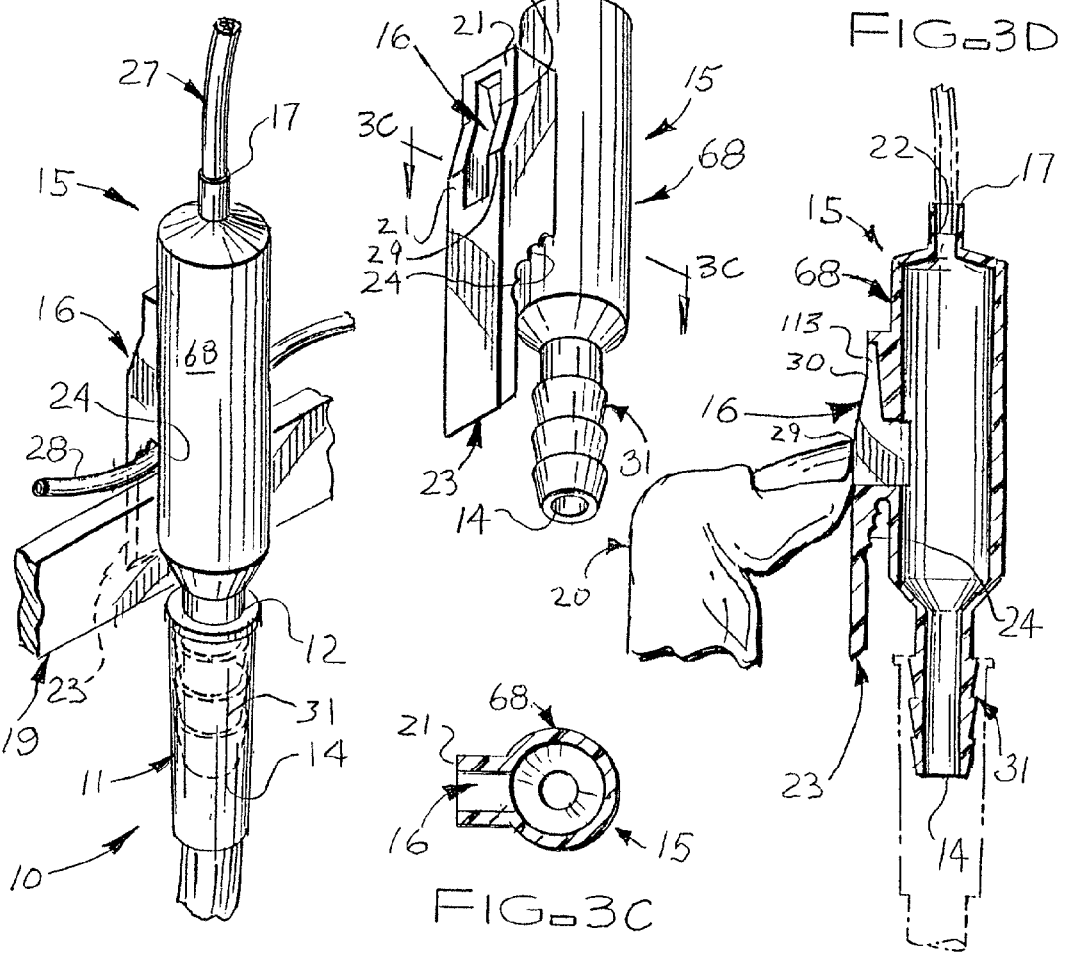
FIG. 3A is a rear perspective view illustrating a preferred embodiment of a medical suction device according to the present invention, shown as connected to inlet and outlet members and in a restraint position.
FIG. 3B is a front perspective view of the medical suction device of FIG. 3A.
FIG. 3C is a sectional view through the section 3C-3C of FIG. 3B.
FIG. 3D is a side sectional view of the medical suction device of FIG. 3A and further showing use of a finger for partially closing a flow control port according to the present invention.

FIG. 3A is a rear perspective view illustrating a preferred embodiment of a medical suction device 15 according to the present invention, shown as connected to inlet and outlet members and in a restraint position. Medical suction device 15 is connected at its distal end 17 to a suction catheter 27 and is connected at its proximal end 14 to coupling member 11 of vacuum line 10 at its distal end 12. Medical suction device 15

(embodying herein a first such separate user-hand-held-type medical component located in a first position) preferably comprises a straight, cylindrical body 68 (as shown) and includes a flow control port 16. A tube 28, such as an endotracheal tube or possibly a portion of suction catheter 27 (embodying herein that such first and second such medical components may be structured and arranged for combined medical use), is shown restrained within tubing retainer 24 preferably located on the inside of clip restraint 23 as shown. Tube 28 embodies herein a second such separate user-hand-held-type medical component in a second position adjacent such first position; and tubing retainer 24 embodies herein restraint means on such first separate medical component for temporarily restraining, without substantial interference with normal use of such first separate medical component, such second separate user-hand-held-type medical component. Clip restraint 23 is shown in use restraining device 15 to an equipment portion 19 in the treatment area, such as the edge of a tray or bed (clipping to such bed embodying herein that such restraint means is structured and arranged for temporary clipping of such first separate medical component to a non-hand-held-type item of equipment, wherein such restraint means is structured and arranged for use in such clipping with multiple sizes and types of such equipment). Note that the clip illustrated is extending from the outer surface of the suction control valve and is of a much greater length than the extensions of prior art such as the one illustrated in FIG. 2A and therefore will have improved griping properties. This might include gripping on irregular edges where longer gripping space is needed or having varying gripping spaces as shown between clip 23 and the body of device 15 and the region of outlet 14, therefore providing a clip that not only has improved features due to its length but also due its varying stepped width structure. It is especially noted that the clip of the present invention has a longitudinal length which is greater than its distance from the body of the suction device; and this contributes to its above-discussed usefulness.

FIG. 3B is a front perspective view of the medical suction device 15 of FIG. 3A, further illustrating a preferred externally-barbed outlet projection 31 for connecting to a vacuum line 10 (as shown in dotted lines in FIG. 3A). Also shown is the external structure of flow control port 16. FIG. 3C is a sectional view through the section 3C-3C of FIG. 3B and shows the detail of the port construction permitting flow control by movement/placement of finger 20 to occlude part or all of port 16 to achieve a desired suction-vacuum variation in the suction system, with repeatable incremental control by a user of the illustrated single-finger-operable valve means. As shown, the construction of port 16 permits increasingly finer control as the finger 20 occludes more and more of the opening of port 16 (as the finger 20 is moved in the direction of distal inlet end 17, sliding along the outer surface 21 of port 16 and clip restraint 23. Tactile feedback is provided to the user in this embodiment by plane changes which act as tactile markers 29 and 30, which the user's finger 20 can feel as the finger 20 moves across them, thus providing repeatable incremental control through this tactile feedback means for amplifying tactile feedback to a user to enhance distinguishing of control increments.

FIG. 3D is a side sectional view of the medical suction device 15 of FIG. 3A and further showing use of a finger 20 for partially closing flow control port 16 according to the present invention, the user being shown as following tactile feedback to close only that part of port 16 delimited by tactile marker 29, since the end of the plane so delimited can be felt by finger 20. It is noted that the geometry, with narrower and smaller conduits 113 for air passage as the distal end of port 16 is approached, provides finer increments of flow control as the port 16 is closed by finger 20 from the proximal end of the port to the distal end of the port (as shown). Also shown clearly in cross-section in this view is tubing retainer 24, including several size-steps (in cross-section) for respectively assisting in retaining tubes 28 of different sizes in various-size concavities, embodying herein that such restraint means is structured and arranged for restraining multiple kinds of user-hand-held-types of equipment, and embodying herein also that such restraint means is structured and arranged for restraining multiple sizes of tubing, and further embodying herein that such restraint or holding means comprises a concavity structured and arranged for receiving and frictionally holding a flexible tube portion having a diameter slightly larger than a dimension of such concavity (using friction).

FIG. 3E is a side sectional view of the medical suction device 15 of FIG. 3A and further showing use of a finger 20 for fully closing flow control port 16 according to the present invention, the user being shown as following tactile feedback to close also that part of port 16 lying in the plane distal of and delimited by tactile marker 30, since the plane so delimited can be felt by finger 20. It is noted that the designs/structure of the flow control ports of FIGS. 3 and 4 embody herein wherein such valve means comprises a valve having a such external aperture larger than an internal aperture of such valve, such valve thereby comprising a multitude of valve depths; and wherein a distal portion of such valve has a smaller valve depth that a proximal portion of such valve; structured and arranged in such manner as to provide more restricted flow in such distal portion of such valve than in such proximal portion of such valve; and wherein such valve is constructed and arranged so that such external aperture and such smaller valve depth cooperate in such manner that each such progressive incremental movement distally of the fingertip may provide progressively finer flow control through such aperture.

FIG. 4A is a rear perspective view illustrating an alternate preferred embodiment of a medical suction device 15 according to the present invention. In this embodiment, as shown, clip restraint 23 is wider and further removed from body 68 than in the embodiment of FIG. 3. And tubing restraint 25 has its structure on the distal portion of the structure of port 16 (as opposed to the embodiment of FIG. 3, in which tubing restraint 24 is located on the proximal portion of port 16). It is noted that, preferably, such a device or tubing restraint would keep a contaminated end of a suction tube from directly cross contaminating other areas of the device or other devices that might be used by and/or touched by the operator. For example, if one were to have a tubing restraint of a standard suction catheter, it is preferred to have it on the distal end of the device, so that the tubing could be "locked" in without a "dirty" suction catheter tip touching the finger control area of the device. Such an arrangement might prevent the spread of disease from the dirty catheter tip to a finger control to the finger of the operator and on to another patient. Such a restraint, therefore, would not only prevent the spread of disease directly from an unrestrained device end, such as a suction catheter tip, but would also prevent the spread of disease indirectly from the device to the operator to another patient. Such restraint of such suction catheter on such suction device embodies herein that such first separate user-hand-held-type medical component is structured and arranged for attachment with a proximal portion of the such flexible tube, and that such restraint means is structured and arranged for temporarily restraining a distal portion of the such flexible tube adjacent such first separate user-hand-held-type medical component for ready availability for potential use by the user.

FIG. 4B is a side sectional view of the medical suction device of FIG. 4A. This view shows best the step structure of tubing restraint 25, permitting the restraint of many sizes of tubing 28. The embodiment of FIG. 4B (as well as many other of the illustrated embodiments) embodies herein that the restraint means of the present invention preferably comprises an external aperture means for regulating suction and wherein such external aperture means comprises single-finger-operable valve means for repeatable incremental user control of suction-vacuum variation in such suction system and tactile feedback means for amplifying tactile feedback to a user to enhance distinguishing of control increments. It is also noted that the clip restraint 23 of this embodiment permits the device 15 to be restrained on a wider rim or shelf than is true of the device 15 of FIG. 3. FIG. 4C is a sectional view through the section 4C-4C of FIG. 4A. The features of FIG. 4 also embody herein that both such first restraint means and such second restraint means are located inwardly of such external aperture means with respect to such device.

FIG. 5A is a partial side elevation view illustrating another alternate preferred embodiment of a medical suction device 15 according to the present invention. In this embodiment, there is a changed configuration (as shown) of the flow control port 16 in order to put the tubing restraint 26 in a configuration permitting tubing to be restrained in a position parallel to cylindrical body 68. FIG. 5B is a top plan view of the embodiment of FIG. 5A; and FIG. 5C is a sectional view through the section 5C-5C of FIG. 5A, showing the details of this embodiment.

FIG. 6 is a partial side elevation view illustrating an alternate preferred construction for the inlet end 17 of preferred medical suction devices 15. An externally barbed projection 32 is designed to fit within an inlet tube 18 (dotted lines).

FIG. 7A is a perspective view of a medical suction device 15 according to the present invention showing another preferred construction for the inlet end 17, and showing an endotracheal tube adapter 34 (with endotracheal tube 28) fitting within inlet 33, which is internally tapered for accepting the adapter 34. The proximal outlet end 14 of device 15 is shown connected to a vacuum line 10. FIG. 7B is a partial perspective exploded view of the upper portion of FIG. 7A showing the endotracheal tube adapter 34 out of the connection. FIG. 7C is a side sectional view of the medical suction device 15 of FIG. 7A, again illustrating the cross-section of the clip restraint 23.

FIG. 8 is a partial side elevation view illustrating another alternate preferred construction for the outlet end 14 of preferred medical suction devices 15, showing an externally tapered male projection 35 which makes a friction fit with vacuum line 10.

Figure 9:
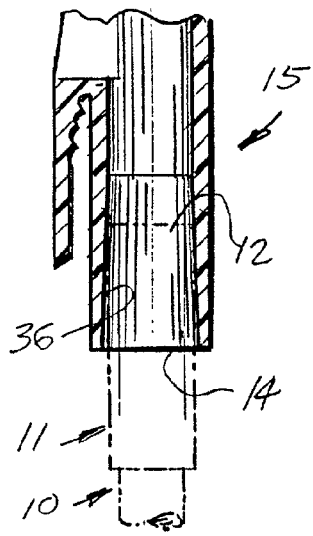
FIG. 9 is a partial sectional view illustrating another alternate preferred construction for the outlet end of preferred medical suction devices.

FIG. 9 is a partial sectional view illustrating another alternate preferred construction for the outlet end 14 of preferred medical suction devices 15, showing an internally tapered female connection 36 which makes a friction fit with end coupling 11 of vacuum line 10, as shown.

Figure 10:
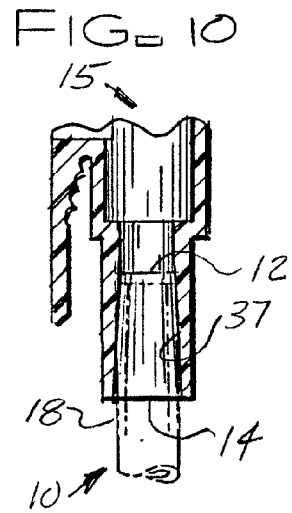
FIG. 10 is a partial sectional view illustrating yet another alternate preferred construction for the outlet end of preferred medical suction devices.

FIG. 10 is a partial sectional view illustrating yet another alternate preferred construction for the outlet end 14 of preferred medical suction devices 15. Internally tapered female connection (cylinder again) 37 makes a friction fit directly with vacuum tubing 18 of vacuum line 10.

Figure 11:
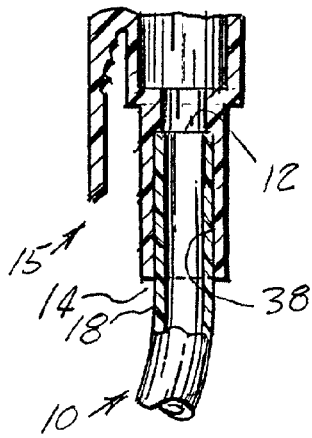
FIG. 11 is a partial sectional view illustrating even yet another alternate preferred construction for the outlet end of preferred medical suction devices.

FIG. 11 is a partial sectional view illustrating even yet another alternate preferred construction for the outlet end 14 of preferred medical suction devices 15. Internal straight (untapered) female outlet 38 is constructed to fit with and be permanently bonded to vacuum tubing 18 of vacuum line 10.

Figure 12B:
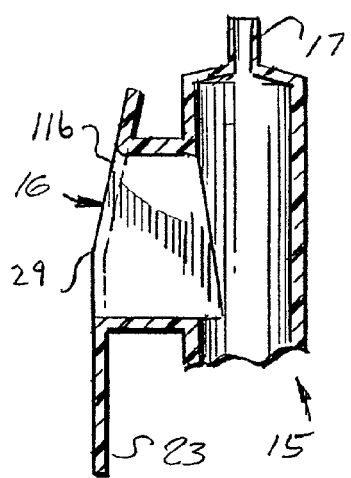
FIG. 12B is a sectional view through the section 12B-12B of FIG. 12A.
Figure 12A:
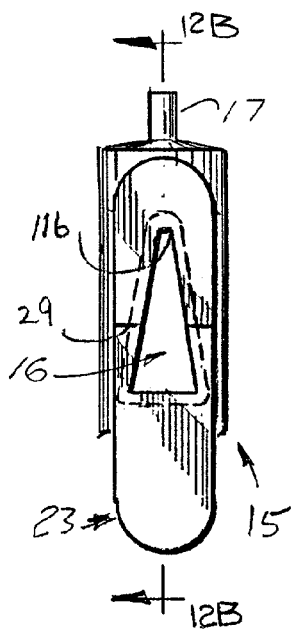
FIG. 12A is a side elevation view of an alternate preferred construction for the flow control port of preferred medical suction devices.

FIG. 12A is a side elevation view of an alternate preferred construction for the flow control port 16 of preferred medical suction devices 15. Flow control port 16 has a triangular shape with its narrow end 116 to the distal side of device 15, assisting finer increments of flow control as the port 16 is closed by a finger 20 from the proximal end of the port 16 to the distal end of the port 16; and tactile feedback to the user is again provided by a tactile marker 29, a plane change of the surface of port 16 away from the user, as shown. FIG. 12B is a sectional view through the section 12B-12B of FIG. 12A, showing the detail of construction of this embodiment of port 16 and clip restraint 23.

Figure 13:
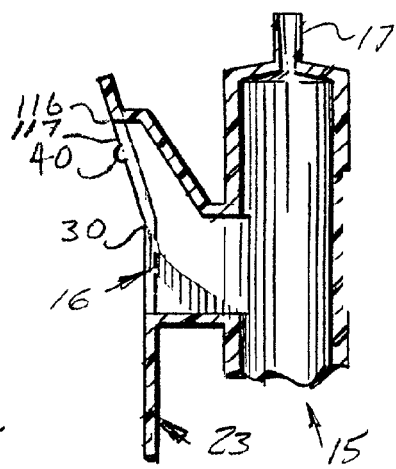
FIG. 13 is a partial side sectional view of another alternate preferred construction for the flow control port of preferred medical suction devices.

FIG. 13 is a partial side sectional view of another alternate preferred construction for the flow control port 16 of preferred medical suction devices 15, showing an alternate preferred cross-section for the triangular port of FIG. 12A. In this embodiment, tactile feedback to the user is again provided by a tactile marker 30, a plane change of the surface of port 16 toward the user, as shown (embodying herein wherein an external surface peripheral to such aperture comprises at least a first and a second flat surface portion, each such flat surface portion lying in a substantially different plane, whereby such external surface comprises such tactile feedback means, and wherein such first flat surface portion comprises a proximal portion of such external surface and such second flat surface portion comprises a distal portion of such external surface, whereby a movement distally of the user's fingertip provides the user tactile feedback as the fingertip moves onto such second flat surface portion, and wherein an external angle between such first flat surface and such second flat surface is an acute angle. Additionally, one or two small projecting bumps 40 may be placed on either side of the port 16 near the smaller end of the triangular port as yet another tactile marker for a user who wishes near maximum vacuum but with a relief opening 117 at this end 116 of the port 16.

Figure 14A:
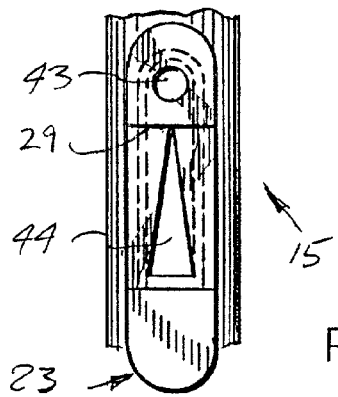
FIG. 14A is a front elevation view of yet another alternate preferred construction for the flow control port of preferred medical suction devices.
Figure 14B:
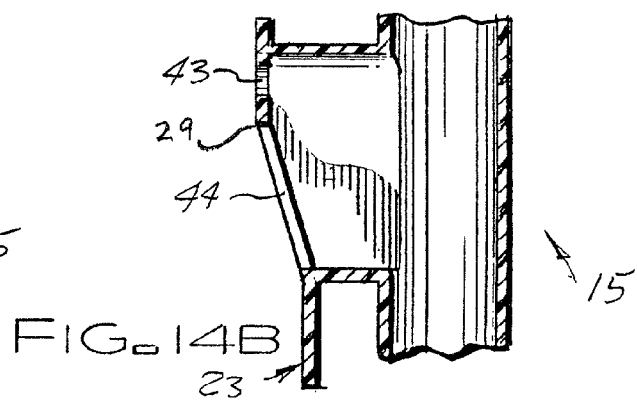
FIG. 14B is a partial side sectional view through the center of the device of FIG. 14A.

FIG. 14A is a front elevation view of yet another alternate preferred construction for a flow control port 44 of preferred medical suction devices 15. Flow control port 44 is again preferred to be triangular in shape; there is also, however, a second small (preferably circular) relief port 43, it being seen that a user may have finger control of vacuum as before but must take special pains to eliminate the relief, overcoming the tactile feedback of the plane change away from the user at tactile marker (line) 29, as shown, i.e., the plane change viewed from the outside is at an obtuse angle (embodying herein wherein an external angle between such first flat surface and such second flat surface is an obtuse angle). The finger may be said to be going from a conformable region on the valve to a non-conformable region. FIG. 14B is a partial side sectional view through the center of the device 15 of FIG. 14A, showing further detail. The port tactile feedback arrangements of FIG. 14 (as well as other such arrangements shown in this specification) embody herein that such tactile feedback means comprises incremental structures selected from the group consisting of multiple ports, multiple distinguishable planes, multiple distinguishable areas of different cross-section, and multiple distinguishable contours; and also embody herein that such aperture means comprises at least one second separate small aperture structured and arranged for relief purposes and wherein such second separate small aperture is located at the distal portion of such aperture means. The illustrated arrangement of FIG. 14 also embody herein wherein such single-finger-operable valve means comprises a substantially triangular external aperture, having three respective sides and three respective opposed points, structured and arranged in such manner that a user's fingertip may progressively block such aperture from a first such side of such aperture to a such respective first opposed point of such aperture by progressively incrementally moving such fingertip toward such first opposed point, and whereby each such progressive incremental movement may block a progressively smaller percentage of such aperture, thereby providing progressively finer flow control through such aperture, and wherein such aperture comprises a substantially isosceles triangle having a longest dimension from such first side to such respective first point.

FIG. 15A is a rear perspective view of a preferred embodiment of a meconium aspirator medical device 39 of the present invention. FIG. 15B is a sectional view through the center of the device 39 of FIG. 15A illustrating the operation of the valve ports, i.e., of flow control port 16 (see top of FIG. 15B) and internal flow control opening 46 (see bottom of FIG. 15B). Meconium aspirator 39 has preferably a cylindrical body 47 from which protrudes a distal inlet end 17 as shown, to which is usually affixed a suction catheter 27. Externally stepped outlet 66 is usually connected to a vacuum line 10 (shown in dotted lines). Protruding outward (as shown) from a distal portion of body 47 and preferably somewhat parallel to outlet 66 is clip restraint 23, which also comprises a tubing restraint 24 (or like 25) as shown (similarly in clip construction to that of FIG. 3D). Inlet port 22 has an internal taper to provide a friction fit with suction catheter 27. As shown best in FIG. 15B, the body end opening 48 must be kept closed for the flow control valve of this embodiment to work, as by a finger/thumb 20 as shown. The flow control is achieved by a top finger partially occluding port 16 as shown; this again provides some incremental control. It is noted that, when port 16 is left open, meconium aspirator 39 still has a flow control option by the partial/full occluding of internal flow control opening 46 by the lower illustrated finger 20. This arrangement embodies herein wherein such second inlet means comprises first aperture means for regulating air flow in such first user-hand-held-type medical component from a first portion of such first user-hand-held-type medical component, and second aperture means for regulating air flow in such first user-hand-held-type medical component from a second portion of such first user-hand-held-type medical component. Incremental control can be achieved by fully occluding opening 48 and reducing the opening area of the device, or by partially occluding opening 48 using opening 46 as a positioning marker for placement of the finger. Incremental control of internal flow control opening 46 can be achieved by varying the depth or position of the finger 20 between 48 and 46 without ever touching 46. In addition, control of the internal port can be done directly by touching and covering the internal flow control opening with the finger by varying degrees.]

FIG. 16A is an exploded front perspective view of the meconium aspirator medical device 39 of FIG. 15A illustrating the use of a flexible membrane cap 45 to cover opening 48, as illustrated. FIG. 16B is a sectional view similar to the view of FIG. 15B, but illustrating the use of a flexible membrane cap to cover opening 48, shown with cap 45 attached. FIG. 16C is a sectional view similar to FIG. 16B, illustrating, with the top port 16 unblocked, finger manipulation of blockage by applying pressure to the cap 45 to deform it to block opening 46 to varying degrees including the complete occlusion of opening 46, as shown. This arrangement embodies herein a cap means for temporarily sealing such third inlet means, wherein such cap means is structured and arranged, while sealing such third inlet means, for regulating air flow through such second aperture means by movement of portions of such cap means by a user's finger, and further wherein such cap means is structured and arranged, while sealing such third inlet means, for sealing such second aperture means.

Figure 17:
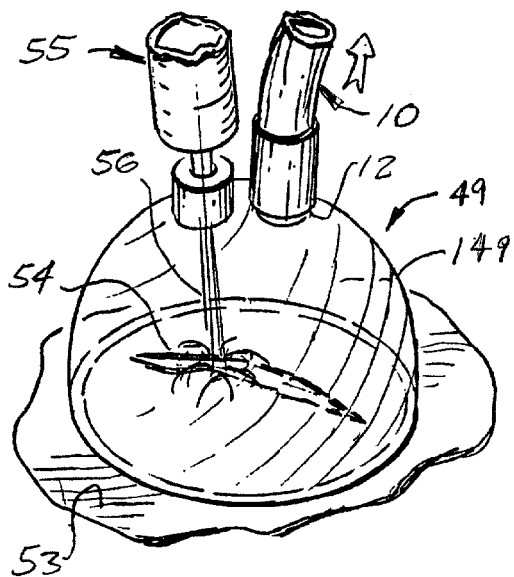
FIG. 17 is a perspective view illustrating a prior art splash shield medical device.

FIG. 17 is a perspective view illustrating a prior art splash shield medical device 49. Wound 54 of flesh/skin 53 is covered by the hemispherical shield 149; a blast of saline solution 56 is sprayed on the wound 54 by means of pressure and flow provided by syringe 55; and excess fluid is removed by the suction of vacuum line 10 connected centrally to the splash shield 49 at the distal end 12 of shield 49. It is seen that in this design, in and out flow directions fight each other and deter from washing the wound and from evacuating the solution from the wound surface; and it is possible to "puddle" over the wound instead of having a flow direction "sweep" the wound, i.e., debris may be driven straight down and deeper into the wound.

Figure 18A:
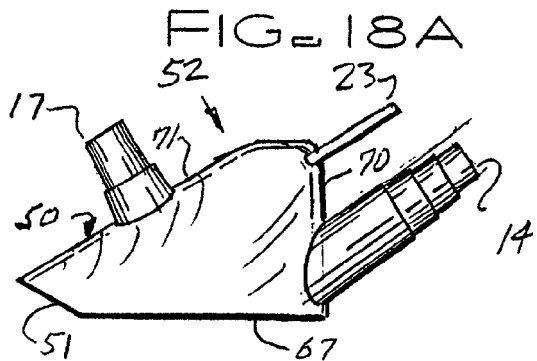
FIG. 18A is a side elevation view of a preferred embodiment of the splash shield medical device of the present invention.
Figure 18B:
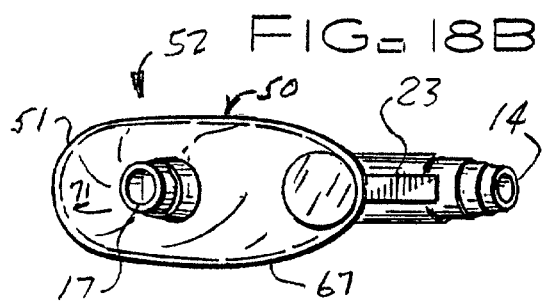
FIG. 18B is a top plan view of the embodiment of FIG. 18A.
Figure 18C:
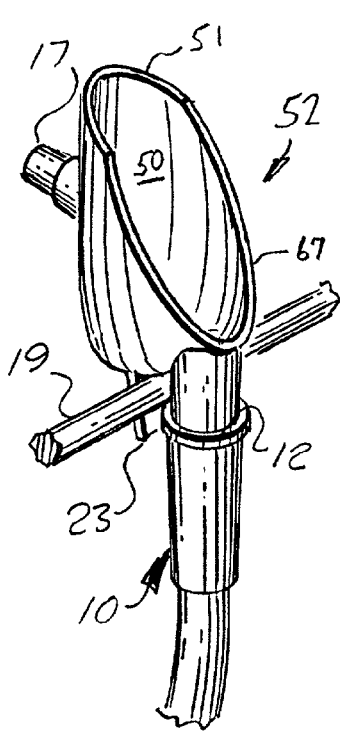
FIG. 18C is a perspective view of the embodiment of FIG. 18A showing it in a restrained position.
Figure 18D:
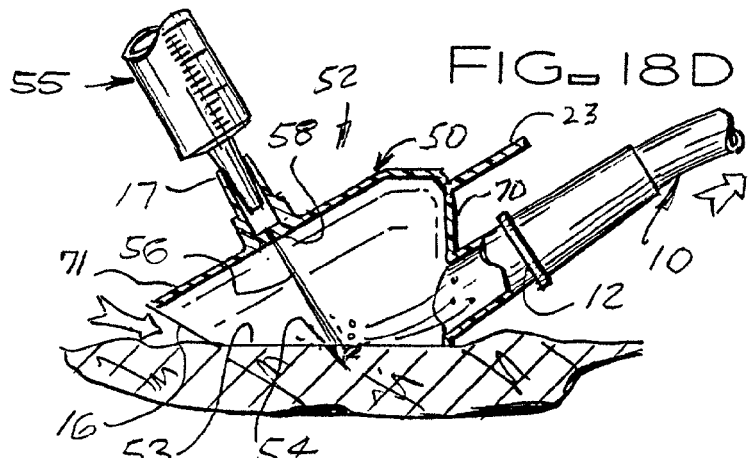
FIG. 18D is a side sectional view of the embodiment of FIG. 18A, illustrating its operation.

FIG. 18A is a side elevation view of a preferred embodiment of the splash shield medical device 52 of the present invention. Preferably the device may be made of an inexpensive disposable transparent biocompatible medical grade plastic such as a US FDA class VI PVC or polycarbonate that may also be sterile to prevent wound infection. FIG. 18B is a top plan view of the embodiment 52 of FIG. 18A. FIG. 18C is a perspective view of the embodiment 52 of FIG. 18A showing it in a restrained position, as on a portion of nearby equipment 19. FIG. 18D is a side sectional view of the embodiment 52 of FIG. 18A, illustrating its operation. As shown, the splash shield medical device of this preferred embodiment includes proximal outlet end 14 and a distal opening 17 for entry of the wound-washing fluid, shown as saline solution 56. The smooth rounded body 50 has an opening, as shown, which is either rectangular with rounded ends or a similar long oval in shape (seen most clearly in FIG. 18B). Most of the illustrated bottom opening is a portion 67 in a flat plane; but the distal end portion 51 of the bottom opening is in a plane coming upwards from the plane of portion 67 at about an angle of 30 degrees, as shown. A clip restraint 23 is preferably located near the top of the body 50 and protruding from the body 50 at about a parallel relationship to the protrusion of outlet 14. As shown, the proximal end wall 70 of body 50 is relatively vertical while the distal end wall 71 of body 50 rises very gradually at no more than about 45 degrees from the horizontal. The outlet 14 is located near the bottom opening portion 67 and near the bottom of substantially vertical end wall 70. The inlet 17 is located approximately centrally on the distal end wall 71.

Figure 18E:
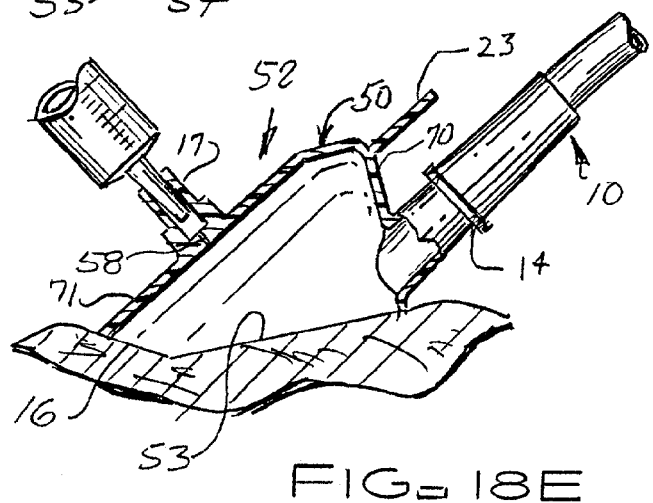
FIG. 18E is a side sectional view of the embodiment of FIG. 18A, further illustrating operation with relief closure.

With reference to FIG. 18D, the described preferred geometry permits the following operation (as shown) of device 52. The problems of prior art splash shield devices like that of FIG. 17 are overcome with the embodiment of FIGS. 18A-E. The flushing saline solution 56, as from syringe 55, irrigates wound 54 with a flow that flushes the debris toward and into vacuum line 10 by way of inlet end 12. Note that the placement of inlet end 12 near the flesh 53 portion of the device 52 assists in an efficient unidirectional flush flow to efficiently clean the wound 54 and remove debris and excess fluid (as shown). Also, the elongated bottom shape (in an appropriate size) is more suited than a circular bottom shape for shielding and collecting flushing fluids on non-flat body parts such as arms, fingers, and feet. It is also noted that the relief afforded by the raised portion 51 of the shield bottom assists in providing more air flow (from an efficient direction) as needed for good flushing. And, as illustrated by FIG. 18E (a side sectional view of the embodiment of FIG. 18A), the user may still press the shield 52 toward the flesh 53 to operate the shield with relief closure as desired. This non-flat contour also assists in the pivoting of the device and the irrigation jet along the wound 54, changing the angle of the jet in relation to a position or location on the skin in a linear fashion.

FIGS. 52A (a perspective view), 52B (a top view), and 52C (a sectional view through the section 52C of FIG. 52B) illustrate another preferred embodiment of a splash shield 52A having many common advantages, arrangements and functions with splash shield 52, with a few exceptions noted as follows. Bottom portion 67A preferably has a rounded periphery, preferably generally oval or circular, as shown. As shown, extending from this periphery is an extension 67B, as shown, with which to assist rocking of splash shield 52A to better direct the splash stream along the wound and also which performs a function of protecting the fingers and hands of the user from irrigation fluid and wound debris. As shown, bottom portion 67A also implements the "rocker" profile of itself and the extension 67B. [Body 50A and distal opening 17A perform the same functions as body 50 and distal opening 17 of shield 52].

Figure 18F:
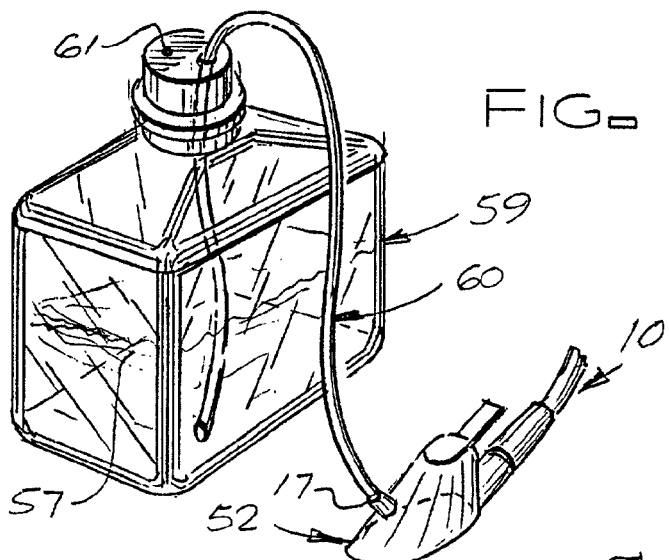
FIG. 18F is a perspective view of a preferred alternate usage of the splash shield of the type of FIG. 18A, further illustrating siphoning of irrigation fluid from a fluid container.

FIG. 18F is a perspective view of a preferred alternate usage of the splash shield 52 of the type of FIG. 18A, further illustrating siphoning of irrigation fluid 57 from a fluid container 59 by way of tubing 60. Vent opening 61 is preferably provided in container cap 80 for well known reasons.

Figure 19A:
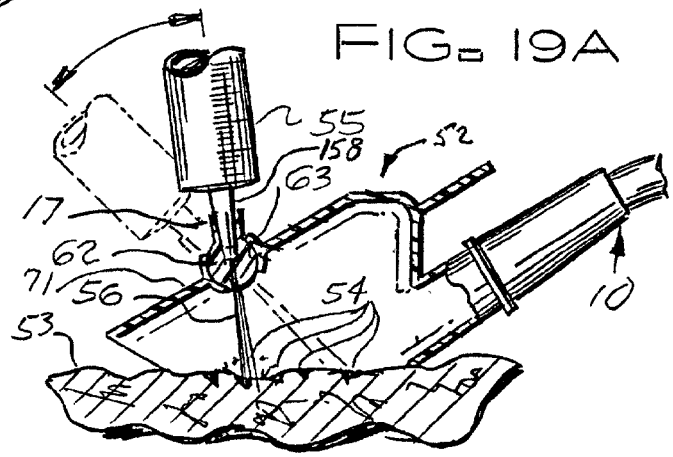
FIG. 19A is a side sectional view of an alternate preferred embodiment of the splash shield of the present invention, illustrating its operation incorporating an inlet swivel structure.
Figure 19B:
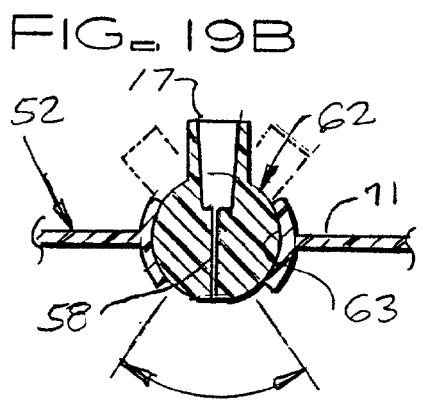
FIG. 19B is a partial expanded sectional view of the embodiment of FIG. 19A, illustrating swivel detail.
Figure 19C:
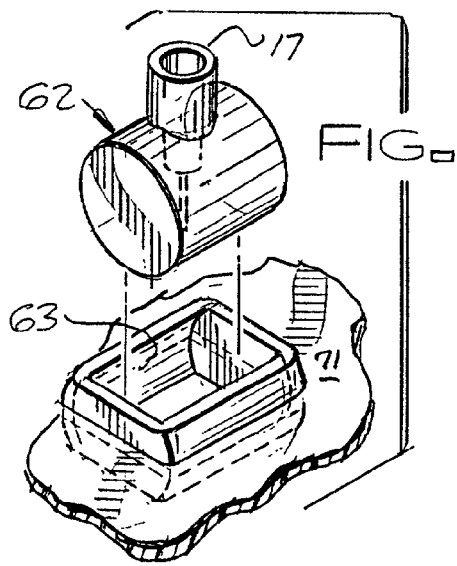
FIG. 19C is an exploded perspective view further illustrating the swivel detail of the embodiment of FIG. 19A.

FIG. 19A is a side sectional view of an alternate preferred embodiment of the splash shield 52 of the present invention, illustrating its operation incorporating an inlet swivel structure permitting better direction of impingement of the saline or other irrigating fluid 56, even for impinging along a wound length direction (as for wound 54). The details of the inlet swivel structure are best shown in FIGS. 19B-C. FIG. 19B is a partial expanded sectional view of the embodiment of FIG. 19A, illustrating swivel detail. FIG. 19C is an exploded perspective view further illustrating the swivel detail of the embodiment of FIG. 19A. As shown, inlet swivel 62 containing opening 17 rides and may rotate in swivel socket 63, which socket is fixed in place by fixed attachment with the distal end wall 71 of shield 52. When the tip 158 of syringe 55 is inserted into opening 17, the orifice nozzle 58 of inlet swivel 62 is enabled (see FIG. 19B) to direct fluid 56 into the splash shield as shown. The arrangements of FIGS. 18 and 19 embody herein wherein a bottom peripheral circumference of such body means has an oval-like shape, and an axis of maximum height dimension passes through about the center of such oval-like shape; and, further, wherein such input means comprises a swivel means for user-directing of a stream of irrigation fluid to selected portions of the skin of a patient, wherein such swivel means comprises attachment means for attaching a source of irrigation fluid to such swivel means; and, further, wherein such body means includes an essentially planar bottom opening, and such essentially planar bottom opening includes a relief portion structured and arranged for efficient release of irrigation fluid from such body means when desired by the user, wherein the ratio of a maximum length of such bottom opening compared to a maximum width of such bottom opening is at least 1.5:1.0.

FIG. 20A is a perspective view of a preferred embodiment of an alternate splash shield system according to the present invention, and showing use of splash shield 64 with an irrigation squeeze bottle 59. FIG. 20C is a sectional view of the embodiment of FIG. 20A, illustrating details of preferred structure. FIG. 20B is an exploded perspective view of the embodiment of FIG. 20A. Bottle 59 has male threads 72 capable of meshing with the female threads 69 of splash shield 64 to form a tight connection. Below this threaded connection, splash shield 64 has an internal shelf 81 sealing the open/bottom end of splash shield 64 except for orifice nozzle 58 for directing a stream toward flesh 53. It is noted, as shown in FIG. 20B, that one or more additional holes 201 may be optionally found going through shelf 81 in order to increase irrigation flow to a wound; and such hole or holes 201 will not alter flow through shelf 81 when, for example, a syringe is used to provide irrigation fluid directly to orifice 58. Thus, when bottle 59 is attached and squeezed, fluid 56 is forced into and through orifice nozzle 58 (and also, optionally, through optional hole 201), as shown. This arrangement embodies herein a splash shield system comprising: a transparent body means for assisting protecting a user from contact with irrigation fluid directed at a patient's wound, wherein such transparent body means is essentially hollow and essentially open at a first end of such body means and at a second end of such body means; an irrigation-source connection means for connecting such body means, adjacent a first end of such body means, to a source of irrigation fluid; and a shelf means for dividing such body means into a first hollow portion and a second hollow portion, such shelf means being located between such first end and such second end; wherein such shelf means comprises a directed-stream means for directing a narrow stream of the irrigation fluid towards the wound; and, further, wherein such shelf means further comprises, in addition to such directed-stream means, at least one hole through such shelf means. FIG. 20B also shows (in dotted lines) the structure of another preferred alternate embodiment using vacuum evacuation of irrigation fluid by vacuum line 10 through a port situated near (as shown) the plane of irrigation.

FIG. 51A is a sectional view of yet another preferred embodiment of a splash shield 64A according to the present invention, meshed with an irrigation squeeze bottle 59, illustrating details of preferred structure. Splash shield 64A comprises a puncturer 65 (embodying herein a puncturing means for puncturing a seal of the irrigation-fluid bottle when the threaded portion is tightened). As splash shield 64A is meshed with bottle 59, bottle membrane 59A is punctured by puncturer 65, which permits fluid to exit from bottle 59. Below the threads 69 of splash shield 64A is internal shelf 81 sealing the open/bottom end of splash shield 64A except for hole(s) 201. Preferably, puncturer 65 does not puncture bottle membrane 59A until after sufficient connection between the bottle 59 and the splash shield 64A is made to provide a sufficient seal preventing fluid from leaking from the meshed connection. Preferably, puncturer 65 punctures bottle membrane 59A when the meshed connection between splash shield 64A and bottle 59 is already engaged, but not yet fully and completely seated, preferably when the meshed connection is approximately half-way complete. Thus, when bottle 59 is attached and squeezed, fluid 56 is forced into and through hole(s) 201.

FIG. 51B is a sectional view of yet another preferred embodiment of a splash shield 64B according to the present invention, meshed with an irrigation squeeze bottle 59, illustrating details of preferred structure. Splash shield 64B comprises a puncturer 65B. As splash shield 64B is meshed with bottle 59, bottle membrane 59A is punctured by puncturer 65B, which permits fluid to exit from bottle 59. One or more fluid channel(s) 65C in puncturer 65B permits fluid 56 to exit from bottle 59 into orifice nozzle 58B (embodying herein wherein the puncturing means comprises at least one hole means for permitting fluid flow through the puncturing means). Below the threads 69 of splash shield 64B is internal shelf 81 sealing the open/bottom end of splash shield 64B except for orifice nozzle 58B for directing a stream toward flesh 53. It is noted, that one or more additional holes 201 may be optionally found going through shelf 81 in order to increase irrigation flow to a wound. Preferably, puncturer 65B does not puncture bottle membrane 59A until after sufficient connection between the bottle 59 and the splash shield 64B is made to provide a sufficient seal preventing fluid from leaking from the meshed connection. Preferably, puncturer 65B punctures bottle membrane 59A when the meshed connection between splash shield 64B and bottle 59 is already engaged, but not yet fully and completely seated, preferably when the meshed connection is approximately half-way complete. Thus, when bottle 59 is attached and squeezed (see FIG. 20A), fluid 56 is forced through the fluid channel(s) 65C and through orifice nozzle 58 (and also, optionally, through optional hole(s) 201), as shown.

Figure 20E:
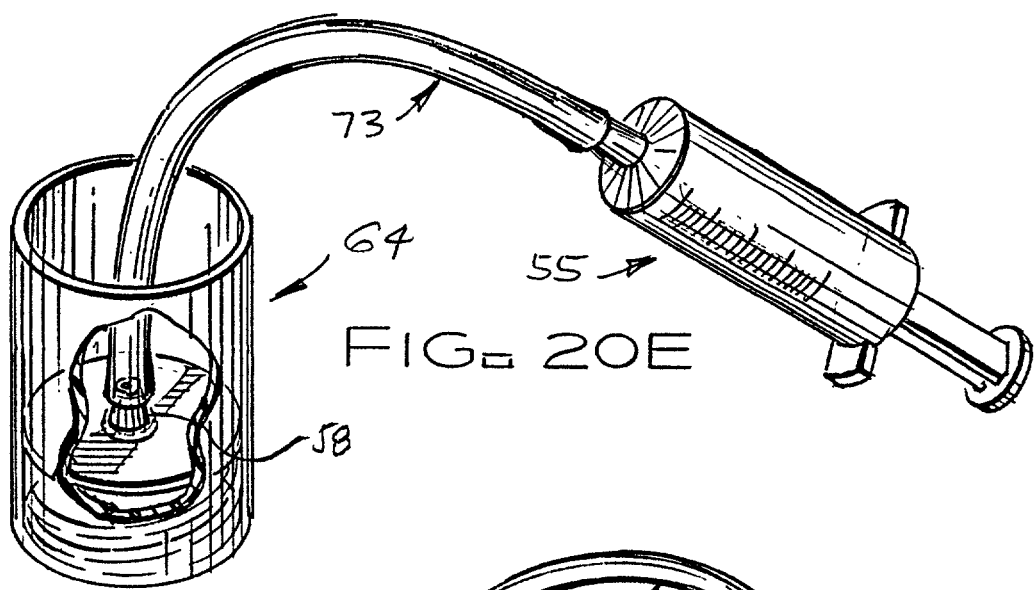
FIG. 20E is a perspective view illustrating the use of the splash shield of FIG. 20D using a syringe with connecting tubing.

FIG. 20D is a perspective view illustrating the use of the splash shield 64 of FIG. 20A inverted for use with a syringe 55. In this embodiment, the open unthreaded end of splash shield 64 receives a syringe 55 whose nozzle fits over the now protruding (from the former underside of shelf 81) part of orifice nozzle 58, as shown. Thus, when syringe 55 discharges its fluid, the threaded portion 69 of splash shield 64 now acts as a splash shield. This arrangement embodies herein a splash shield means for assisting containment of the fluid when dispensed from such dispensing end, wherein such splash shield means comprises a connecting means for holding such syringe-tip dispensing means, such syringe system being structured and arranged so that the fluid when dispensed from such syringe system may be contained by such splash shield means; and, wherein such syringe-tip dispensing means is constructed and arranged to provide a female connector for a male such connecting means. Similarly, FIG. 20E is a perspective view illustrating the use of the splash shield 64 "upside down" arrangement of FIG. 20D using a syringe 55 with connecting tubing 73, which tubing 73 is in this case connected over the protruding nozzle 58.

Figure 20F:
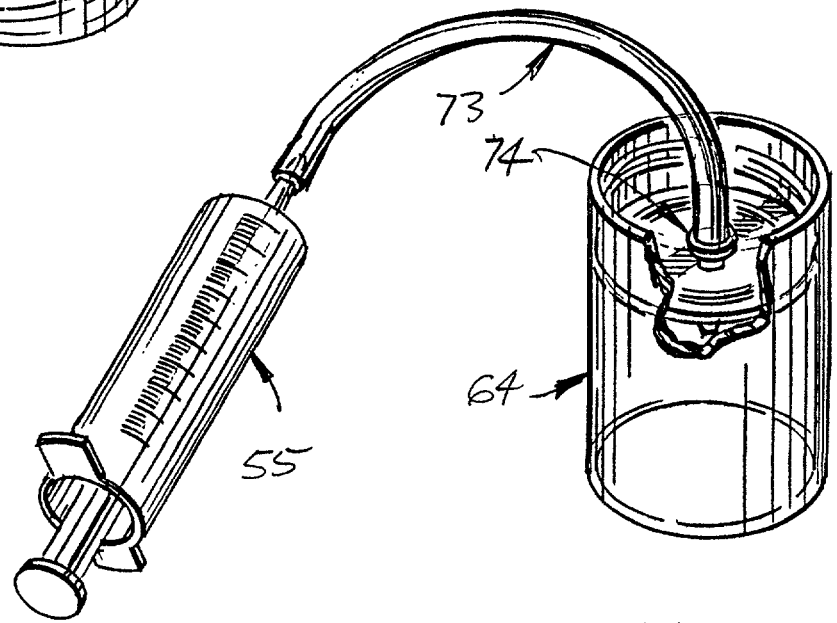
FIG. 20F is a perspective view illustrating the use of the splash shield of FIG. 20A using a syringe with connecting tubing and an adapter.
Figure 20G:
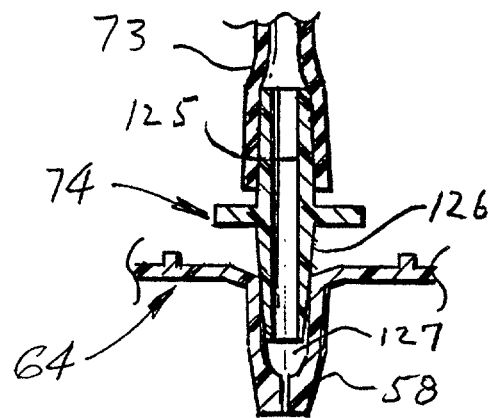
FIG. 20G is a sectional view of the adapter connection area of the embodiment of FIG. 20F illustrating the area detail.

FIG. 20F is a perspective view illustrating the use of the splash shield 64 of FIG. 20A using a syringe 55 with connecting tubing 73 and an adapter 74. And FIG. 20G is a sectional view of the adapter 74 connection area of the embodiment of FIG. 20F illustrating the area detail. As shown, tubing 73 fits over an upper male portion 125 of the adapter 74 while a lower male portion 126 of the adapter 74 fits within the upper hollow 127 of orifice nozzle 58.

The arrangements of FIG. 20 embody herein a splash shield system comprising: a transparent body means for assisting protecting a user from contact with irrigation fluid directed at a patient's wound; an irrigation-source connection means for connecting such body means, at a first end of such body means, to a source of irrigation fluid; wherein such body means comprises essentially a hollow round cylinder having essentially a hollow round-cylindrical inner hollow; and wherein such hollow round cylinder, at a second end of such body means, is open to such hollow and is constructed and arranged for contact with a patient's skin in such manner as to protect the user from contact with the irrigation fluid. Also so embodied herein are a source of irrigation fluid connected to such body means at a such first end of such body means. And further so embodied herein is such a system wherein such irrigation-source connection means comprises an adaptation means for adapting a connection between such body means and such source of irrigation fluid; and, further, wherein such adaptation means comprises variation means for permitting such adaptation means to connect such body means to multiple varieties of such source of irrigation fluid; and, further, comprising an adaptation means for adapting a connection between such body means and the source of irrigation fluid, wherein such adaptation means comprises variation means for permitting such adaptation means to connect such body means to multiple varieties of the source of irrigation fluid; and, further, comprising a body extension extending from such adaptation means in a direction away from such second end of such body means, wherein such body extension comprises essentially a hollow round cylinder; and, further, wherein such adaptation means comprises a directed-stream means for directing a narrow stream of the irrigation fluid towards the wound; and, further, wherein such connection means comprises thread means for providing a threaded connection with the source of irrigation fluid; and wherein such thread means comprises internal threads structured and arranged for connection with external threads on a neck of a bottle for containing irrigation fluid; and, further, comprising a bottle for containing irrigation fluid, such bottle comprising neck means, of the type having external threads, for connecting with a bottle cap.

FIG. 21A is a perspective view of the upper portion of a prior art a syringe 75. FIG. 21B is a side elevation view of the prior art embodiment of FIG. 21A. Syringe 75 is of normal construction and includes a plunger ring 77 at the plunger 91 upper end (as shown) and also includes a double-ringed cylindrical groove 76 at the upper end of the syringe body 90. In operation, as shown, the user may place two fingers 20 in groove 76 while pulling down the plunger 91 by using a finger 20 placed into plunger ring 77. Thus, the user is given the ability to use only one full-hand-length downstroke in order to dispense fluid from a syringe body.

FIG. 22 is a side elevation view of a preferred embodiment of the racheting syringe 78 of the present invention, illustrating a multiple-hole plunger 79. In operation, as shown, the user may pull down the plunger 79 by using a finger 20 placed into any plunger hole 100. Thus the amount of fluid dispensed by the plunger 79 may be determined by the number of multiple (as opposed to single, see prior art of FIG. 21) pull-down strokes made by a user. Thus, as shown, the arrangement of FIG. 22 embodies herein a syringe system comprising: syringe barrel means for holding a reservoir of fluid; syringe-tip dispensing means at a dispensing end of such syringe barrel means for dispensing a stream of the fluid; and syringe plunger means for forcing the fluid in such barrel means to be dispensed through such syringe-tip dispensing means as such syringe plunger means is moved in such syringe barrel means toward such dispensing end; wherein such syringe plunger means comprises a handle means, operable by a single hand of the user having a single-hand span, for gripping and moving of such syringe plunger means in such syringe barrel means toward such dispensing end; and wherein such handle means comprises spaced multiple gripping-point means for gripping operation by the single hand; and wherein such syringe barrel means is substantially longer than the single-hand span; and wherein such syringe system is structured and arranged for the dispensing of user-chosen variable fluid volumes depending upon which ones of such spaced multiple gripping means are successively gripped by the single hand and the number of times such syringe plunger means is moved toward such dispensing end, by the single hand, within such syringe barrel means. This arrangement also embodies herein such a system wherein such syringe barrel means comprises a support means for providing support to at least one digit of the user's single hand during movement of such syringe plunger means toward such dispensing end; and such spaced multiple gripping means comprise multiple holes in such handle means, each such hole being structured and arranged for gripping by a single digit of the user's single hand. And it embodies herein such a syringe system wherein such syringe barrel means has a small enough diameter to fit within a mouth of a typical supply bottle of irrigation fluid.

Figure 23A:
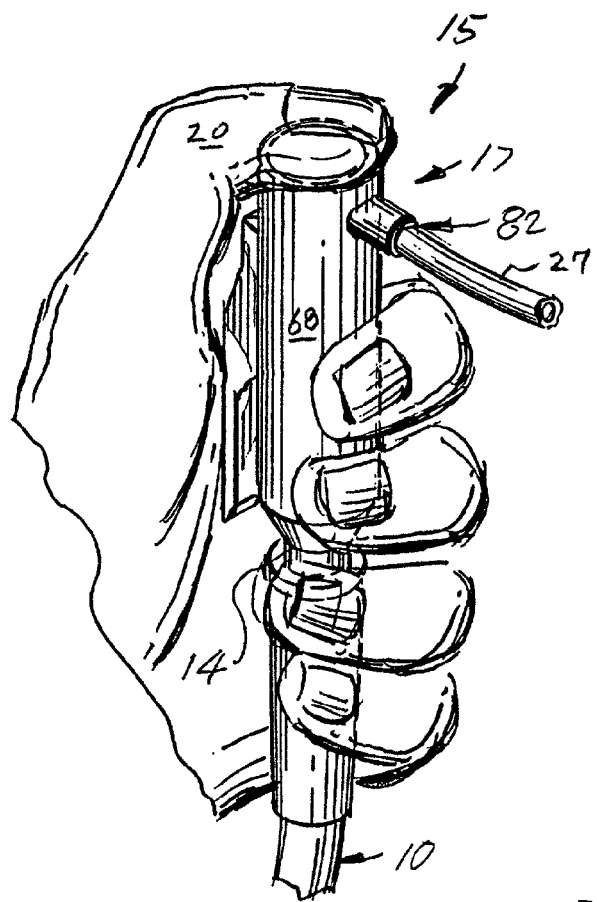
FIG. 23A is a perspective view of yet another preferred embodiment of a medical device according to the present invention, illustrating its operation as a suction device.
Figure 23B:
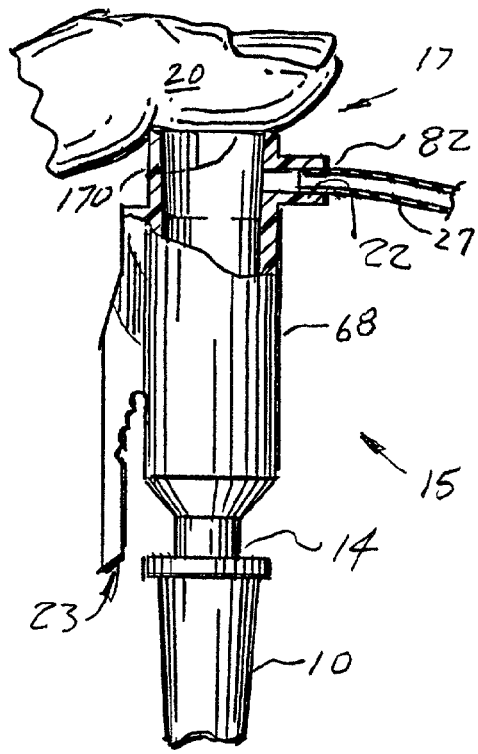
FIG. 23B is a side elevation view in partial section of the medical device of FIG. 23A.

FIG. 23A is a perspective view of yet another preferred embodiment of a medical device 15 according to the present invention, illustrating its operation as a suction device. Side inlet port 82 is located near the distal end 17 of the device 15. Proximal outlet end 14 may be attached to vacuum line 10 for suction use. Cylindrical body 68 is open at its distal end and some flow control may be had by the user using a finger 20 to wholly or partially occlude this distal opening 170 of body 68. FIG. 23B is a side elevation view in partial section of the medical device 15 of FIG. 23A, showing the internal taper of the inlet port projection 22 of inlet port 82, within which a suction catheter 27 may be affixed by friction or by bonding, as shown.

Figure 23C:
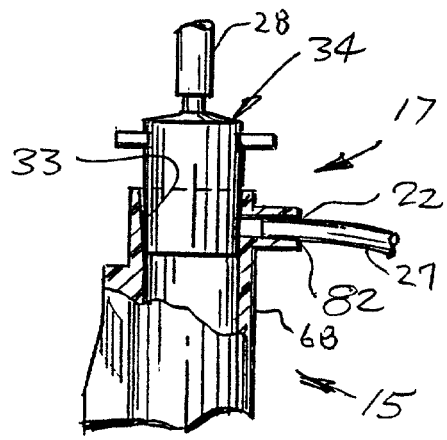
FIG. 23C is a side elevation view in partial section of the top portion of the medical device of FIG. 23A illustrating the detail of the connection of an endotracheal tube adapter which blocks the former suction inlet.
Figure 23D:
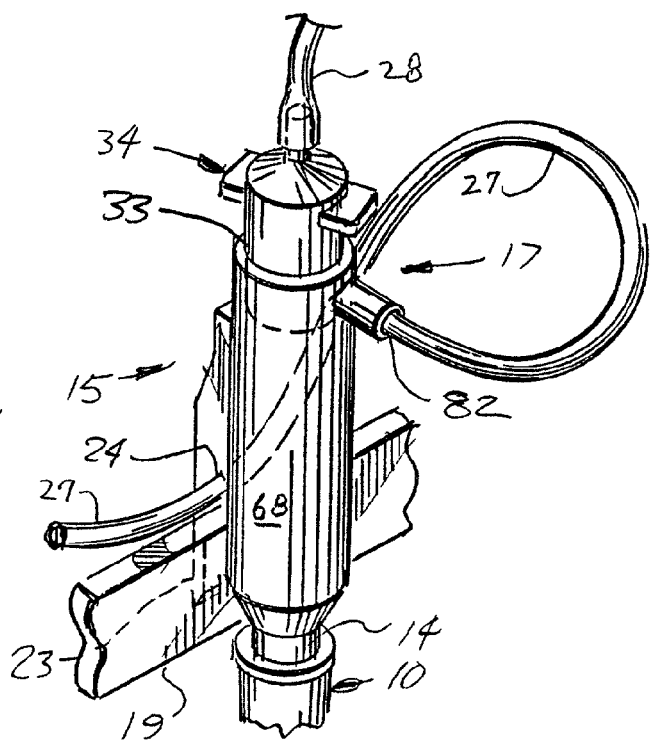
FIG. 23D is a perspective view of the combined medical devices of FIG. 23C and further illustrating retaining of the unused tubing and of the entire device.

FIG. 23C is a side elevation view in partial section of the top portion of the medical device 15 of FIG. 23A illustrating the detail of the connection of an endotracheal tube adapter 34 within the opening 33 (internally tapered to accept a fit with endotracheal tube adapter 34) at the top of body 68, which blocks the former suction inlet 82 (as shown). This efficient blocking permits the connection of the endotracheal tube 28 to, say, a respiratory device by way of line 10. FIG. 23D is a perspective view of the combined medical devices of FIG. 23C and further illustrates retaining of the unused tubing 27 in tubing restraint 24 and of restraint of the entire device by the hanging of clip restraint 23 on a portion of nearby equipment 19.

FIG. 24A is a perspective view illustrating the use of a preferred embodiment of the combined light and tongue depressor 83 of the present invention, illustrating its use in the intubation of an infant 84. With respect to the discussion herein of the problems of the prior art and the needs of medical personnel, it is further noted generally that such a device is preferred to have a flat planar light source that reduce visual obstruction and could accommodate a spatula such as a tongue depressor to move the tongue and epiglottis out of the way to view the insertion point of the vocal cords. Such a device would be most useful with, but not limited to, smaller patients whose body structures have less mass and therefore could be more easily manipulated with the preferred materials, and would therefore provide pediatric personnel with a constantly available resuscitation device.

Referring again to the drawings, FIG. 24B is a top perspective view of the embodiment 83 of FIG. 24A. FIG. 24C is a bottom view of the embodiment 83. FIG. 24D is a partial exploded perspective view of the bottom of the embodiment 83. The light source of embodiment 83 is a flat flashlight 87 of the type available commercially and having a pressable area 89 on its top side 93 which operates its on/off switch and a bulb 88 at its front to provide the illumination, the batteries being hidden within the flat flashlight 87. Tongue depressor 92 is of the usual type and is carried by the flashlight 87 by the friction insertion and holding of the tongue depressor 92 within a pocket 95 on the bottom side 94 of the flashlight 87. The tongue depressor can act as a blade for moving the oral structures of the mouth and pharynx in order to visualize the vocal cords of a patient for intubation, particularly for a smaller pediatric patient. It can therefore form a simple disposable laryngoscope that is hand-held, disposable, easy to store in a pocket and simple to assemble and reload with a clean tongue depressor. As earlier pointed out, oral visualization with inexpensive disposable equipment including use for oral sampling and possibly intubation usually required one hand to hold a device such as a culture swab or endotracheal tube illuminator and one hand to use the tongue depressor, leaving no convenient or efficient way to light up the area being worked in to get a better, less obstructed, and more illuminated view. By combining in the manner of embodiment 83 both the flat/planar flashlight 87 and the tongue depressor 92 in such manner as to require only one hand 86 to hold the combined devices, the other hand 86 (as shown) is free for the sampling or intubation process, shown in FIG. 24A as the manipulation of element 101, representing an endotracheal tube with a stylet in the tube to provide added stiffness, a process well known in the art. This combination of devices provides an easily stored, inexpensive and disposable device for illuminating the oropharynx with a minimum of visual obstruction caused by the illuminator itself as well as the oropharyngeal structures. In addition, FIG. 24A shows a left handed approach to intubation, (with the endotracheal tube held in the users left hand) demonstrating the versatility of this device which permits users to use either a left handed or right handed approach. This is in contrast to the expensive standard metal laryngoscopes which have a single sided (usually right hand) preference.

FIG. 24E is an end elevation view of the embodiment 83 of FIG. 24A showing the pocket opening 95 and the location of the cross-section of the tongue depressor 92 in pocket opening 95, adjacent the bottom side 94 of flashlight 87. It is noted that the arrangement of FIG. 24 embody herein a such first separate user-hand-held-type medical component that comprises a lighting means for providing a directed beam of light, and further embody herein that such lighting means comprises a thin flat structure arranged to include a battery and a battery operated light-emitter, and further embody herein that such restraint means comprises a pocket means for holding such flat device in slidable engagement with such thin flat structure, and wherein such flat device comprises such tongue depressor means.

FIG. 25 is a perspective view of an alternate preferred embodiment of the light system of the present invention. As shown, flashlight 87 has within pocket opening 95 on its bottom side 94, rather than the tongue depressor 92 of FIGS. 24A-E, a data card 104, which provides the type of reference material which might be desired in a medical device. The data card may be moved by the user so that various data are in line with lines or edges 144 to assist in data reading. The arrangements of FIGS. 24 and 25 embody herein that such second such user-hand-held-type medical component comprises a flat device selected from the group consisting of a tongue depressor means for depressing a patient's tongue, and an indicia means for providing information to a physician.

FIG. 26 is a perspective view of yet another alternate embodiment of the light system of the present invention, illustrating flashlight 87 modified on its bottom side 94 to provide a narrow pocket 96 just slightly wider than a tongue depressor 92. This arrangement is preferable to the present wider pocket in that the tongue depressor 92 (or a data card 104) may be held in a more stable way, with less "wobble" potential, and more tightly, thus providing a more efficient tongue depressing/lighting system.

FIG. 27A illustrates the use of a light system 83 according to the present invention, as used for a pediatric (or adult) eye examination. The physician's hand 86 is shown holding system 83 with the bulb 88 and the top side 93 of flashlight 87 to the front side, whereby the shadow cast by the tongue depressor 92 (or similar card, etc.) keeps the light emitted by bulb 88 off the far side of the face of child 84. The illuminated area 98 includes the near-side eye 102 of child 84 with the illustrated system providing a clear, non-fuzzy transition line 103 between the illuminated area 98 and the non-illuminated area 99. This system assists the physician in obtaining a distinct and controllable "on/off" of light to the eye, well known in the art to be desirable to determine the afferent and efferent pupillary constriction and dilation response of the eyes to light. The far eye 102 may be similarly exposed to illumination by turning embodiment 83 to place the bulb 88 to the far side of depressor 92 and turning on the bulb.

FIGS. 27B and 27C illustrate further the advantages in use of the light system of FIG. 27A in achieving a clear light transition line 103 from above or below simply by appropriately turning the embodiment 83 so as to place the bulb 88 above the depressor 92.

FIG. 28A is a top plan view of a preferred embodiment of the cough shield medical device 202 of the present invention. Cough shield 202 mounts on a tongue depressor 92 or similar device and is preferably made of a transparent plastic material. The shape is preferably as shown for reasons that will become apparent. As shown, adhesive 203 is placed on middle attachment flap 206, first side attachment flap 207, and second side attachment flap 208. FIG. 28B is a partial top plan view further illustrating the embodiment 202 of FIG. 28A and showing an adhesive protector/shield 204 sized to fit over and protect adhesive 203 areas. A pull tab 205 is part of the protector 204 (for ease of the protector removal when a user wishes to use the adhesive-coated areas).

FIG. 28C is a perspective view of the embodiment 202 of FIG. 28A in position (adhesive areas 203 pointing downward) above a tongue depressor 92, after removal of the protector 204, to install shield middle attachment flap 206. This middle flap 206 is pressed downward onto an area 127 (shown in dotted lines) roughly in the middle of depressor 92 so that flap 206 adheres. FIGS. 28D, 28E, and 28F are perspective views further illustrating the preferred installation steps to install the illustrated preferred cough shield 202. After middle flap 206 has been adhered, first side attachment flap 207 is pressed on top of middle flap 206 to adhere it; and then second side attachment flap 208 is similarly pulled over into place above the adhered elements 206 and 207 and pressed down to adhere flap 208 to flap 207, as shown in the resulting configuration detail of FIG. 28F.

FIG. 28G is a top plan view of the illustrated preferred cough shield 202 in pediatric use. It is seen that the mouth 85 of child 84 is shielded from the physician using tongue depressor 92 by means of the intervening cough shield 202 mounted on depressor 92. FIG. 28H is a side elevation view of the illustrated preferred cough shield 202 in pediatric use, illustrating how the position of the cough shield 202 on depressor 92 effectively stops germs and debris emanating from mouth 85 during a cough. FIG. 28J is a perspective view of the illustrated preferred cough shield 202 ready for use in combination with the preferred light system 83 of this invention. It is noted that use of these combined medical devices makes even more efficient the intubation process. And it is noted that the transparency of cough shield 202 assists the physician with viewing, e.g., during the intubation process illustrated in FIG. 24A. It is also noted that such a transparent shield as described could be used in combination with other medical devices such as a syringe to provide similar cough protection as during a tonsillar aspiration. The same device can also be attached on a syringe to provide other functions such as irrigation spray protection as a wound is infiltrated under pressure, with the flexible plastic shield forming alternatively a concave or convex shield depending on the positioning to which the shield is bent. The arrangements of FIGS. 28A-J embody herein a cough shield system comprising: a cough shield means for supplying a cough shield to a component of medical equipment; such cough shield means comprising a thin, transparent, portion of a plastic material; such cough shield means comprising at least one attachment means for attaching at least one selected location of such portion to another selected location of such portion; and such cough shield means comprising at least one connection means for connecting at least one selected location of such portion to such component; wherein such cough shield means is constructed and arranged in such manner that use of such attachment means and such connection means will result in the supplying of a cough shield to such component; and, further, wherein such component is a tongue depressor; and, further, wherein such attachment means comprises an adhesive, and such connection means comprises an adhesive; and, further, wherein such cough shield means is constructed and arranged for selective use in a concave or convex position.

The same device of the cough shield, as above noted, could also be used to attach to another component such as a syringe for the purpose of acting as an infiltration splash shield. One usually infiltrates a wound with a needle and syringe correctly by removing the needle while simultaneously using a high pressure counteracting force to infuse the medication, such as a local anesthetic into a wound. And it is the common safer practice to inject medication after a needle is inserted into the skin; then the syringe plunger is pulled back to create a negative pressure to make sure that one does not withdraw blood; this would indicate that one is undesirably in a blood vessel rather than in the desired location of being in the upper-layers skin tissue itself where the nerve endings are located. After such determination is made that one is not in the blood vessel, one then forces the medication through the needle into the skin while withdrawing the needle. This requires the use of a high pressure to infiltrate the closed space of the skin with the infused medication, requiring greater attention to the force being instilled and the forward pressure of the syringe and the counteracting withdrawing forces of pulling out the needle. In addition, as a great force is often required, the hand-held system is often less stable. As the needle is being removed, the position of the open tip portion of the needle position cannot be reliably visualized as it is under the skin. Often, as the needle is fully withdrawn from the skin, the continuing high pressured medication continues and sprays the medication into a patient's bloody wound, displacing not only the medication in an uncontrolled spray-like fashion, but also the patient's bodily fluid. This creates a health hazard to medical personnel as well as increasing cleanup time and soiling hospital equipment and patient clothing. Some medical personnel put on costly, cumbersome and time-consuming face masks with shields and gowns for protection during such a procedure. Others place their hand over the site which obstructs the sight and places their hand in close proximity to the potentially hazardous free end of the injecting needle. Having a simple inexpensive shield that could work in combination with such a syringe and needle system would be desirable. Having a device system that could also attach to other devices for other protective functions such as attaching to a tongue depressor to act as a cough shield would provide more versatility and increase the potential marketability and success of the device. Having a device with a means of attachment to another device would eliminate the number of hands and operators necessary to achieve the desired function or procedure. Having such a device with an easy simple attachment would speed the completion of the procedure as would desirable in a busy doctor's office. Having such a device that is easy to use and inexpensive to manufacture and therefore to sell would increase the use of the device and therefore reduce the potential contamination of hospital personnel from patients. Having a transparent material would allow visualization through the shield. Having a flexible material might allow for a nonplanar attachment of an otherwise flat material. Having an attachment of flexible material on a convex surface would increase the rigidity of the material and would stabilize other portions of the material bent in a concave fashion. Having a stable material bent in a concave fashion would permit a relative narrow attachment surface to accommodate a relatively larger concave bent surface to act as a splash shield. By varying the position of the bend, one could vary the angle and position of the shield. Such a large bent splash shield would protect the operator behind the shield and would not interfere with the forward advancement of the needle. Since the shield must extend beyond the syringe and preferably cover a large area, having a bent shield would facilitate such an operation without the shield edge obstructing the advancement of the needle tip below. Such a shield could be made of an inexpensive flat flexible material with at least one attachment means and could be used for other functions as well, such as a cough shield on a tongue depressor. Such a preferred shield would be relatively simple, inexpensive to manufacture, increasing the marketability and usage of the device for its desired advantages. The same principles described above could be related to other components and procedures such as wound irrigation without a needle.

FIG. 28A shows attachment of a shield to a medical component. If the component were instead a syringe such as the one pictured in FIG. 44A, and the shield had at least one attachment means as pictured, the shield could then be attached to the component and used as described above. Attachment of the shield over a convex surface, and bending the shield back as shown in FIG. 28H would permit the flexible plastic to retain a non-obstructing desired curved position extending beyond the tip of the syringe. The angle of the shield could be adjustable and positioned according to user preference. Similarly, such shields could be preformed in a the desired configurations, though this would be more complicated and expensive to make, and would be less likely to facilitate the multiple positioning. It would save time in attachment to specialized components, for example, a handheld otoscopic illuminator used for both otoscopic and oral illumination.

FIG. 29A is a perspective view of a preferred embodiment of the clip-on restraint 42 of the present invention, illustrating its attachment to a tube or other medical device 106, and further showing the clip restraint 23 of clip-on restraint 42 in restraint position clipped on a portion of nearby equipment 19. FIG. 29B is an expanded perspective view of the embodiment 42 of FIG. 29A, showing the details of its structure.

FIG. 30A is a perspective view of an alternate preferred embodiment of a meconium aspirator medical device 39 of the present invention; and FIG. 30B is a sectional view further illustrating the detail of the embodiment 39 of FIG. 30A. In this embodiment, similar to the embodiment of FIGS. 15A-B, the upper flow control port 16 is provided with a tactile feedback system for enhanced flow control. The upper surface portions around port 16 are stepped in two planes, thus providing a lower plane 109, a ledge which acts as a tactile marker 107, and an upper plane 108. The tactile marker 107 is preferably located at about the center of the circular portion of port 16. For finer control as the suction force is made higher, an extension 110 of port 16 is provided (beyond the upper portions of such port in the embodiment of FIGS. 15A-B). Extension 110, as shown, comprises a narrow slot in upper plane 108, the base of which slot slopes downwardly toward the center of the circular-cylindrical portion of port 16. This arrangement embodies herein a medical system for regulating suction, comprising: a user-hand-held-type medical component structured and arranged for use in a suction system and comprising at least one external aperture means for regulating suction; wherein such aperture means comprises single-finger-operable valve means for repeatable incremental user control of suction-vacuum variation in such suction system, wherein such valve means comprises (1) a primary aperture portion structured and arranged for regulating primary suction, and (2) a secondary aperture portion structured and arranged for regulating fine relief suction, wherein such secondary aperture comprises a slot; and, further, wherein such aperture means further comprises tactile feedback means for amplifying tactile feedback to a user to enhance distinguishing of control increments.

FIG. 31A is a sectional view of yet another alternate (and highly preferred) embodiment of the meconium aspirator 39 of the present invention, further illustrating its combined use as a combined device 150 with a preferred embodiment of an endotracheal tube adapter 152, which arrangement embodies herein that such first and second such medical components are structured and arranged for substantially more medical-procedure control when interattached for such combined medical use than when used separately without such combined medical use. The differences between this embodiment and the embodiment of FIGS. 30A-B are as follows. In this embodiment, the flexible membrane cap 45 is removed. And the opening usually covered by cap 45 is here internally tapered with internal taper 154 on the female side to accept a friction fit with an endotracheal tube adapter 152 (shown here inserted and in place) which is matchingly externally tapered with external taper 153. It is seen that, when adapter 152 is so inserted, it occludes inlet port 17 so that the new inlet port (of the combined device 150 shown) becomes the proximal end of the endotracheal tube 151. This arrangement embodies herein an endotracheal tube adapter having a proximal end connected in such third inlet means, whereby such first inlet means is blocked. As shown, the upper portions of the combined device 150 work the same way as discussed with reference to the embodiment of FIGS. 30A-B.

It is noted that FIG. 31A illustrates the insertion of an endotracheal tube adapter 152 into the distal opening of suction device 39. By having the control valve in line with the opening, the device has a number of advantages over prior art as will be illustrated in reference to meconium aspiration. One of these examples is that a stylet can be inserted through the control valve opening 16 when devices 152 and 39 are assembled. Based on current practice, most would chose to intubate the patient first with an endotracheal tube, with or without a stylet, and then assemble this to the suction device, but the combined configuration desired here would enable them to also use a stylet. This added capability would make the device more marketable. In addition, after the assembly is made, the preferred relatively perpendicular configuration of inlets to outlet has other advantages. By having these inlets in a preferable relatively perpendicular configuration in relation to the suction outlet, the device is in a more ergonomic position for attachment of the suction device over an endotracheal tube. As the patient is on the back during intubation, and the endotracheal tube is inserted vertically and the suction tubing is coming generally from a source located horizontally, having the aspirator configured with the outlet opening perpendicular to the inlet has certain ergonomic advantages. The suction control port 16, located in line with the endotracheal tube 151, will always be in a central axial position and therefore easy to locate in the midst of a chaotic resuscitation. Prior art such as the Neotech Meconium Aspirator includes having the suction control port located perpendicular to the endotracheal tube adaptor inlet, with the outlet in line with the endotracheal tube adaptor. This requires the vacuum hosing to be looped up vertically for connection. This is cumbersome and requires a significantly greater length of tubing to be pulled to accommodate this maneuver with increased force which increases the chance that the device will disconnect inadvertently from the vacuum hose, or at least that an increased amount of attention must be paid to maintaining it. The configuration of the present invention does not require such a vertical looping of the vacuum hose and is therefore more stable and easier to attain. In addition, as previously mentioned, the preferably in-line control port 16 is in a consistent central axial position. The prior art described above has the side control port perpendicular to the endotracheal tube adaptor inlet and, upon connection, the control port might be located unpredictably in any plane of the 360 degree circumference. Such an in-line configuration also is a design which is easier to manufacture than prior art such as my own prior invention where the endotracheal tube adapter inlet was also parallel to the optional control inlet, yet in an offset position. Having this in an in-line position allows a single core pin to create both apertures in an injection molding process and therefore this combined device 150 in a unitary form can be made with less expense, therefore increasing the chances of marketing the device to achieve its medical advantages.

Such illustrated configuration also facilitates the other advantages of a suction catheter inlet 17 in the preferred relation to the seal line 155 (i.e., the seal line against which adapter 152 is sealed in its contact with device 39 to effectively block off inlet 17), as illustrated, and resembles the proportions of standard suction devices to make the device more marketable. This seal line arrangement embodies herein that such body means is, internally, substantially cylindrical in shape, and such body means comprises a circumferential internal seal means for making a seal with an endotracheal tube adapter when such adapter may be attached in such third inlet means, wherein such seal means is located proximally from such first inlet means.

Such illustrated configuration also facilitates the placement of the inner control aperture 46, with the cylinder formed by its sidewalls, as illustrated, which provides numerous advantages such as to prevent splash on the finger to increase the surface area for trapping specimens, for acting as a position marker for variable suction based on pressure and lateral and vertical positioning of the controlling finger or cap, and for acting as an attachment point for a self sealing cap mechanism. Yet though these additional features are all advantageous and desirable, they may be seen by some as too complicated. Certain medical personnel, particularly when performing a meconium aspiration resuscitation may only desire a simple suction device with or without the optional second suction inlet 17, or variable suction features 110 and 117, or inner control port 46, or restraint 23 and this too, for the reasons enumerated above, would remain a desirable form of the device. It is noted that the arrangement of FIG. 31A also embodies herein a medical component comprising: first outlet means for attaching a vacuum source; a body means for transporting air from inside such body means to such first outlet means; first inlet means for attaching a suction catheter to such body means; and second inlet means for providing assistance in regulating air flow into such first inlet means; wherein such body means comprises a round cylinder portion having a central axis and such first and second inlet means are disposed along such central axis; and, further, wherein such first inlet means is structured and arranged for attaching a second medical component in line with such central axis.

FIG. 31B is a perspective view of the discussed combined system 150 of FIG. 31A illustrated in a restrained position and ready for use. The meconium aspirator device 39, connected to suction catheter 27, is shown restrained by its clip restraint 23 to a portion of nearby equipment 19. The endotracheal tube adapter 152, connected with endotracheal tube 28, is being restrained by having tube 28 within the tube restraint 24 on device 39 (such arrangement embodying herein a third restraint means on such first separate user-hand-held-type medical component for temporarily restraining, without substantial interference with normal use of such medical device, at least one second such separate user-hand-held-type medical component in a position adjacent such first separate user-hand-held-type medical component for ready availability for potential use by the user).

FIG. 32 is a perspective view of a prior art specimen trap 162. As shown, during specimen collection, vacuum line 10 is connected (by way of tubing) to container 163. A suction catheter 27 is also connected to container 163. The specimen may then enter container 163 from suction catheter 27, but specimen remains within container 163 since the vacuum suction to vacuum line 10 does not pull all the specimen out of container 163. The container 163 (e.g., a bottle) may then be removed from the top unit 167 (along with attached tubing) and capped so that the container 163 and the trapped specimen may be sent for sampling. A cap 164 may be placed on the container 163 for capping. The cap 164, when not in use, may be stored on the container bottom 166, as shown. Often, a filter 168 is placed in the tubing to the vacuum line 10 to prevent debris from entering the vacuum system. Although such a filter is not specifically shown herein in the views of the embodiments of the present invention having a vacuum line, it is to be understood that a filter may be incorporated without deviation from the present invention.

FIG. 33A is a perspective view of even yet another preferred embodiment of a meconium aspirator of the present invention structured for specimen collection and including an illustrated special cap 176 for use in the collection system. Meconium aspirator 39 is as described with reference to FIGS. 30A-B. In FIG. 33A, cap 176 is shown detached from aspirator 39, and in FIG. 33B, cap 176 is shown attached in a similar manner to cap 45 (see FIG. 33B). When flow control port 16 is open, the air flow is as shown by the arrows in FIG. 33B and there will be no meconium suction, as will be understood by those skilled in the art from the teachings in this specification; thus FIG. 33B is a sectional view illustrating the bottom portion of the embodiment of FIG. 33A with open-valve relief and no meconium suction.

FIG. 33C is a sectional view similar to that of FIG. 33B but with closed-valve full-flow suction of meconium, i.e., port 16 is closed and meconium 175 is entering aspirator 39 by way of inlet 17 from catheter 27. To temporarily close port 16 from its bottom end (in accord with prior teachings herein), special cap 176 is used. The features and structures of special cap 176 include the following: (1) it is preferably made of a very flexible material, enough so that it can not only fit its outer internal ring over the bottom opening of aspirator 39, but so that a user may, by pushing a finger at the bottom center of cap 176, either temporarily close port 16 (see FIG. 33C) or seal port 16 by snapping on to said bottom opening; (2) it should include a flow-control-metering flange 177 for desired abutting of the inside of cap 176 with said opening; and it should include a sealing socket 178 (see FIG. 33D) for sealing port 16 when a user pushes the outside bottom center of cap 176 until it "snaps" into a sealing relationship (all as shown). This design would also give the new and desirable incremental variation of flow control as previously described, as well as providing a simple means for controlling flow in a constant, reversible on/off regulation not requiring constant application of pressure by a finger.

FIG. 33D is a sectional view similar to that of FIG. 33B but illustrating the aspirator 39 after use with the flow-control port 16 sealed for containment of collected specimen 175. Such sealed device is preferably sterile to prevent the introduction of infection to a patient and to allow the accurate collection of a microbiology specimen, for example. It is preferably made of a transparent plastic material such as a transparent PVC or polycarbonate material and preferably of a medical grade standard for the industry. Having transparent properties allows the suction catheter to form a readily available compact specimen visualization trap with an increased surface area for routine and specialized suction procedures. Such transparent traps of the prior art are currently bulky cumbersome attachments that are not integrated into the compact suction valve apparatus as disclosed in this invention. Nor do they have the novel self-containment closing features of the cap 176. Such features are enhanced in combination with the self-containment features shown in FIGS. 33E-34C. Such self-containment apparatuses can reduce the need for extraneous caps and closure devices that can be more costly to manufacture and package as well as increase the risk of contamination during transfer or assembly.

FIG. 33E is a perspective view of the described collection system of FIGS. 33A-D, illustrating the inlet tube 27 connected to the outlet port 14 (by a user) so as to fully seal collected specimen 175 for sending to the lab. FIG. 33F is a partial view, partially in section, of the outlet port 14 area of the aspirator device 39 of FIG. 33E showing the detail of the structure for insertion of the inlet tubing 27. The arrangements of FIGS. 33D-F embody herein that such body means contains a suction-collected medical specimen and wherein such cap means is sealing such third inlet means and such second aperture means, and further comprising a sealed connection between such first outlet means and such first inlet means, whereby such suction-collected medical specimen may be safely sealed within such body means for transport, and wherein such sealed connection comprises flexible tubing and Luer adaptors for connecting such flexible tubing.

Figure 34A:
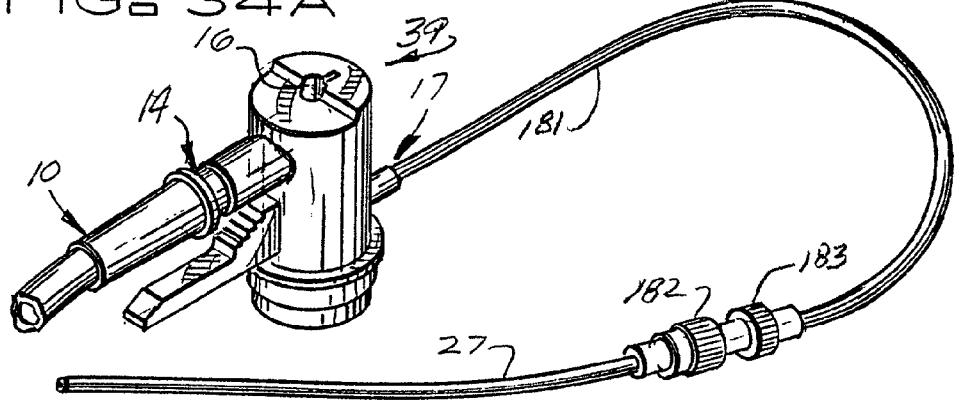
FIG. 34A is a perspective view of the meconium aspirator embodiment of FIG. 33A and further showing the inlet tube with a Luer Lock connector attached to a catheter.
Figures 34B, 34C:
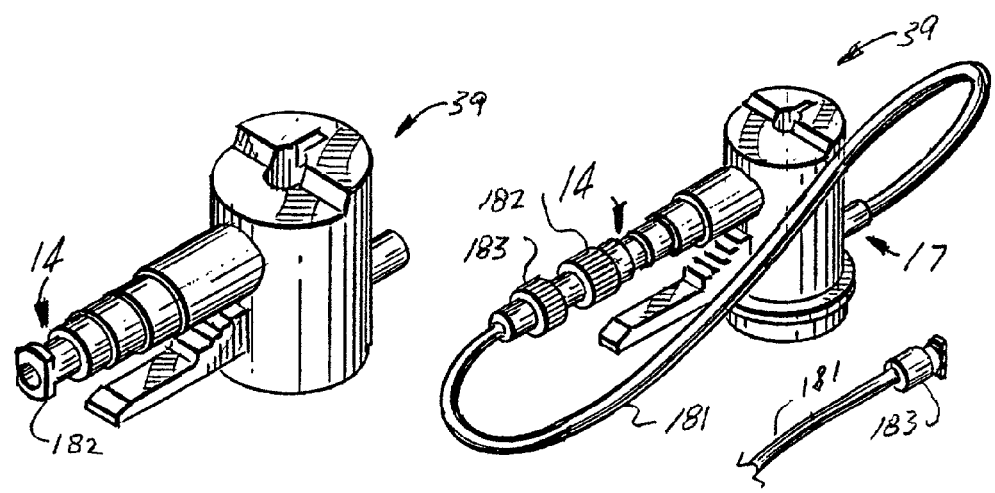
FIG. 34B is a perspective view of the embodiment of FIG. 34A shown with a Luer Lock connector on the outlet port.
FIG. 34C is a perspective view of the embodiment of FIG. 34B, further showing a Luer Lock connector on the inlet tube, which is attached to a Luer lock connector on the outlet tube for fully sealing a specimen for sending to a lab.

FIG. 34A is a perspective view of the meconium aspirator embodiment 39 of FIG. 33A and further showing an inlet tube 181 with a Luer Lock (hereinafter sometimes called "LL") connector, of the type very familiar to those with skill in this art, attached to a catheter 27. Preferably a male LL connector 183 on the distal end of tubing 181 is connected with a female LL connector 182 on the proximal end of catheter 27. The advantages of LL and Luer connections without the locking mechanism are well known to those in the medical field. FIG. 34B is a perspective view of the embodiment 39 of FIG. 34A shown with a Luer Lock connector 182 on the outlet port 14. FIG. 34C is a perspective view of the embodiment of FIG. 34B, further showing a Luer Lock connector 183 on the inlet tube 181, which is attached to the Luer lock connector 182 on the outlet port 14 for fully sealing a specimen 175 for sending to a lab.

Figures 35A, 35B:
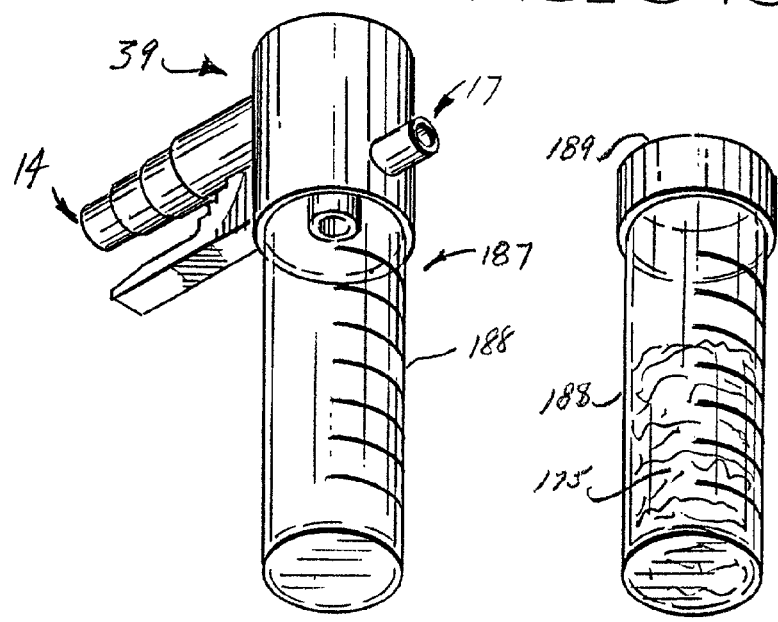
FIG. 35A is a perspective view of a meconium aspirator similar to the embodiment of FIG. 33A, further illustrating a large specimen container in place of the bottom cap (FIG. 33A).
FIG. 35B is a perspective view of the large specimen container of FIG. 35A, shown removed from the meconium aspirator and sealed with its own cap for sending to a lab.

FIG. 35A is a perspective view of a meconium aspirator 39 similar to the embodiment of FIG. 33A, further illustrating a large specimen container 188 in place of the bottom cap 176 (FIG. 33A) to provide a bottle trap system 187. Note that container 188 preferably fits, at its upper end, within the bottom opening of device 39. Also note that, when using the bottle trap system 187, cap 176 is not used. FIG. 35B is a perspective view of the large specimen container 188 of FIG. 35A, shown removed from the meconium aspirator 39 (after specimen 175 collection) and sealed with its own cap 189 (as shown), preferably female, for sending to a lab. This arrangement embodies herein a removable cylindrical specimen trap having an open end connected in such third inlet means, such open end of such cylindrical specimen trap being structured and arranged to be sealed by a such cap means. It is noted that the additional versatility of this invention embodiment over the prior art has been illustrated in that the same suction catheter valve assembly can be used in a number of configurations either alone or in combination with other devices to obtain and contain a specimen of various maximal sizes. Either a small sample can be collected and transported in a self-contained device, as illustrated in FIG. 34C for example, or a larger sample can be optionally collected in combination with a larger trap, as shown in FIG. 35. It is noted, as shown in FIGS. 30-35, that device 39 embodies herein a first such user-hand-held-type medical component comprising: first outlet means for attaching a vacuum source; a body means for transporting air from inside such body means to such first outlet means; first inlet means for attaching a suction catheter to such body means; second inlet means for providing assistance in regulating air flow into such first inlet means; and third inlet means for attaching a second user-hand-held-type medical component selected from the group consisting of an endotracheal tube adapter, a specimen trap, or a cap means for temporary sealing of such third inlet means; wherein such second inlet means is structured and arranged to assist a user to obtain repeatable incremental flow variation. And it further embodies that such body means comprises a round cylinder portion having a central axis, and that such third inlet means is structured and arranged for attaching the second user-hand-held medical component with such round cylinder portion in line with such central axis. Further, with reference to FIG. 35A, it is noted that a source of irrigation may be connected by one skilled in the art to inlet port 17 and that cylinder 188 may have its bottom open for use as a splash shield, such arrangement embodying herein a source of irrigation connected with such first inlet port, whereby such third inlet means may perform as a splash shield when irrigating skin beneath such third inlet means, and further comprising a cylindrical extension connected with such third inlet means, thereby providing an enlarged splash shield.

FIG. 36 is a perspective view of a prior art endotracheal tube adapter 34. As stated in the prior art summary earlier, the shapes and sizes make it difficult to grasp, twist and pull in desired ways; and there may be a large unwanted volume in the interior cavity, tending to make a less efficient air changer.

FIG. 37A is a perspective view of a preferred embodiment of an endotracheal tube adapter 192 according to the present invention. FIG. 37B is a sectional view of the embodiment 192 of FIG. 37A further illustrating detail. Both the flange 193 and the interior design (see FIG. 37B) are improvements to the prior art endotracheal tube adapter 34. The proximal outlet end 14 of endotracheal tube adapter 192 includes a sump structure 191 which is a surface which both separates the interior of adapter 192 from outlet end 14 and also gradually (as shown) becomes part of the internally tapered inlet end 17 of adapter 192, thus eliminating dead space for pneumatic efficiency while providing a collection sump structure at the outlet end 14. It is noted that, unlike the prior art, this preferred embodiment is without an extending appendage below the level of the flange that would detrimentally increase the length and hence increase the resistance and the dead space volume of the system.

FIG. 37C is a top plan view of the adapter 192 of FIG. 37A illustrating in expanded view the flange portion 193. It is noted that the flange 193 extends all the way around the circumference of adapter 192, thus making it much easier to grip from any angle and to directionally direct and control when such control of the adapter 192 is desired, e.g., during intubation or extubation or when connecting or disconnecting the adapter 192 from other devices. Included in the flange construction are partial sockets 195 (as shown) for restraining a stylet (see FIG. 37E) or tubing (as earlier described), open slots 198 for ease of "feeding in" a strap (see FIG. 37D), and a closed slot 197 requiring a strap or tether to be "fed through" the slot 197 for connection, including situations in which at least one more secure tether is required.

It is noted that a stylet retention means permitting a clip or clamp or snap-in connection would eliminate the limitations described above in the discussion of the prior art, and additionally, would have the advantages of reducing the need to wind the stylet around the flange. Less winding simplifies the motion of securing the device and reduces the length necessary for the stylet. Reducing the length of the material would not only save on material and packaging costs, but would also reduce the amount of extraneous material extending out of the proximal portion of the endotracheal tube. Such material can be dangerous to the person intubating, as it might cause facial or eye trauma as one concentrates on a patient's vocal cords and advances the endotracheal tube in close proximity to the face where the stylet might hook or abrade the operator's skin or eye. As there are a number of manufacturers of stylets for endotracheal tubes that may have slightly or grossly varying dimensions, it is preferred to have flanges or multiple flanges that accommodate a variety of sizes of stylets.

Similar to the restraint of stylets, one might also want to restrain other accessories with the use of the flange. For example, one might want to restrain the tubing that is often built into to an endotracheal tube for inflating an endotracheal balloon cuff. Current art leaves these tubes unrestrained and they must be taped by medical personnel to the patient or endotracheal tube. By taping the tubing, one often obstructs the view of the tube if it is done directly to the tubing. If the taping is done to the patient, it increases the risk of a skin reaction to the tape. Of more clinical significance is the possibility that the tape for securing the inflation cuff will be confused with other tape and manipulations of the tape might be made more cumbersome or confused resulting, for example in accidental dislodgement of the endotracheal tube. Having a specialized means for securing a stylet or inflation tube and check valve that simplifies and improves the restraint and maintenance of these connections is desirable. Doing this without compromising the integrity or function of the tubing is also important. For example in some cases it may be desirable to clamp the tubing to assure that no flow or pressure is lost through an open lumen of an inflation cuff or dual lumen endotracheal tube. It other instances it may be undesirable to compress such a tubing, particularly for a long period of time, as this might distort irreversible and detrimentally the inner lumen and its flow properties. It is therefore advantageous to have in some instances a flange with a restraining device or devices, for example of an accessory tubing of an endotracheal tube, that might restrain the tube without compressing the tubing and in other instances it may be desirable to restrain and clamp the tube. Having an improved restraining means would prevent the need to wind an accessory device such as a inflation cuff tubing around the flange and therefore eliminate extraneous material around the opening of patient's mouth or nose. Similarly these principles could be similarly applied to other tracheal tube devices.

Though having flanges with improved extending dimensions and with improved features is desirable as previously described, one would also prefer to limit the overall size of the flanges to the extent that these to not become obstructive, for example to vision during the intubation process. Therefore it would preferable to have flanges that have features with multiple purposes to reduce the space necessary to accommodate this features.

Referring again to the drawings, it is noted that open slots 198 may also have a portion at the entry which serves as a partial socket 195 for tubing restraint. It is also noted that closed slot 197 may serve as a tether holder for tethering the adapter 192 to other devices or equipment, including preferably a reversible tethering restraint such as an adhesive or Velcro strap. It is also noted that the open slots and sockets may restrain the tubing with varying degrees of compression or with no compression. Thus slots 199 preferably have a small enough dimension to effectively "pinch" a tube restrained therein so as to close it when desired. This described flange arrangement embodies herein an adapter body constructed and arranged, at the proximal end of such body, for insertion into a distal female connector of a medical device in such manner as to connect a proximal air port of such adapter to a distal air port of such medical device; on such adapter body, an outwardly-extending flange comprising a substantially full external perimeter constructed and arranged for equal user-grippability from any direction; wherein such flange further comprises a tube-restraining structure constructed and arranged for restraining a tube portion adjacent such adapter; wherein such flange further comprises a strap connector structure constructed and arranged for holding a strap means for holding such adapter in place during use; wherein such strap connector structure is constructed and arranged to permit a sliding engagement of the strap means with such flange for holding such endotracheal tube adapter; wherein such flange further comprises a tether connection structure constructed and arranged to permit such endotracheal tube adapter to be connected to a tether, wherein such tether connection comprises a peripherally-closed opening; and wherein such tube-retaining structure further comprises a tube-pinching structure constructed and arranged for closing the tube portion to be retained. It is seen that another advantage of the present invention is to include the multiple tethering slots and holes which permit the device to be secure in a number of orientations without having to reposition the adaptor. Indeed, these features also permit a variety of arrangements of tethering to be accomplished in a single position, such as a three-tether "tripod" arrangement simultaneously involving slots 197 and 198 on both sides. This might be more desirable to provide additional stability in a given direction. In addition, another advantage of having an open slot is that tethers with preformed loops for specialization, efficiency or stability, for example, can be slid over and surrounding the tethering arm (as at reference no. 198). Such a looped tether would simplify the securing of the tether to the device and provide an instantaneously secure connection, especially with the addition of a restraining appendage 200 (see FIG. 37C) that would prevent the slippage of the looped tether off the device. The open slot would therefore facilitate an even quicker, less cumbersome and more desirable attachment in many cases.]

FIG. 37D is a perspective view illustrating the use of the preferred endotracheal tube adapter 192, showing the adapter 192 in place on the mouth 85 of a child patient 84. Shown connected to flange 193 is a strap system 196 for securing the endotracheal tube in place. Shown in dotted lines is a suction device 15, preferably of the type described herein with reference to FIGS. 7A-C or FIG. 31A, for connecting adapter 192 to a pneumatic line. This arrangement embodies herein wherein such endotracheal tube adapter is connected to an endotracheal tube extending into a patient's lung area, whereby such medical system may provide suction through such endotracheal tube.

FIG. 37E is a perspective view illustrating the retaining of the intubation stylet 194 on the flange 193 of the adapter 192, preferably by snapping the stylet into a partial socket 195.

FIG. 38 is a side elevation view of an endotracheal tube adapter 192 with a preferred endotracheal tube construction 215 according to the present invention, showing a tactilely-apparent diameter reduction 217 (between larger-diameter portion 216 and the distal normal-diameter portion 28) for information feedback to the intubator. In addition, it is preferred, according to this invention, that tube construction 215 also include readable indicia indicating to a user information about the length of endotracheal tube (from the indicia) which is hidden in the patient. Advantages of this embodiment include that there is improved dead space efficiency, and there is an easier connection due to the wider adapter opening to accommodate portion 216. It is noted that the diameter reduction 217 is preferably placed at the level desired for the mouth position so that when the intubator visually or tactilely gets to the lip line, it is realized that the intubator is in the correct position; and this minimizes trauma to the vocal cords, wherein prior art wide diameter tubes tapered tubes often cause such trauma, particularly the prior art neonatal tubes that have a widening of the tube at the distal tip. Such tubes are specifically recommended against by the N.R.P. (Neonatal Resuscitation Program) of the American Heart Association. This arrangement embodies herein an endotracheal tube comprising, at a proximal portion of such endotracheal tube, an enlarged-diameter means for providing tactile feedback to a user about the distance of the intubation insertion point from the user; and, further, such a tube comprising, at a proximal portion of such endotracheal tube, indicia means for providing visual feedback to a user about the distance of the intubation insertion point from the user; and wherein such indicia means comprises a noticeable color.

Figure 39A:
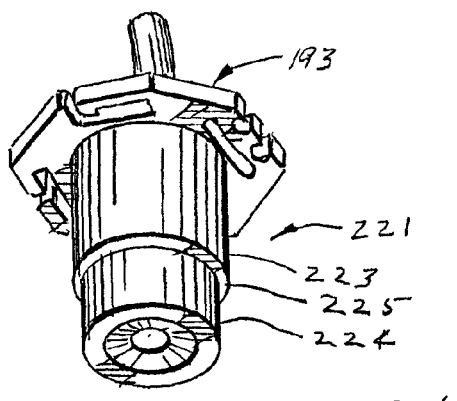
FIG. 39A is a perspective view of another preferred embodiment of an endotracheal tube adapter according to the present invention.
Figure 39B:
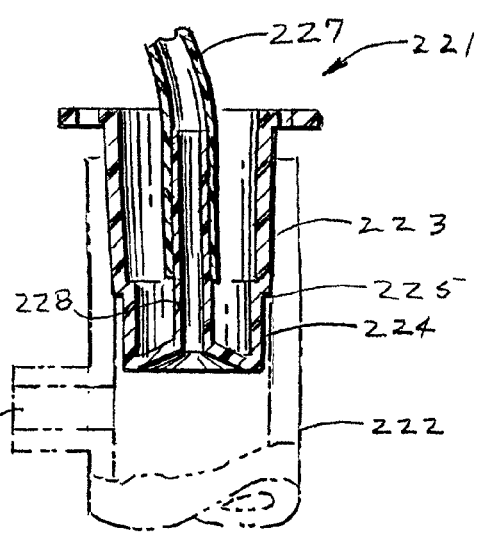
FIG. 39B is a sectional view through the center of the embodiment of FIG. 39A showing details of its inner structure and showing its fit with a receiving end of an item of respiratory equipment.

FIG. 39A is a perspective view of another preferred embodiment of an endotracheal tube adapter 221 according to the present invention. FIG. 39B is a sectional view through the center of the embodiment 221 of FIG. 39A showing details of its inner structure and showing its fit with a receiving end of an item of respiratory equipment 222 (shown in dotted lines). As shown, endotracheal tube adapter 221 is similar to endotracheal tube adapter 192 (see FIGS. 37A-C), including flange 193. However, the structure of this embodiment 221 is designed to minimize dead air space. The cylindrical body of endotracheal tube adapter 221 is stepped downward in diameter from body portion 223 to body portion 224 at step 225. The outside diameter of body portion 223 (as shown) is tapered to provide a friction fit with the inside diameter of the upper end respiratory equipment 222; and the body portion 224 is slightly smaller in diameter so as to just avoid interfering with such fit and prevent the formation of a large gap where secretions and debris could collect and fester. The length of "extension" body portion 224 should be made so as to just avoid any blockage of port 226 of equipment 222; and this minimizes dead space within the upper end of respiratory equipment 222. This arrangement embodies herein an endotracheal tube adapter comprising, in combination: an adapter body constructed and arranged, at the proximal end of such body, for insertion into a distal female connector of a medical device in such manner as to connect a proximal air port of such adapter to a distal air port of such medical device; wherein such adapter body comprises a first male round cylinder constructed and arranged for fitting into a female round cylinder of the female connector of the medical device; a second male round cylinder extending proximally from such first male round cylinder; wherein such second male round cylinder has a slightly smaller diameter than such first male round cylinder and is constructed and arranged for minimizing dead space when connecting such endotracheal tube adapter with such medical device.

Further, in endotracheal tube adapter 221, dead space within adapter 221 is minimized by making the connection of endotracheal tube 227 with adapter 221 reversed male-female from that shown in FIG. 37B; that is, in adapter 221 the bottom end of endotracheal tube 227 is (as a female connector) connected around the tube portion 228 (acting as a male connector) of adapter 221, thus permitting the inner diameter of tube portion 228 to be minimized to limit such internal dead space (acting along with the "sump" construction as shown also in FIG. 37B.

Figure 40A:
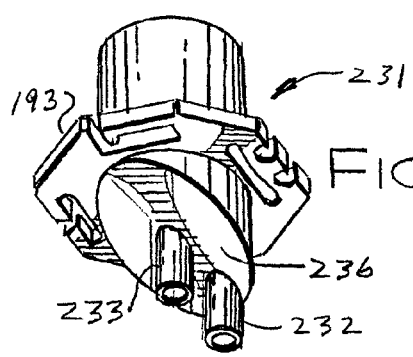
FIG. 40A is a perspective view of yet another preferred embodiment of an endotracheal tube adapter according to the present invention and having an additional opening for use in removing debris or in respiratory monitoring.
Figure 40B:
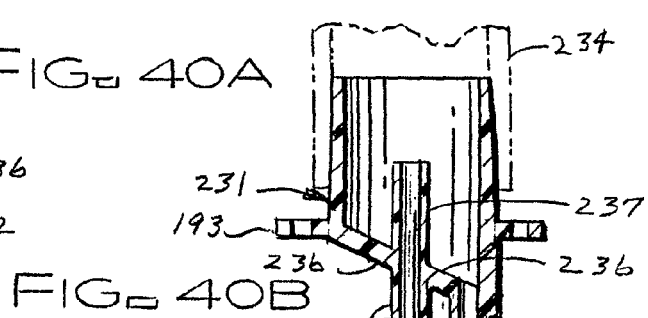
FIG. 40B is a sectional view through the centers of such openings.

FIG. 40A is a perspective view of yet another preferred embodiment of an endotracheal tube adapter 231 according to the present invention and having an additional opening 232 (in addition, that is, to the usual opening 233 for connecting an endotracheal tube 227) for use in removing debris or in respiratory monitoring. FIG. 40B is a sectional view through the centers of such openings 232 and 233. As shown, an endotracheal tube 227 is connected to adapter 231 at one of its ends and respiratory equipment 234 (dotted lines) is connected at the other of its ends. A tube 235 is connected to opening 232 for further connection, as to a specimen collector/remover or an item of respiratory monitoring equipment (not shown). To aid in debris removal (through opening 232), surface 236 adjacent flange 193 is sloped as shown (preferably about 30 degrees from the plane of flange 193) from the plane of flange 193 to the location of opening 232. Thus, debris coming up from endotracheal tube 227 enters endotracheal tube adapter 231 from the upper end of internal tube extension 237 of opening 233 and normally falls to sloped surface 236, from where it normally will collect through opening 232. This arrangement embodies herein wherein such adapter body comprises a distal connector constructed and arranged for, at a distal portion of such body, receiving a proximal end of an endotracheal tube in such manner as to connect a distal air port of such adapter to a proximal air port of such endotracheal tube, such distal connector comprising a cylinder constructed and arranged for connecting with a proximal portion of the endotracheal tube; and wherein such cylinder extends into a central hollow in such body; and wherein such adapter body further comprises, at a distal end of such adapter body, a planar bottom wall sloped from a plane of such flange, and an accessory port through such planar bottom at the distal end of such sloped planar bottom; and further comprising, connected to such accessory port, a device selected from the group consisting of a monitor means for monitoring measurable information within such adapter body, an instilling means for instilling selected substances into such adapter body, and a collection means for collecting specimens from such adapter body; and wherein such collection means is connected to such accessory port; and wherein such female cylinder encompasses a male cylinder structured and arranged for connecting to a female distal end of an endotracheal tube.

Figure 41A:
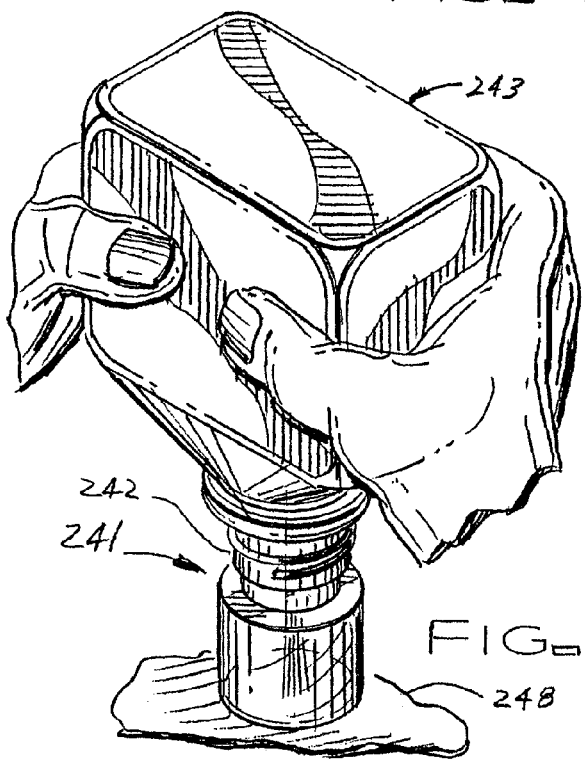
FIG. 41A is a perspective view of another preferred embodiment of a splash shield according to the present invention, which splash shield is shown fitted into the neck of a bottle of the type containing irrigation fluid.
Figure 41B:
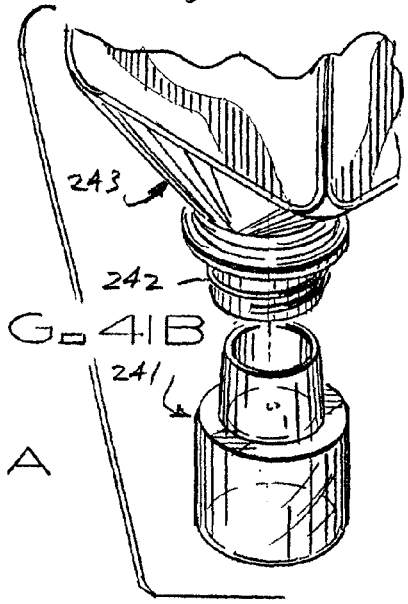
FIG. 41B is a perspective view of the embodiment of FIG. 41A shown detached from the illustrated bottle.

FIG. 41A is a perspective view of another preferred embodiment of a splash shield 241 according to the present invention, which splash shield 241 is shown fitted into the neck 242 of a bottle 243 of the type containing irrigation fluid. FIG. 41B is a perspective view of the embodiment 241 of FIG. 41A shown detached from the illustrated bottle 243. FIG. 41C is a sectional view through the center of the embodiment 241 of FIG. 41A showing structural details and showing its fit in the illustrated bottle 243 (which is in dotted lines). Splash shield 241 (as shown best in FIG. 41C) is stepped from a larger-diameter cylindrical portion 244 to a smaller-diameter portion 245 which is sized with external taper to friction fit as shown within neck 242 of bottle 243 (in dotted lines in FIG. 41C). Thus, for example, squeezing of a squeeze bottle 243 brings irrigation fluid into upper portion 245, from where it may be forced through a hole 246 in dividing surface 247 to impinge upon skin portion 248 (see FIG. 41A) with lower portion 244 acting to shield say, a user, from fluid or debris from a wound on skin portion 248.

FIG. 42A is a perspective view of yet another preferred embodiment of a splash shield 251 according to the present invention shown attached to an IV-type squeeze bag 252 by way of the IV spike connector 253 of this embodiment 251. FIG. 42B is an enlarged (over FIG. 42A) perspective view of the embodiment 251 of FIG. 42A. FIG. 42C is sectional side view of the embodiment 251 of FIG. 42A illustrating the structural details thereof. FIG. 42D is a bottom view of the embodiment 251 of FIG. 42A. Wound irrigation shield 251 is preferably transparent and engineered to be sterilizable and disposable as is commonly done in the medical industry. Connector portion 253 (resembling a commonly available "IV spike") is a male connector with an inner conduit 254 for fluid 255 and a tapered pointed end 256 fits into the outlet end connector 257 of a fluid container such as a sterile IV solution bag 252 as shown in FIG. 42A. Optionally, if desired, there might be an outlet 258 (dotted lines in FIG. 42B) for the attachment to a vacuum source. In operation, fluid 255 is squeezed though conduit 254 of connector portion 253, from where it is forced through hole 259 of dividing surface 260 to form an irrigation stream through shield portion 261 (preferably shaped as shown, where, to better cover body wounds on appendages, as before mentioned, the preferred ratio of a maximum length of the open bottom end compared to a maximum width of such bottom end is at least 1.5:1.0) of wound irrigation shield 251. As shown, it is preferred that one (bottom) edge of the shield portion 261 be substantially linear so to provide a stable pivoting surface to promote a linearly directed irrigation stream. Also, one side 262 of shield portion 261 may preferably be substantially planar so as to increase the user's visibility of the irrigation process. Also, the irrigation stream may preferably be "off-center" to promote proximity to wall surfaces; that would allow better visualization. Also, it is preferred to provide a ledge 263 as shown at the bottom of shield portion 261 for better sealing against a skin portion when desired and for increasing the protective area of the device without increasing the width of the splash area required to form a seal. The arrangements of FIG. 42 embody herein a splash shield system comprising: a transparent body means, having a substantially-open bottom end, for assisting protecting a user from contact with irrigation fluid directed at a patient's wound; an irrigation-source connection means, unitary with such body means, for connecting such body means, at an upper portion of such body means, to a source of irrigation fluid; wherein such irrigation-source connection means comprises an IV-spike connector. This arrangement further embodies herein such a system wherein such body means further comprises a substantially-flat, substantially-vertical first side wall, having a substantially-straight bottom periphery, located to a first side of such irrigation-source connection means, and a continuously-curved second side wall, having a substantially curved bottom periphery, connecting with such first side wall, and wherein such irrigation-source connection means further comprises a directed-stream means for directing a narrow stream of the irrigation fluid towards the wound; and, further, wherein such bottom periphery of such second side wall has a shape of a substantially-circular arc of more than 180 degrees, and such bottom periphery of such second side wall comprises a substantially-flat, substantially-horizontal ledge extending outwardly, wherein the ratio of a maximum length of such bottom end compared to a maximum width of such bottom end is at least 1.5:1.0.

FIG. 43A a is front view illustrating yet another preferred embodiment of a splash shield 271 according to the present invention, showing a spike connector 272 attached to a squeeze bag 273 and also fitted into a cylindrical splash shield element 274. FIG. 43B is a perspective view of the embodiment 271 of FIG. 43A, showing the spike connector 272 separated from the cylindrical splash shield element 274. FIG. 43C is a partial sectional view showing the connection details with the spike connector 272 attached to the cylindrical splash shield element 274. Spike connector 272 is a component of the type commonly used in creating an IV spike dripping chamber for modulating the administration of IV fluid through IV tubing. Splash shield element 274 may be made from standard PVC tubing to create an easily produced IV spike connector wound irrigation shield device 271. By using simple available components in a new configuration and method, the tool investment would be minimized. It would also provide users with familiar equipment and parts that would reduce apprehension over using a new device. Providing this device 271 permanently connected would provide significant advantages in some situations as described above. There may be an optional outlet contour or aperture 275 (see FIG. 43B) which can function as a exit opening for effluent irrigation fluid or for the attachment of a vacuum connector. In addition, the tubing comprising splash shield element 274 may be flexible to prevent discomfort and trauma and to facilitate a better seal against the skin. When device 271 is connected to bag 273, squeezed irrigation fluid 276 is forced through spike conduit 277 and through hole 278 in dividing surface 279, from where it enters attached splash shield element 274 for the described usages in wound irrigation.

FIG. 44A is an exploded perspective view of yet another preferred embodiment of the splash shield 281 of the present invention, showing a syringe-type tip 282, a syringe adapter 283 to control the irrigation stream, and a tubular splash shield element 284. FIG. 44B is a sectional view of the embodiment 281 of FIG. 44A illustrating the details with the parts connected. This arrangement provides a separate transparent shield component 284 which may be connected over a syringe body 285 to easily and quickly transform a standard syringe into a shield wound irrigation delivery device as shown in FIG. 44B. One might want optionally to add adaptor 283 to the syringe tip 282 to modulate the flow. Providing a removable wound irrigation splash shield element 284 over the syringe body 285 would facilitate this by eliminating the need to reach into a potentially narrow, tight fitting sterile space to manipulate, position and exchange connectors.

FIG. 45A is an exploded perspective view of yet another preferred embodiment of the splash shield 291 of the present invention, showing the end 292 of an irrigation bottle 293, a bottle adapter 294 to control the irrigation stream, and a tubular splash shield element 295. FIG. 45B is a sectional view of the embodiment 291 of FIG. 45A illustrating the details with the splash shield 291 connected to the bottle 293 (shown in dotted lines). As shown, to use the splash shield 291, it is preferred to friction fit adapter 294 over the end/neck 292 of bottle 293, and to friction fit splash shield element 295 over the bottom of adapter 294. Then fluid from bottle 293 may be forced into adapter 294, through hole 296, and into the tubular splash shield element areas for wound irrigation.

FIG. 46A is a perspective view of a preferred embodiment of a combined splash shield and irrigation squeeze tube 301 according to the present invention. FIG. 46B is a partial perspective view of the embodiment 301 of FIG. 46A, partially cut away to show its use with cap 302 removed. Toothpaste-type squeeze tube portion 299 has a built-in or a removable transparent wound irrigation shield portion 303. An outlet 304 to allow fluid egress or to allow attachment to a vacuum source (not shown) may be optionally provided for the advantages enumerated previously. Cap 302 is made long enough for removal or attachment to tube portion 299 with shield portion 303 in place. In operation, the tube portion 299 is squeezed, thus forcing irrigation fluid onto a wound, as previously set forth generally. Having a removable shield portion 303 is preferred if cap 302 is to be provided with nozzle 305 adaptations or adaptors (as taught previously herein) that allow modulation and that must be accessed easily in a sterile fashion, particularly if a simple, cheap, and easily available component such as a transparent plastic PVC tubing were used.

FIG. 47A is a perspective view of yet another preferred embodiment of a splash shield 311 according to the present invention. Splash shield 311 is shown with an inlet port 312 attached to an irrigation syringe 313 and an outlet port 314 attached to a vacuum line 315. FIG. 47B is a side view of the embodiment 311 of FIG. 47A, shown attached to the irrigation syringe 313. FIG. 47C is a front view of the embodiment 311 of FIG. 47A, with the irrigation syringe 313 in dotted lines. FIG. 47D is a side sectional view of the embodiment 311 of FIG. 47A showing the structural details and fluid flow directions. FIG. 47E is a top view of the embodiment 311 of FIG. 47A. FIG. 47F is a partial sectional view through the section 47F-47F of FIG. 47B. FIG. 47G is a bottom view of the embodiment 311 of FIG. 47A.

The illustrated preferred embodiment of splash shield 311 has multiple inlet ports 312 and 312a, with varying internal configurations so that various different kinds of syringes or other fluid containers may be attached and variations in spray fineness may be had. Inlet ports 312 and 312a have male and female connection potential to allow for multiple user preferences with a single manually-operated device 311. Alternately to the inlet port configurations illustrated, such ports may in certain applications protrude into the device 311 or be located within the wall of the device 311. Vacuum outlet 314 is located adjacent the 318 base of the device 311 to assist in removal of fluid at the skin surface. As shown, a groove 319 at each bottom side of device 311 acts as a conduit for allowing air and irrigation fluid and debris to be transported to outlet port 314 when downward pressure against the skin is applied while there is a vacuum pull. The grooves 319 form an incomplete seal on a contact surface and widen the base of the device 311, with the groove 319 against the skin becoming an aperture through which such contaminated fluid can be removed. Such grooves 319 are preferred to be located near the base of the shield 311 to prevent or minimize any visual obstruction caused by the vacuum apparatus features for an observer looking from above.

The inlet ports 312 and 312a are preferably made to extend in parallel fashion with the outlet port 314 to simplify manufacturing tooling complexity and cost. It is noted that grooves 319 are preferably located adjacent the outer perimeter 321 of the device 311, thus increasing the total surface area of the device 311 without compromising the smaller area that can form an inner protective or operational seal against the skin for wound irrigation protection, particularly for areas of small surface area or sharp contour. For example, over the sharp edge of the chin, one could form an adequate seal with the inner perimeter formed by the inner wall of the grooves 319. The lateral outer edges of the grooves would increase the effective surface area protection beyond that formed within the inner seal. This device preferably has a longitudinally tapered base 318 or perimeter 321 to facilitate attachment over the skin; and it preferably has a relief port or contour 325 to facilitate the directional outflow of irrigation effluent or to allow the inflow of gas to facilitate the vacuum of irrigation fluid. It is noted that, if desired for certain uses, the vacuum connector 314 may be eliminated; and the illustrated device can be operated with or without a vacuum source connected. It is noted that the inlet on the illustrated device is off center, thus providing a design which permits maximum pivoting ability while maintaining efficient shielding. It is also preferred to have flat side edges 318a and 318b of base 318 to maximize stability of the device when pivoted along the edge, as when one is irrigating along a linear laceration. The arrangements of FIG. 47 (as well as FIGS. 18 and 19) embody herein a splash shield system for irrigation of a patient's wound and suction removal of excess irrigation fluid, comprising: a body means for fluid containment, wherein such body means has a maximum height dimension at a non-peripheral portion and a minimum height dimension at peripheral portions, and wherein a splash portion of the space within such body means, adjacent an irrigation target area, is essentially directly below such non-peripheral portion and along a vertical axis through such maximum height dimension; and an input means, for input of irrigation fluid into such splash portion of such body means, located at a height position intermediate of such maximum height dimension and such minimum height dimension; and, further, comprising an output means for suctioning excess irrigation fluid from within such splash shield, wherein such output means is constructed and arranged to draw excess irrigation fluid from such splash portion toward a location approximately at a position symmetrically opposed (with respect to such axis of such maximum height dimension) from the location of such input means. The arrangements of FIG. 47 further embody wherein such output means further comprises an output nozzle means for attachment to a vacuum line, and a conduit means for directing suction flow across such splash portion toward such output nozzle means, wherein such conduit means comprises at least one channel along a periphery of such body means extending from such output nozzle means to a location approximately at a position symmetrically opposed (with respect to such axis of such maximum height dimension) from the location of such input means; and, further, wherein such input means comprises at least one input nozzle extending from such body means and being substantially parallel to such output nozzle; and, further, wherein such input means further comprises first multiple inlet structures constructed and arranged to be selectively connected, one at a time, to an irrigation source selected from among multiple types of irrigation sources; and, further, wherein such input means further comprises second multiple inlet structures constructed and arranged to each selectively provide a different irrigation streaming flow than an other such second inlet structure; and, further, wherein such body means is tapered from front to rear and from top to bottom.

FIG. 48A is a front view of an alternate preferred embodiment of an endotracheal tube 331 according to the present invention, shown attached to an endotracheal tube adapter 332.

FIG. 48B is a partial enlarged front view, partially in section, of the embodiment 331 of FIG. 48A showing the details of structure and of the connection to endotracheal tube adapter 332. FIG. 48C is a partial perspective view of an upper section of the endotracheal tube 331 of FIG. 48A, showing separation after cutting.

Currently available endotracheal tubes do not have contours to aid in the assessment and alteration of the tubing. They do not have male tapered edges to aid insertion of the tube into an endotracheal tube adaptor. They do not have incrementally contoured tubing to aid in the taping or the securing of the tubing by adding frictional surfaces. They do not have incrementally contoured tubing to aid in the cutting of the endotracheal tube during shortening to assure a proper length is achieved. They do not have incrementally contoured tubing to aid in the placement of the endotracheal tube to a proper depth by giving a tactile and physically recognizable contour that can be used as a standard reference point, such as the oral inlet. They do not have contoured tubing to aid in the structural support of the outer portion of the endotracheal tube. They do not have contoured tubing to aid in the structural support of the outer portion of the endotracheal tube to prevent kinking of the Endotracheal tube. They do not have contoured tubing to aid in the structural support of the outer portion of the Endotracheal tube to prevent kinking by providing a tubing with wider diameters of greater strength in combination with narrower regions that accommodate a limited degree of flexibility.

Endotracheal tube 331 has a proximal patient tracheal insertion end 339 and a mechanical distal end 340. This endotracheal tube 331 has single- or multiple-contours 341 to aid in the placement, assessment, restraint and alteration of the tubing. The distal length of the tube 331 has a surface that can be cut to have either a male tapered surface 342 or female cylindrical surface 343 to aid in the insertion into an endotracheal tube adapter 332 or over an endotracheal tube adapter 332, as shown in FIG. 48B. By cutting along a flat contour 344 that is formed within a groove between the wider contours 345, the device has a predictable incremental surface that can guide a cutting instrument to a desired location with increased precision (as shown best in FIG. 48C), especially over current prior art with no contours.

Contours 341 can aid in providing surfaces with increased frictional properties to aid in taping or securing the endotracheal tubes 331 after insertion. In addition, these contours 341 can be counted or labeled so as to visually and tactilely aid in the assessment of the depth of insertion of the endotracheal tube 331. Currently, tubing is labeled on the flat outer surface. When covered by an operator's fingers, or when looked at from far away, or when covered by tape or another restraining device, these numbers often cannot be seen or visualized. The contours 341 of the present invention would provide both increased visual and tactile assessment. The contours 341 of the present invention may also be made to have a greater wall thickness and therefore give additional structural strength to the distal tubing. The contours 341 of this embodiment 331 begin at approximately a standard reference point of the patient's lip when a tube of a standard diameter such as a 3.5 mm internal diameter is inserted. On a patient of this size, the lip line of an appropriately placed tube would be approximately 10 cm. Thus, the tubing might preferably have the contouring begin at approximately 10 cm. This would be a useful reference for the operating clinician, knowing that one should not insert the endotracheal tube contours 341 past the lip line. The clinician would therefore avoid the complications of inserting an endotracheal tube too far such as a right mainstem bronchus intubation or ruptured bronchus or tracheal bleeding, etc. Having the wider contour only on the distal end would prevent the complications of earlier available tapered endotracheal tubes which are currently discouraged by the Neonatal Resuscitation Committee of the American Heart Association.

The tube 331 may also be made preferably to have a widened internal diameter (i.e., of the female cylindrical surface 343) at approximately the same point as the widened contour on the outside. This would minimize excess dead space within the tube. This would leave the proximal portion of the tubing to retain its bending characteristics while giving the distal tubing a desirable increased stiffness to prevent kinking or jostling or disconnection of ventilation adapters. In the illustrated preferred embodiment, having a widened distal internal diameter would improve connection of male connectors within or allow male suction catheter funnel devices without interfering with the smallest diameter of the endotracheal tube. In the preferred embodiment, the increments of repeating contours would preferably be in units of single or multiple centimeters for ease of the clinician's computations. Having such a widened distal end would allow the endotracheal tube to be inserted into an endotracheal tube adaptor without creating a new constricting diameter, the smallest diameter of the endotracheal tube. Having a thicker-walled proximal end would allow the endotracheal tube to be inserted into an endotracheal tube adaptor with less chance of the tubing being constricted on insertion into a female connector, relative to the more flexible thinner walled proximal end, and less chance of the connection interfering with the flow by preventing a constricting diameter of the endotracheal tube. This would leave the distal portion of the tubing to retain its bending characteristics while giving the proximal portion of the tubing a desirable increased stiffness to prevent kinking or jostling or disconnection of ventilation adaptors. The arrangements of FIG. 48 embody herein wherein such enlarged-diameter means comprises a series of proximal portions of such endotracheal tube, each of such series comprising an external tapered portion, having a proximal end, structured and arranged for friction connection within a female tapered portion of an endotracheal tube adapter; and, further, wherein such enlarged diameter means comprises an enlarged internal diameter, larger than an internal diameter of such endotracheal tube at a distal end of such endotracheal tube; and, further, wherein each of such series further comprises an external groove means for providing an identifiable place between each of such series for user-cutting of such proximal portion of such endotracheal tube, such external groove means being located and structured and arranged so that the user-cutting is at about the proximal end of such external tapered portion; and, further, wherein the length of a distal end of such endotracheal tube, beginning at a distal end of such enlarged-diameter means, is about the length from the lip line of a patient to the bifurcation of the trachea of the patient; and, further, wherein the approximate length of each of such series of proximal portions is selected from the group consisting of one centimeter and two centimeters.

Also, it is noted that it is often necessary to suction the nose of a patient, particularly newborn infants as the are often obligate nose breathers. Currently one either uses a bulb syringe commonly known and available, or a suction catheter. Some parents have been known to place their mouths over a child's nose and perform oral suction. This last method is unpredictable and provides an unregulated vacuum power and exposes the operator directly to the infectious agents that may be causing an abundant amount of nasal secretions. Bulb syringes are often cited by parents and medical personnel as ineffective. Frequently the vacuum created is insufficient to relieve a tenacious nasal secretion obstruction. It is only good for a single short period before needing to be reloaded. While these devices are beneficial in places where a vacuum regulated suction device is unavailable, they are suboptimal in locations such as a hospital emergency room where such equipment is available.

In these locations, one often uses a standard suction catheter such as the one shown in FIG. 2B. Unfortunately the device only operates when a suction force is created. Often there is open space in the opening of the nostril around the suction catheter and free air enters the device rather than the desired secretions. One often has to enter the nostril deeply to retrieve the desired secretions where nasal passages may be more narrow and a seal is created. Sometimes the seal created causes trauma as the suction catheter side relief openings at the tip are occluded and the tubing is withdrawn from the patient and tears the nasal mucosa causing trauma and bleeding. Most bulb syringes have a tapered end to create this seal and to prevent entering the nose too deeply and causing trauma. The current manufacture of suction catheters primarily uses straight tubing. Having a tube as shown in FIGS. 48A and 48B with a large tapered diameter directly attached to the suction catheter control valve would prevent this over-deep insertion from occurring. If such a tapered tube had a corresponding inner diameter widened portion, such a "bubble" formed could be an area of reduced flow and therefore might facilitate visualization of the aspirate. Having both a widened taper with a corresponding narrow taper would facilitate the creation of such a bubble trap. Having such a corresponding narrow taper would permit smaller sized standard valves to be used. Not having such a corresponding narrow taper would permit the use of larger sized connectors that may be standard or may be larger and specialized for large bore suction. Such tubing could have a relief side eyelet in the tapered portion or on a more straight extension portion at the tip. The tapered outer portion of the tubing could make the seal required for creation of the necessary vacuum, while the extension tip could be inserted to a relatively deeper position, without causing the above described trauma. The tubing could be created in a single process, such as the extrusion of PVC tubing. Such a preferably transparent and flexible material could be hole punched to create the safety side eyelet. This could be done in a process without any assembly of components required.

Alternately, a preferred unitary structured flexible transparent conformable tapered tubing with a specimen visualization trap might have an intermediate connector such as that shown as reference number 13 in FIG. 2A. That might give desired functions such as rapid detachment. A device known as the BBG is marketed by Childrens Medical Ventures. This device has a rigid plastic adaptor assembled to a suction tubing that is assembled to a suction catheter valve. Such a device does not have a relief side inlet as is common and necessary. It does not reach beyond the opening of the nose. It requires relatively expensive molding of the distal adaptor and assembly and adherence to the suction tubing to be manufactured. It is not transparent so one cannot see along the entire length of the device to visualize what has been suctioned or possibly to assess any obstructions of the tip. It does not provide a wider inner area of decreased flow which might act as a specimen visualization chamber. It is rigid and therefore less likely to conform against irregular surfaces of the skin to form a seal. It does not have an extension, nor an extension beyond the tapered fitting portion, that might reach in an atraumatic way within the nose to retrieve desired substances.

A new suction device with the new tubing features described above could also have other uses beyond nasal suctioning. For example, in situations where a standard length is known for depth of insertion and one would not want to go farther to prevent a undesirable circumstance such as trauma suctioning. Another example might be the placement of a nasogastric tube. Another example might be in the suctioning of a trachea. Standard lengths are well established for such devices, yet one often cannot see the side markings on a narrow catheter side wall to know the depth of insertion. If the length is limited to the point where the tubing meets the suction valve, then the hand is in close proximity to the trachea stoma that is often obstructed by the chin or neck structures which might prohibit full insertion of the tubing. Having a widened tapered outer tubing wall of a suction catheter could create both a visual and tactile point of reference for the depth of insertion of the tubing. Having such a tapered portion on the tubing away from the suction catheter would permit more maneuverability of the device beyond the neck and still provide a desired length limited suction catheter. Using transparent "bubbled" tubing for this purpose would have the additional specimen visualization and trapping advantages described above. The tapered end might form a seal over the tracheostomy stoma to create the necessary efficient vacuum force required for tracheal clearance, the benefits of the flexible suction tip and tubing being beyond the area where the tapered seal is formed similar to that described for nasal suctioning, but with an even longer length than required for nasal suctioning. Having all the relief eyelets beyond the seal within the patient prevents prevent loss of suctioning to incoming room air. These suction catheter designs could also benefit from the novel variable and incremental control valves with improved restraining features as described elsewhere in this application.

FIG. 49 is a perspective view of yet another preferred embodiment of an endotracheal tube 350 according to the present invention, showing a dual lumen. Endotracheal tube 350 is made up (1) of a single lumen endotracheal tube, preferably endotracheal tube 331 as described with respect to FIGS. 48A-C, and (2) of a second smaller endotracheal tube 351, preferably with a diameter sized for neonatal use. Smaller tube 351 enters larger tube 331 through hole 352 and is located from that point downward within larger tube 331, co-extending with larger tube 331 to the distal end 353 of smaller tube 351, located at approximately the distal end 354 of larger tube 331.

Larger-diameter tube 331 has on its proximal end 357 an endotracheal tube adapter 358 (in dotted lines), ready for connection to a respiratory apparatus (for ventilation); and smaller-diameter tube 351 has on its proximal end 359 a respiratory adapter 360, ready for connection to a respiratory apparatus (for ventilation). Currently available tubing does not have a second dual lumen with a diameter sized for neonatal use with such second dual lumen having a ventilation adaptor. This arrangement allows reduced dead space by reducing the distance from the patient's trachea to the point of carbon dioxide and oxygen exchange by providing a point distal to the patient's lips within the patient's body where distal endings of at least two separate tubes intersect to a common cavity to facilitate the inflow and outflow of two separate gases or gas mixtures, for example the inflow of an oxygen and the outflow of a patient generated carbon dioxide mixture. Also, it is noted that the use of preferred larger tube 331, i.e., the contoured tube of FIGS. 48A-C, assists in the correct depth placement or the physical securing of the tubes/catheters.

Prior art endotracheal tubes with dual lumens are adapted for "instillation and monitoring" through the second tube with a Luer/syringe attachment. The prior art second tubing is very narrow and not ideally suited for high flow instillation of gases for ventilation. There is no means for attachment to any respiratory ventilation devices. The present dual-lumen invention provides a device with standard style small first endotracheal tube that can be inserted using standard means without the second lumen interfering substantially with the inner diameter of the first endotracheal tube. Size limitations are particularly important in the use of such tubing with neonates where size limitations and the physics of the materials and gas flow produce greater limitations than are faced by larger patients that might accommodate other endotracheal tube dual lumen ventilation designs. By reducing this distance of gas exchange as in the present invention, one reduces dead space and more closely approximates the point of normal physiological gas exchange within the oral cavity. Also, preferably, the point of connection of the two tubes would be above the vocal cords of the patient to prevent the potential for trauma associated with other non-tubular insertion arrangements. Preferably, the point of connection exchange of the gases would be at the distal tip of the endotracheal tube to reduce as much as possible the dead space volume. Reducing dead space can significantly improve ventilation dynamics and improve morbidity and mortality of sick patients including premature newborns. In the preferred embodiment, an oxygen gas mixture would be injected through the smaller tubular dual lumen under a high mechanically-generated pressure. The first narrower lumen could have a synchronized valve to prevent pressure leakage and insure lung inflation with the oxygen or gas mixture. The second wider lumen could be available for a lower pressure patient-generated exhalation of a carbon dioxide gas mixture. The wide tube would help facilitate this with a lower resistance to overcome for the expiration of gases. A synchronized valve in the second lumen would prevent loss of pressure and would assist in the directional output of this gas. Appropriate pressures and alarms and fail-safe devices would need to be instituted to prevent injury to the patient as is commonly done. The arrangement of FIG. 49 embodies herein an endotracheal tube comprising a second length of tubing, having a distal end and a proximal end, entering and having a respiratory connection with such endotracheal tube at such distal end of such second length of tubing, wherein such proximal end of such second length of tubing comprises attachment means for attachment of such second length of tubing to a respiratory ventilation device, and wherein such respiratory connection is structured and arranged to permit exchange of respiratory gases at about such distal end of such second length of tubing; and, further, comprising a second length of tubing, having a distal end and a proximal end, entering and having a respiratory connection with such endotracheal tube at such distal end of such second length of tubing, wherein such proximal end of such second length of tubing comprises attachment means for attachment of such second length of tubing to a respiratory ventilation device, and wherein such respiratory connection is structured and arranged to permit exchange of respiratory gases at about such distal end of such second length of tubing.

FIG. 50A is a perspective view of the preferred elements of an unassembled wound treatment kit 370 according to a preferred embodiment of the present invention. FIG. 50B is an exploded perspective view of a preferred embodiment of the wound treatment kit 370 of this invention. FIG. 50C is a perspective view of the exterior of the assembled wound treatment kit 370 of the present invention. FIG. 50D is a sectional view of the illustrated wound treatment kit 370, assembled and filled, through its center and the center of the external pocket 390 in the lower cap 380. FIG. 50E is a sectional view taken through the section 50E-50E of FIG. 50D.

With respect to the prior art discussion herein about treatment of wounds using Dermabond™ or the like as a tissue adhesive for closing lacerations, the sticking of fingers together and other such common problems may be prevented by the use of sterile gloves made of a non-wettable flexible material such as polyethylene. Use of them with a strong tissue adhesive (of the type used for closing lacerations) would decrease the likelihood of inadvertent tissue bonding and permit intimate contact with the tissue for wound approximation. It would permit the use of gloves in close proximity to the wound without inadvertent bonding of the operator or their gloves to the patient. This is not only embarrassing for the medical personnel but requires a distraction force to separate from the patient that might simultaneously pull apart a freshly closed wound. Applying these principles to those in the hospital or office for other wounds, particularly wound lacerations amenable to tissue adhesive closure, it would therefore be ideal to have in a close proximity to each other a medically compatible tissue wound adhesive and a sterile glove of a non-wettable material such as polyethylene as in a medical kit. As these devices are often used either independently with or in concert with a number of other wound care products such as alcohol, butadiene, antiseptic, gauze, tissue adhesive or wound irrigation products such as sterile gauze, a drape, a towel, an irrigation shield, and a fluid reservoir, it would be desirable to have all or some of these devices together in a kit. Such a kit would preferably contain all of these components. It would preferably be self-contained, amenable to sterilization and tamper-proof. Such a kit would preferably be compact for easier storage and shipping. Such a kit would allow separately sterilized components to be assembled in such a kit and preferably in a compact kit. Such a kit could be provided by using the internal dimensions of a splash shield, for example the wound irrigation shield 64 illustrated in FIG. 20. By placing a cap on each end separate compartments are discretely created. The kit could by contained with some or all of the necessary components contained within the shielded and capped interior or interiors.

With reference to FIGS. 50A and 50B, wound treatment kit 370 preferably includes splash shield 64, upper splash shield cap 371, lower splash shield cap 380, glove 372 (preferably a pair), gauze 373, alcohol packet 374, towel 375, tissue adhesive packet 376, and textured finger pads 377. Lower cap 380 preferably includes an external pocket 390 for holding tissue adhesive packet 376, preferably by friction fit. Splash shield 64 is divided by shelf 81 into a smaller (upper) cavity 64a and larger (lower) cavity 64b (see FIG. 20). Preferably, gauze 373, alcohol (or other disinfectant) packet 374 and textured finger pads 377 are placed inside the smaller cavity 64a of splash shield 64 before cap 371 is attached to cover cavity 64a. Preferably, gloves 372 and towel 375 are placed inside the larger cavity 64b of splash shield 64 before cap 380 is attached to cover cavity 64b. Then, tissue adhesive packet 376 may be placed inside pocket 390.

With reference to FIGS. 50C-E, the assembled kit 370 is preferably constructed in such manner that sterility of the elements inside the assembled kit 370 is assured. Preferably caps 371 and 380 have adjacent edges (i.e., the edges 386 on their respective open ends) when placed in covering position on splash shield 64, as shown. Preferably, a tamper-evident seal 385 is placed around the periphery of shield 64 and covering such edges 386 of caps 371 and 380 so as to guarantee sterileness in an acceptable way.

It is noted in passing that, with short caps (i.e., not fully covering shield 64) and a transparent shield 64, one could see the contents of the kit 370, which would be desirable for marketing. This kit 370 could also be made tamper evident after sterilization by inclusion within a sealed pouch or tray in well-known ways (not shown). Alternatively, the caps 371 and 380 themselves might form the tamper evident enclosure. Each open end 386 of the cap would preferably have a tamper evident seal, such as an adhesive strip. Preferably, the caps 371 and 380 are made of PVC compound such as the plastisol marketed by Dempsey Ind. Of Miamisburg, Ohio. By having the caps 371 and 380 extend along the contoured fit of the outer dimension of the shield 64, the preferred compact nature of the kit 370 would be maintained. By having the open ends 386 of the caps 371 and 380 of sufficient length to meet one another along the length of the shield, one forms a single location for the placement of a tamper evident seal 385 as described above. One would break open the seal 385 and then open remove the caps 371 and 380 forming the outer shell, much as one would open a plastic egg. The contents would remain sterile and the caps 371 and 380 themselves would function as sterile receptacles for the kit items or for other purposes, such as sterile irrigation solution basins, for example. The caps could have inner and outer indentations for the restraint of other products. As above discussed, an invagination or pocket 390 in the end/outer wall (as shown, for example) of at least one of the caps 371 and 380 may be provided to form a receptacle, preferably to secure the tissue adhesive (or another product, if desired). As this tissue adhesive product is a pharmaceutical, it will most often undergo a very different sterilization validation procedure from the medical splash shield device and kit implements and will most certainly be originating from a different location than the splash shield manufactory. It is therefore preferable to create, assemble and sterilize the kit 370 and later insert the tissue adhesive or other component later in a separate outer compartment, as shown. This compartment or pocket 381 could in turn have its own seal if desired.

Gloves 372 could be used independently of the finger pads 377, as they are readily available in a non-sterile form. But such use would not normally provide as cosmetically pleasing a wound closure as using a texturized surface to provide optimal skin positioning before using a tissue adhesive. A preferred solution for this is to use specialized textured finger pads 377 over one or two of the gloved fingers in such manner as to manipulate the patient's skin properly, controlling the individual fingers to provide optimal positioning and dexterity associated with human manual manipulation. Finger pads 377 preferably will be attached to the fingers by just friction pressure, or in some cases where desired by a restraint or adhesive. The texturized surface of finger pads 377 increases the friction on the skin, and are preferably controlled by the fingers with increased control provided by the restraining means. The texturized surface would preferably be a collection of spikes and preferably would have at least one linear edge and at least one area of double-row spikes. The material of the texturized surface would preferably be a sterile, transparent, disposable, and preferably made of a non-wettable non-adherent medical grade plastic such as polyethylene or polybutylene. Use of such non-adherent finger pads would increase the dexterity of the manipulations involved in the procedure, and therefore provide more cosmetically appealing wound closure, as well as overcoming the limitations of the prior art. They could also provide a flat surface gripping means when desirable, but would have the versatility of providing a non-flat gripping surface. The arrangements of FIG. 50 embody herein a system comprising: a first end cap and a second end cap, such first end cap having a cap portion structured and arranged to close such first end of such body means, and such second end cap having a cap portion structured and arranged to close such second end of such body means; and, wherein each such end cap comprises a substantially hollow cylindrical portion having an open end, and each such hollow cylindrical portion is structured and arranged so that, when such end caps are in place closing such first and second ends of such body means, such open ends of such hollow cylindrical portions are adjacently located; and, further, comprising seal means for, when such open ends of such hollow cylindrical portions are in place on such body means and adjacently located, covering and sealing such open ends in such manner as to protect internal sterileness of such body means; and wherein such seal means comprises tape means for circumferential use around such body means, and wherein such tape means comprises a tamper-evident seal. The described system also embodies herein such a system further comprising at least one glue-resistant glove structured and arranged to protect the user's hand from unsafe substances, and to resist sticking to fast-setting glue of the type for sealing skin lacerations; and, further, comprising texturized finger pad means for temporary attachment to at least one gloved finger of the user for providing the gloved finger with a friction surface for use in pulling a patient's skin into a desired position for use of a such fast-setting glue. It also embodies such a system further comprising wound care products structured and arranged for carrying within such body means; and, further, wherein such glove and such wound care products are stored within such body means, and such end caps are in place over such ends of such body means; and, further, wherein at least one such end cap portion of a such end cap comprises an externally-open pocket extending into such hollow cylindrical portion of such end cap; and wherein such pocket is structured and arranged for fully holding a sealed package of fast-acting glue; and, further, comprising a such sealed package of fast-acting glue. They would also have the advantage over prior art (such as relatively large wound closure forceps) of having a small size and therefore being easier to handle and package. An example of such packaging advantages includes the ability of the smaller finger gripping pads to be stored in a relatively small space such as within the capped container kit 370 described above.

Although such finger pads 377 may in some cases be used without gloves, to provide additional protection to the medical personnel using such finger pads they may want to use gloves to reduce infectious risks and prevent self-inflicted tissue adhesion. The examples described pertain specifically to medical devices, but such a kit would be beneficial for common household situations and would prevent numerous Emergency room visits and other morbidity each year to these common household accidents. By providing a glove as described above in close proximity with a strong adhesive, such as cyanoacrylate, in a procedure kit, for example an inexpensive form fill and seal kit, for common household repairs, one would be promoting the same principles of prevention that apply to putting seat belts in cars, i.e., keeping people out of emergency rooms. So the described packaging of FIG. 50 also embodies herein a method of marketing a fast-acting glue, to minimize resulting needs for medical care for unwanted adhesions involving a user's skin, comprising: placing a first packaging containing such fast-acting glue into a second packaging; placing at least one glue-resistant glove into such second packaging; and marketing such second packaging containing at least such first packaging and such glue-resistant glove; whereby a user of such second packaging may make use of such fast-acting glue while wearing such glue-resistant glove to minimize resulting needs for medical care for unwanted adhesions involving the user's skin.

It is noted that FIG. 1B shows prior art of a rigid suction catheter device on what appears to be a standard sized suction device. If such a connection were sequential in nature using multiple devices that could be used independently or interchanged with various specialized and independent functions, one would have a single device that had numerous specialized suction capabilities. In fact, if the first tubing were a large diameter greater than the standard ⅜" and ½" tubing commonly used, but of a larger size that might fit the larger pour spout of the suction catheter device, one could have multiple devices that would fit interchangeably and telescopically in one unit to provide many specialized suction functions including a large bore suction of ⅞". Such tubing would not have a restricting diameter if connected to other devices of equal or smaller diameter. The devices might have outer stoppers. Such smaller diameter devices would have to have at least one segment that would be wide enough and configured in a cylindrical fashion, for example, to form a seal on the inner wall of preferred round internal diameter of the tubing. The distal devices might be constructed of a rigid hard material that would be resistant to breakage under the crushing pressures of a person biting on it and might even have a specialized contour to act as a bite block with an open inner diameter that is also capable of being connected to a suction source. This would allow the tip area to have such strong properties while the other segments might be made of a rigid or a flexible material. A flexible material might facilitate the attachment and interchangability with other components, including enabling a curve component to be inserted to a sufficient depth to create a sufficient frictional interference for attached and permit an orientation located in any position around a central axis. As suction catheters are frequently in a generally curved orientation, this would be desirable. The flexible portion could also be more easily constructed of extruded PVC component tubing using standard hole punching techniques to create a suction control valve. Alternatively, a novel suction control valve as described in other portions of this application could be created within the wall of a flexible PVC tubing or in the wall of control valve of a different configuration with the improved restraining features also described elsewhere. The interchangeable components might include a Yankauer, a flexible suction catheter, an oral airway, relief basket adaptor, an oversized rigid suction tube, and therefore give medical personnel a wide range of options not currently available using current art. The devices would be designed so that they would not be limited by the lack of attachment with other devices. The control of suction might be on a more proximal segment as describe or on the accessory component itself. A portion, including an extension, of the inserted accessory might obstruct the control valve internally and proximal on at least one of the devices. Such a constructed accessory might also have the capability of being rotated or moved to a different depth such that the obstructing surface might obstruct, partially obstruct, or leave unobstructed a control valve in the proximally located device.

Although applicant has described applicant's preferred embodiments of this invention, it will be understood that the broadest scope of this invention includes such modifications as diverse shapes and sizes and materials. Such scope is limited only by the below claims as read in connection with the above specification. Further, many other advantages of applicant's invention will be apparent to those skilled in the art from the above descriptions and the below claims.

What is claimed is:

1. A medical system for use with separate user-hand-held-type medical components usable by a user in related medical procedures, comprising:
   a) at least one first said separate user-hand-held-type medical component located in a first position;
   b) restraint means integrally fixed on said first separate medical component for temporarily restraining, without substantial interference with normal use of said first separate medical component, at least one second said separate user-hand-held-type medical component in a second position adjacent said first position for ready availability for potential use by the user;
   c) wherein said restraint means is structured and arranged for restraining multiple kinds of user-hand-held-types of equipment;
   d) wherein said restraint means comprises at least one elongated prong with a first longitudinal central axis;
   e) wherein said first separate user-hand-held-type medical component comprises a hollow tube with a second longitudinal central axis;
   f) wherein said first longitudinal central axis is substantially parallel with said second longitudinal central axis;
   g) wherein the at least one second said separate user-hand-held-type medical component is restrainable between said at least one elongated prong and said hollow tube.

2. The medical system according to claim 1 wherein said restraint means is structured and arranged for temporary clipping of said first separate medical component to a non-hand-held-type item of equipment, wherein said restraint means is structured and arranged for use in said clipping with multiple sizes and types of said equipment.

3. The medical system according to claim 2 further comprising an external aperture means for regulating suction wherein said external aperture means comprises single-finger-operable valve means for user control of suction-vacuum variation in said medical system.

4. A medical system for regulating suction, comprising:
   a) a user-hand-held-type medical component structured and arranged for use in a suction system and comprising at least one external aperture means for regulating suction and at least one internal aperture means for regulating suction;
   b) wherein said external aperture means comprises
      i) single-finger-operable valve means for repeatable incremental user control of suction-vacuum variation in said suction system, and
      ii) tactile feedback means for amplifying tactile feedback to a user to enhance distinguishing of control increments;
   c) wherein said single-finger-operable valve means comprises
      i) at least one primary aperture portion structured and arranged for regulating primary suction, and
      ii) at least one secondary aperture portion structured and arranged for regulating fine relief suction;
   d) cap means for temporarily blocking said at least one internal aperture means.

5. A medical system for use with user-hand-held-type medical components usable by a user in related medical procedures, comprising a first said user-hand-held-type medical component comprising:
   a) first outlet means for attaching a vacuum source;
   b) a body means for transporting air from inside said body means to said first outlet means;
   c) first inlet means for attaching a suction catheter to said body means;
   d) second inlet means for providing assistance in regulating air flow into said first inlet means; and
   e) third inlet means for attaching a second user-hand-held-type medical component selected from the group consisting of
      i) an endotracheal tube adapter, ii) a specimen trap, and iii) a cap means for temporary sealing of said third inlet means;

f) wherein said body means comprises a round cylinder portion having a central axis, and said second and third inlet means are disposed in line with said central axis such that a straight line extending said central axis and having a plurality of points collinear with said central axis would pass through both said second and third inlet means.

6. The medical system according to claim 5 wherein:

a) said third inlet means is structured and arranged to permit attachment to the endotracheal tube adapter;

b) said third inlet means is structured and arranged to permit attachment to the specimen trap; and c) said third inlet means is structured and arranged to permit attachment to the cap means for temporary sealing of said third inlet means;

d) said third inlet means is structured and arranged so that the user may select one second user-hand-held-type medical component for attachment to said third inlet means.

7. The medical system according to claim 5 wherein:

a) said body means is, internally, substantially cylindrical in shape; and b) said body means comprises a circumferential internal seal means for making a seal with an endotracheal tube adapter when said adapter may be attached in said third inlet means;

c) wherein said seal means is located proximally from said first inlet means.

8. The medical system according to claim 5 wherein:

a) said second inlet means comprises i) first aperture means for regulating air flow in said first user-hand-held-type medical component from a first portion of said first user-hand-held-type medical component, and ii) second aperture means for regulating air flow in said first user-hand-held-type medical component from a second portion of said first user-hand-held-type medical component.

9. The medical system according to claim 5 further comprising:

a) a removable cylindrical specimen trap having an open end connected in said third inlet means;

b) said open end of said cylindrical specimen trap being structured and arranged to be sealed by a said cap means.

10. The medical system according to claim 5 further comprising an endotracheal tube adapter having a proximal end connected in said third inlet means.

11. The medical system according to claim 5 further comprising:

a) an endotracheal tube adapter having a proximal end connected in said third inlet means;

b) wherein said medical system is structured and arranged so that said first inlet means is blocked when said endotracheal tube adapter is connected in said third inlet means.

12. The medical system according to claim 8 further comprising:

a) a cap means for temporarily sealing said third inlet means;

b) wherein said cap means is structured and arranged, while sealing said third inlet means, for regulating air flow through said second aperture means by movement of portions of said cap means by a user's finger.

13. The medical system according to claim 12 wherein said cap means is structured and arranged, while sealing said third inlet means, for sealing said second aperture means.

14. The medical system according to claim 13 wherein said body means contains a suction-collected medical specimen and wherein said cap means is sealing said third inlet means and said second aperture means.

15. The medical system according to claim 14 further comprising:

a) a sealed connection between said first outlet means and said first inlet means;

b) whereby said suction-collected medical specimen may be safely sealed within said body means for transport.

16. The medical system according to claim 15 wherein said sealed connection comprises flexible tubing and Luer adaptors for connecting said flexible tubing.

17. The medical system according to claim 5 wherein:

a) said endotracheal tube adapter is connected to an endotracheal tube extending into a patient's lung area;

b) wherein said medical system may provide suction through said endotracheal tube.

18. A medical component comprising:

a) first outlet means for attaching a vacuum source;

b) a body means for transporting air from inside said body means to said first outlet means;

c) first inlet means for attaching an endotracheal tube to said body means; and d) second inlet means for providing assistance in regulating air flow into said first inlet means;

e) wherein said body means comprises a round cylinder portion having a central axis, and said first and second inlet means are disposed in line with said central axis such that a straight line extending said central axis and having a plurality of points collinear with said central axis would pass through both said first and second inlet means.

19. The medical component of claim 18 wherein said first inlet means is structured and arranged for attaching a second medical component in line with said central axis.

20. A medical system for use with separate user-hand-held-type medical components usable by a user in related medical procedures, comprising:

a) at least one first outlet adapted to attach to a vacuum source;

b) at least one body adapted to transport air from inside said at least one body to said at least one first outlet;

c) at least one first inlet adapted to detachably couple to at least one suction catheter; and d) at least one prong permanently attached to said at least one body;

e) wherein said at least one first outlet and said at least one prong together form at least one clip adapted to attach the medical component system to at least one second medical component.

21. A medical component system comprising:

a) at least one first outlet adapted to attach to a vacuum source;

b) at least one body adapted to transport air from inside said at least one body to said at least one first outlet;

c) at least one first inlet adapted to attach a suction catheter to said at least one body; and d) at least one second inlet adapted to provide assistance in regulating air flow into said at least one first inlet;

e) wherein said at least one body comprises a chamber having a central axis, and said at least one first inlet and said at least one second inlet are disposed in line with said central axis such that a straight line extending said central access and having a plurality of points collinear with said central axis would pass through both said at least one first inlet and said at least one second inlet.

22. The medical component system according to claim 21 wherein said at least one first inlet and said at least one second inlet are structured and arranged to permit at least one straight, rigid wire to be inserted through said second inlet so as to reach said at least one first inlet without the wire bending or the wire touching any solid material.

23. The medical component system according to claim 21 wherein said medical component system consists essentially of one integral piece.

24. A medical component system comprising:
 a) at least one first outlet adapted to attach to a vacuum source;
 b) at least one body adapted to transport air from inside said at least one body to said at least one first outlet;
 c) at least three inlets adapted to allow air into said at least one body;
 d) wherein at least one of said at least three inlets is adapted to provide repeatable incremental finger regulation of suction pressure within said body;
 e) wherein at least one of said at least three inlets is adapted to provide detachable coupling to a medical suction device;
 f) wherein said at least one body comprises a central axis and said at least one of said at least three inlets adapted to provide repeatable incremental finger regulation and said at least one of said at least three inlets adapted to provide detachable coupling to a medical suction device are disposed in line with said central axis such that a straight line extending said central axis and having a plurality of points collinear with said central axis would pass through said at least one of said at least three inlets adapted to provide repeatable incremental finger regulation and said at least one of said at least three inlets adapted to provide detachable coupling to a medical suction device.

25. The medical component system according to claim 24 wherein said at least three inlets are structured and arranged so that coupling a medical suction device to one of said at least three inlets blocks the flow of air through at least one of said at least three inlets into said at least one body.

26. The medical component system according to claim 25 wherein said at least three inlets are adapted so that blocking said at least one of said at least three inlets adapted to provide finger regulation of suction pressure within said body restricts air flow into said at least one body through just one of said at least three inlets.

27. The medical component system according to claim 24 wherein said medical suction device comprises an endotracheal tube.

28. The medical component system according to claim 24 wherein said medical suction device comprises a flexible suction tube.

29. The medical component system according to claim 24 wherein said medical suction device comprises a flexible oropharyngeal suction catheter tip adapted to suction upper respiratory passages of a person.

30. A medical component system comprising:
 a) at least one first outlet adapted to attach to a vacuum source;
 b) at least one body adapted to transport air from inside said at least one body to said at least one first outlet;
 c) at least one first inlet adapted to provide finger regulation of air flow into said at least one body;
 d) wherein said at least one first inlet comprises at least one coupler adapted to detachably couple to at least one medical device;
 e) at least one second inlet adapted to allow air into said at least one body;
 f) wherein said at least one second inlet may be regulated through said at least one first inlet;
 g) wherein said at least one body comprises a central axis and said at least one first inlet and said at least one second inlet are disposed in line with said central axis such that a straight line extending said central axis and having a plurality of points collinear with said central axis would pass through said at least one first inlet and said at least one second inlet.

31. The medical component system according to claim 30 wherein said at least one second inlet comprises a hollow tubular protrusion.

32. The medical component system according to claim 30 wherein said at least one coupler comprises a hollow tapered connector.

33. The medical component system according to claim 30 wherein said at least one coupler is adapted to connect to at least one endotracheal tube.

34. A medical component system, related to attachment to a vacuum source and at least one user-hand-held-type medical component, comprising:
 a) at least one first outlet adapted to attach to the vacuum source; and
 b) at least one body adapted to transport air from inside said at least one body to said at least one first outlet;
 c) at least three inlets adapted to allow air into said at least one body;
 d) wherein at least one of said at least three inlets is adapted to attach to the at least one user-hand-held-type medical component;
 e) wherein said medical component system is structured and arranged so that one of said at least three inlets is adapted to provide single-finger-operable finger regulation of suction pressure within said body when the at least one user-hand-held-type medical component is attached to said medical component system;
 f) wherein said medical component system is structured and arranged so that one of said at least three inlets is adapted to provide single-finger-operable finger regulation of suction pressure within said body when the at least one user-hand-held-type medical component is not attached to said medical component system
 g) wherein said at least one body comprises a chamber having a central axis and a first inlet and a second inlet of said at least three inlets are disposed in line with said central axis such that a straight line extending said central axis and having a plurality of points collinear with said central axis would pass through both said first and second inlets;
 h) wherein said first inlet and said second inlet are structured and arranged to permit at least one rigid stylette to be inserted through said second inlet so as to reach said first inlet without the stylette bending or the stylette touching any solid material.

35. A medical component system, related to attachment to a vacuum source and at least one user-hand-held-type medical component, comprising:
 a) at least one first outlet adapted to attach to a vacuum source; and
 b) at least one body adapted to transport air from inside said at least one body to said at least one first outlet;

c) at least three inlets adapted to allow air into said at least one body;

d) wherein at least one of said at least three inlets is adapted to provide single-finger-operable finger regulation of suction pressure within said body;

e) wherein at least one of said at least three inlets is adapted to provide detachable coupling to the at least one user-hand-held-type medical component, f) wherein said at least one first outlet comprises at least one first attacher with a first dimension;

g) wherein at least one of said at least three inlets comprises at least one second attacher with a second dimension;

h) wherein said first dimension is not equal to said second dimension;

i) wherein when said second attacher is attached to the user-hand-held-type medical component, a single finger is capable of fully activating suction pressure into said body through only a single inlet, and j) wherein when said second attacher is not attached to the user-hand-held-type medical component, a single finger is capable of fully activating suction pressure into said body through only a single inlet;

k) wherein said at least one body comprises a round cylinder portion having a central axis and a first inlet and a second inlet of said at least three inlets are disposed in line with said central axis such that a straight line extending said central axis and having a plurality of points collinear with said central axis would pass through both said first and second inlets;

l) wherein said first inlet and said second inlet are structured and arranged to permit at least one straight, rigid stylette to be inserted through said second inlet so as to reach said first inlet without the stylette bending or the stylette touching any solid material.

36. The medical system for regulating suction according to claim 4 wherein said at least one secondary aperture portion comprises at least one slot.

37. The medical system for regulating suction according to claim 4 wherein said at least one primary aperture portion is positioned on a first plane and said at least one secondary aperture portion is positioned on a second plane.

38. The medical system for regulating suction according to claim 37 wherein said first plane and said second plane are connected with at least one ramp portion.

39. The medical system according to claim 5 wherein said second inlet and said third inlet are structured and arranged to permit at least one rigid stylette to be inserted through said second inlet so as to reach said third inlet without the stylette bending or the stylette touching any solid material.

* * * * *